US012758154B2

(12) United States Patent
Valdez

(10) Patent No.: US 12,758,154 B2
(45) Date of Patent: Oct. 13, 2026

(54) SENSOR STABILIZER

(71) Applicant: EDWARDS LIFESCIENCES CORPORATION, Irvine, CA (US)

(72) Inventor: Michael G. Valdez, Riverside, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 838 days.

(21) Appl. No.: 18/164,172

(22) Filed: Feb. 3, 2023

(65) Prior Publication Data

US 2023/0181114 A1 Jun. 15, 2023

Related U.S. Application Data

(63) Continuation of application No. PCT/US2021/012799, filed on Jan. 8, 2021.

(60) Provisional application No. 63/060,333, filed on Aug. 3, 2020.

(51) Int. Cl.

| | |
|---|---|
| ***A61B 5/00*** | (2006.01) |
| ***A61B 5/0215*** | (2006.01) |
| ***A61B 17/11*** | (2006.01) |
| *A61B 17/00* | (2006.01) |

(52) U.S. Cl.

CPC .......... *A61B 5/6886* (2013.01); *A61B 5/0215* (2013.01); *A61B 5/6869* (2013.01); *A61B 5/6882* (2013.01); *A61B 5/6883* (2013.01); *A61B 5/6884* (2013.01); *A61B 17/11* (2013.01); *A61B 2017/00022* (2013.01); *A61B 2017/1139* (2013.01); *A61B 2560/066* (2013.01)

(58) Field of Classification Search
None
See application file for complete search history.

(56) References Cited

U.S. PATENT DOCUMENTS

| | | | |
|---|---|---|---|
| 3,538,917 | A | 11/1970 | Selker |
| 3,675,656 | A | 7/1972 | Hakim |
| 3,730,186 | A | 5/1973 | Edmunds, Jr. et al. |
| 3,853,126 | A | 12/1974 | Schulte |
| 3,882,862 | A | 5/1975 | Berend |
| 3,882,882 | A | 5/1975 | Preisig |
| 3,903,894 | A | 9/1975 | Rosen et al. |
| 4,256,094 | A | 3/1981 | Kapp et al. |
| 4,428,365 | A | 1/1984 | Hakky |

(Continued)

FOREIGN PATENT DOCUMENTS

| | | | |
|---|---|---|---|
| JP | 2014531247 | A | 11/2014 |
| JP | 2018108120 | A | 7/2018 |

(Continued)

OTHER PUBLICATIONS

Emil Mantini, MD, et al., Title: Congenital Anomalies Involving the Coronary Sinus, Circulation, Journal of the American Heart Association, vol. XXXIII, Feb. 1966, pp. 317-327.

(Continued)

*Primary Examiner* — Meredith Weare
(74) *Attorney, Agent, or Firm* — Chang and Hale LLP

(57) ABSTRACT

A sensor-retention structure includes a sensor-support arm configured to hold a sensor device and a stabilizer structure associated with the sensor-support arm and configured to project away from the sensor-support arm and provide stabilizing support for the sensor-support arm.

20 Claims, 27 Drawing Sheets

(56) References Cited

U.S. PATENT DOCUMENTS

| | | | |
|---|---|---|---|
| 4,556,050 | A | 12/1985 | Hodgson et al. |
| 4,578,061 | A | 3/1986 | Lemelson |
| 4,586,501 | A | 5/1986 | Claracq |
| 4,601,718 | A | 7/1986 | Possis et al. |
| 4,655,777 | A | 4/1987 | Dunn et al. |
| 4,708,140 | A | 11/1987 | Baron |
| 4,712,551 | A | 12/1987 | Rayhanabad |
| 4,739,762 | A | 4/1988 | Palmaz |
| 4,762,128 | A | 8/1988 | Rosenbluth |
| 4,774,949 | A | 10/1988 | Fogarty |
| 4,828,544 | A | 5/1989 | Lane et al. |
| 4,861,336 | A | 8/1989 | Helzel |
| 4,881,939 | A | 11/1989 | Newman |
| 4,946,457 | A | 8/1990 | Elliott |
| 4,950,227 | A | 8/1990 | Savin et al. |
| 4,961,729 | A | 10/1990 | Vaillancourt |
| 4,997,431 | A | 3/1991 | Isner et al. |
| 5,026,377 | A | 6/1991 | Burton et al. |
| 5,054,492 | A | 10/1991 | Scribner et al. |
| 5,108,420 | A | 4/1992 | Marks |
| 5,109,420 | A | 4/1992 | Nonaka |
| 5,167,239 | A | 12/1992 | Cohen et al. |
| 5,190,528 | A | 3/1993 | Fonger et al. |
| 5,193,546 | A | 3/1993 | Shaknovich |
| 5,201,757 | A | 4/1993 | Heyn et al. |
| 5,242,397 | A | 9/1993 | Barath et al. |
| 5,242,410 | A | 9/1993 | Melker |
| 5,258,042 | A | 11/1993 | Mehta |
| 5,267,940 | A | 12/1993 | Moulder |
| 5,287,861 | A | 2/1994 | Wilk |
| 5,330,496 | A | 7/1994 | Alferness |
| 5,334,217 | A | 8/1994 | Das |
| 5,345,940 | A | 9/1994 | Seward et al. |
| 5,354,279 | A | 10/1994 | Hofling |
| 5,366,490 | A | 11/1994 | Edwards et al. |
| 5,373,849 | A | 12/1994 | Maroney et al. |
| 5,419,777 | A | 5/1995 | Hofling |
| 5,423,878 | A | 6/1995 | Franz |
| 5,429,634 | A | 7/1995 | Narciso, Jr. |
| 5,431,700 | A | 7/1995 | Sloan |
| 5,443,497 | A | 8/1995 | Venbrux |
| 5,445,600 | A | 8/1995 | Abdulla |
| 5,445,646 | A | 8/1995 | Euteneuer et al. |
| 5,456,284 | A | 10/1995 | Ryan et al. |
| 5,456,712 | A | 10/1995 | Maginot |
| 5,462,523 | A | 10/1995 | Samson et al. |
| 5,464,395 | A | 11/1995 | Faxon et al. |
| 5,491,224 | A | 2/1996 | Bittner et al. |
| 5,496,311 | A | 3/1996 | Abele et al. |
| 5,499,630 | A | 3/1996 | Hiki et al. |
| 5,507,724 | A | 4/1996 | Hofmann et al. |
| 5,507,725 | A | 4/1996 | Savage et al. |
| 5,538,504 | A | 7/1996 | Linden et al. |
| 5,551,954 | A | 9/1996 | Buscemi et al. |
| 5,554,182 | A | 9/1996 | Dinh et al. |
| 5,570,693 | A | 11/1996 | Jang et al. |
| 5,571,086 | A | 11/1996 | Kaplan et al. |
| 5,571,151 | A | 11/1996 | Gregory |
| 5,588,960 | A | 12/1996 | Edwards et al. |
| 5,597,378 | A | 1/1997 | Jervis |
| 5,599,300 | A | 2/1997 | Weaver et al. |
| 5,614,204 | A | 3/1997 | Cochrum |
| 5,628,784 | A | 5/1997 | Strecker |
| 5,661,133 | A | 8/1997 | Leiden et al. |
| 5,662,609 | A | 9/1997 | Slepian |
| 5,662,711 | A | 9/1997 | Douglas |
| 5,665,077 | A | 9/1997 | Rosen et al. |
| 5,669,880 | A | 9/1997 | Solar |
| 5,682,906 | A | 11/1997 | Sterman et al. |
| 5,690,670 | A | 11/1997 | Davidson |
| 5,693,029 | A | 12/1997 | Leonhardt |
| 5,704,361 | A | 1/1998 | Seward et al. |
| 5,704,926 | A | 1/1998 | Sutton |
| 5,713,363 | A | 2/1998 | Seward et al. |
| 5,713,853 | A | 2/1998 | Clark et al. |
| 5,718,725 | A | 2/1998 | Sterman et al. |
| 5,724,975 | A | 3/1998 | Negus et al. |
| 5,724,977 | A | 3/1998 | Yock et al. |
| 5,728,123 | A | 3/1998 | Lemelson et al. |
| 5,735,847 | A | 4/1998 | Gough et al. |
| 5,738,658 | A | 4/1998 | Maus et al. |
| 5,743,874 | A | 4/1998 | Fischell et al. |
| 5,755,682 | A | 5/1998 | Knudson et al. |
| 5,756,696 | A | 5/1998 | Gray et al. |
| 5,771,895 | A | 6/1998 | Slager |
| 5,772,629 | A | 6/1998 | Kaplan |
| 5,772,632 | A | 6/1998 | Forman |
| 5,807,258 | A | 9/1998 | Cimochowski et al. |
| 5,807,306 | A | 9/1998 | Shapland et al. |
| 5,810,780 | A | 9/1998 | Brimhall et al. |
| 5,814,005 | A | 9/1998 | Barra et al. |
| 5,827,216 | A | 10/1998 | Igo et al. |
| 5,830,222 | A | 11/1998 | Makower |
| 5,830,224 | A | 11/1998 | Cohn et al. |
| 5,836,913 | A | 11/1998 | Orth et al. |
| 5,843,090 | A | 12/1998 | Schuetz |
| 5,843,170 | A | 12/1998 | Ahn |
| 5,944,738 | A | 8/1999 | Amplatz et al. |
| 5,951,569 | A | 9/1999 | Tuckey et al. |
| 5,989,280 | A | 11/1999 | Euteneuer et al. |
| 6,019,788 | A | 2/2000 | Butters et al. |
| 6,042,589 | A | 3/2000 | Marianne |
| 6,053,891 | A | 4/2000 | DeCampli |
| 6,081,738 | A | 6/2000 | Hinohara et al. |
| 6,086,553 | A | 7/2000 | Akbik |
| 6,092,526 | A | 7/2000 | LaFontaine et al. |
| 6,095,878 | A | 8/2000 | Van Balen |
| 6,113,612 | A | 9/2000 | Swanson et al. |
| 6,120,494 | A | 9/2000 | Jonkman |
| 6,120,522 | A | 9/2000 | Vrba et al. |
| 6,120,534 | A | 9/2000 | Ruiz |
| 6,152,937 | A | 11/2000 | Peterson et al. |
| 6,165,185 | A | 12/2000 | Shennib et al. |
| 6,168,620 | B1 | 1/2001 | Kerr |
| 6,168,820 | B1 | 1/2001 | Garwood et al. |
| 6,174,681 | B1 | 1/2001 | Halling et al. |
| 6,190,353 | B1 | 2/2001 | Makower et al. |
| 6,193,734 | B1 | 2/2001 | Bolduc et al. |
| 6,196,230 | B1 | 3/2001 | Hall et al. |
| 6,241,743 | B1 | 6/2001 | Levin et al. |
| 6,248,117 | B1 | 6/2001 | Blatter |
| 6,251,116 | B1 | 6/2001 | Shennib et al. |
| 6,254,631 | B1 | 7/2001 | Thompson |
| 6,280,412 | B1 | 8/2001 | Pederson, Jr. et al. |
| 6,283,951 | B1 | 9/2001 | Flaherty et al. |
| 6,287,332 | B1 | 9/2001 | Bolz et al. |
| 6,290,728 | B1 | 9/2001 | Phelps et al. |
| 6,302,875 | B1 | 10/2001 | Makower et al. |
| 6,302,892 | B1 | 10/2001 | Wilk |
| 6,302,905 | B1 | 10/2001 | Goldsteen et al. |
| 6,309,415 | B1 | 10/2001 | Pulnev et al. |
| 6,315,752 | B1 | 11/2001 | DiMatteo |
| 6,325,798 | B1 | 12/2001 | Edwards et al. |
| 6,361,545 | B1 | 3/2002 | Macoviak et al. |
| 6,375,615 | B1 | 4/2002 | Flaherty et al. |
| 6,387,116 | B1 | 5/2002 | McKenzie et al. |
| 6,387,119 | B2 | 5/2002 | Wolf et al. |
| 6,391,036 | B1 | 5/2002 | Berg et al. |
| 6,402,767 | B1 | 6/2002 | Nash et al. |
| 6,443,158 | B1 | 9/2002 | LaFontaine et al. |
| 6,451,048 | B1 | 9/2002 | Berg et al. |
| 6,458,140 | B2 | 10/2002 | Akin et al. |
| 6,464,665 | B1 | 10/2002 | Heuser |
| 6,468,303 | B1 | 10/2002 | Amplatz et al. |
| 6,475,226 | B1 | 11/2002 | Belef et al. |
| 6,494,889 | B1 | 12/2002 | Fleischman et al. |
| 6,503,247 | B2 | 1/2003 | Swartz et al. |
| 6,506,201 | B2 | 1/2003 | Di Caprio et al. |
| 6,508,824 | B1 | 1/2003 | Flaherty et al. |
| 6,561,998 | B1 | 5/2003 | Roth et al. |
| 6,562,066 | B1 | 5/2003 | Martin |
| 6,565,542 | B2 | 5/2003 | Kumar et al. |
| 6,575,168 | B2 | 6/2003 | LaFontaine et al. |
| 6,579,311 | B1 | 6/2003 | Makower |

(56) References Cited

U.S. PATENT DOCUMENTS

| | | | |
|---|---|---|---|
| 6,589,251 | B2 | 7/2003 | Yee et al. |
| 6,595,941 | B1 | 7/2003 | Blatter |
| 6,602,241 | B2 | 8/2003 | Makower et al. |
| 6,613,074 | B1 | 9/2003 | Mitelberg et al. |
| 6,616,624 | B1 | 9/2003 | Kieval |
| 6,616,675 | B1 | 9/2003 | Evard et al. |
| 6,620,202 | B2 | 9/2003 | Bottcher et al. |
| 6,623,494 | B1 | 9/2003 | Blatter |
| 6,626,920 | B2 | 9/2003 | Whayne |
| 6,638,293 | B1 | 10/2003 | Makower et al. |
| 6,692,482 | B2 | 2/2004 | Heller et al. |
| 6,695,878 | B2 | 2/2004 | McGuckin, Jr. et al. |
| 6,699,256 | B1 | 3/2004 | Logan et al. |
| 6,702,828 | B2 | 3/2004 | Whayne |
| 6,709,414 | B2 | 3/2004 | Weitzel et al. |
| 6,709,444 | B1 | 3/2004 | Makower |
| 6,712,836 | B1 | 3/2004 | Berg et al. |
| 6,719,804 | B2 | 4/2004 | St. Pierre |
| 6,726,659 | B1 | 4/2004 | Stocking et al. |
| 6,726,677 | B1 | 4/2004 | Flaherty et al. |
| 6,736,825 | B2 | 5/2004 | Blatter et al. |
| 6,740,426 | B2 | 5/2004 | Kawachi et al. |
| 6,743,244 | B2 | 6/2004 | Blatter et al. |
| 6,743,259 | B2 | 6/2004 | Ginn |
| 6,746,426 | B1 | 6/2004 | Flaherty et al. |
| 6,748,484 | B1 | 6/2004 | Henderson et al. |
| 6,758,854 | B1 | 7/2004 | Butler et al. |
| 6,776,785 | B1 | 8/2004 | Yencho et al. |
| 6,797,083 | B2 | 9/2004 | Peterson |
| 6,802,858 | B2 | 10/2004 | Gambale et al. |
| 6,805,706 | B2 | 10/2004 | Solovay et al. |
| 6,808,498 | B2 | 10/2004 | Laroya et al. |
| 6,827,698 | B1 | 12/2004 | Kleinekofort |
| 6,847,348 | B2 | 1/2005 | Rojewski |
| 6,854,172 | B2 | 2/2005 | Kaese et al. |
| 6,858,035 | B2 | 2/2005 | Whayne |
| 6,869,437 | B1 | 3/2005 | Hausen et al. |
| 6,893,413 | B2 | 5/2005 | Martin |
| 6,913,600 | B2 | 7/2005 | Valley et al. |
| 6,913,607 | B2 | 7/2005 | Ainsworth et al. |
| 6,915,154 | B1 | 7/2005 | Docherty et al. |
| 6,926,690 | B2 | 8/2005 | Renati |
| 6,972,023 | B2 | 12/2005 | Whayne et al. |
| 6,979,351 | B2 | 12/2005 | Forsell et al. |
| 6,985,774 | B2 | 1/2006 | Kieval et al. |
| 7,002,491 | B2 | 2/2006 | Robbins |
| 7,008,397 | B2 | 3/2006 | Tweden et al. |
| 7,011,094 | B2 | 3/2006 | Rapacki et al. |
| 7,011,678 | B2 | 3/2006 | Tenerz et al. |
| 7,025,741 | B2 | 4/2006 | Cull |
| 7,025,746 | B2 | 4/2006 | Tal |
| 7,037,329 | B2 | 5/2006 | Martin |
| 7,056,294 | B2 | 6/2006 | Khairkhahan et al. |
| 7,056,320 | B2 | 6/2006 | Utley et al. |
| 7,056,325 | B1 | 6/2006 | Makower et al. |
| 7,077,860 | B2 | 7/2006 | Yan et al. |
| 7,083,631 | B2 | 8/2006 | Houser et al. |
| 7,108,701 | B2 | 9/2006 | Evens et al. |
| 7,115,136 | B2 | 10/2006 | Park et al. |
| 7,118,546 | B2 | 10/2006 | Blatter |
| 7,128,750 | B1 | 10/2006 | Stergiopulos |
| 7,175,644 | B2 | 2/2007 | Cooper et al. |
| 7,182,771 | B1 | 2/2007 | Houser et al. |
| 7,235,095 | B2 | 6/2007 | Haverkost et al. |
| 7,294,115 | B1 | 11/2007 | Wilk |
| 7,316,706 | B2 | 1/2008 | Bloom et al. |
| 7,317,951 | B2 | 1/2008 | Schneider et al. |
| 7,318,804 | B2 | 1/2008 | Weitzel et al. |
| 7,326,221 | B2 | 2/2008 | Sakamoto et al. |
| 7,331,985 | B2 | 2/2008 | Thompson et al. |
| 7,335,220 | B2 | 2/2008 | Khosravi et al. |
| 7,351,247 | B2 | 4/2008 | Kupiecki et al. |
| 7,361,181 | B2 | 4/2008 | Hindrichs et al. |
| 7,374,567 | B2 | 5/2008 | Heuser |
| D581,054 | S | 11/2008 | Moore |
| 7,462,162 | B2 | 12/2008 | Phan et al. |
| 7,476,200 | B2 | 1/2009 | Tal |
| 7,530,963 | B2 | 5/2009 | Albright |
| 7,563,277 | B2 | 7/2009 | Case et al. |
| 7,623,926 | B2 | 11/2009 | Rossing et al. |
| 7,625,593 | B2 | 12/2009 | Mandrusov et al. |
| 7,628,768 | B2 | 12/2009 | Faul et al. |
| D612,499 | S | 3/2010 | Ondracek et al. |
| 7,691,110 | B2 | 4/2010 | Secrest et al. |
| 7,699,863 | B2 | 4/2010 | Marco et al. |
| 7,722,549 | B2 | 5/2010 | Nakao |
| 7,722,665 | B2 | 5/2010 | Anwar et al. |
| 7,744,621 | B2 | 6/2010 | Paul et al. |
| 7,780,686 | B2 | 8/2010 | Park et al. |
| 7,794,495 | B2 | 9/2010 | Gale et al. |
| 7,807,191 | B2 | 10/2010 | Iyer et al. |
| 7,815,590 | B2 | 10/2010 | Cooper |
| 7,815,656 | B2 | 10/2010 | Rust et al. |
| 7,815,852 | B2 | 10/2010 | Sternby |
| 7,828,814 | B2 | 11/2010 | Brenneman et al. |
| 7,846,179 | B2 | 12/2010 | Belef et al. |
| 7,846,194 | B2 | 12/2010 | Hartley et al. |
| 7,850,705 | B2 | 12/2010 | Bachinski et al. |
| 7,867,547 | B2 | 1/2011 | Tochterman et al. |
| 7,879,367 | B2 | 2/2011 | Heublein et al. |
| 7,892,246 | B2 | 2/2011 | Akin et al. |
| 7,892,247 | B2 | 2/2011 | Conston et al. |
| 7,923,022 | B2 | 4/2011 | Wang et al. |
| 7,951,194 | B2 | 5/2011 | Gueriguian et al. |
| 7,959,603 | B2 | 6/2011 | Wahr et al. |
| 7,964,210 | B2 | 6/2011 | Wang et al. |
| 7,967,769 | B2 | 6/2011 | Faul et al. |
| 7,972,346 | B2 | 7/2011 | Bachmann et al. |
| 8,002,821 | B2 | 8/2011 | Stinson |
| 8,016,782 | B2 | 9/2011 | Brenneman et al. |
| 8,029,470 | B2 | 10/2011 | Whiting et al. |
| 8,048,150 | B2 | 11/2011 | Weber et al. |
| 8,052,751 | B2 | 11/2011 | Aklog et al. |
| 8,057,534 | B2 | 11/2011 | Boismier et al. |
| 8,070,708 | B2 | 12/2011 | Rottenberg et al. |
| 8,088,171 | B2 | 1/2012 | Brenneman |
| 8,089,029 | B2 | 1/2012 | Flanagan |
| 8,091,556 | B2 | 1/2012 | Keren et al. |
| 8,128,689 | B2 | 3/2012 | Weber et al. |
| 8,152,773 | B2 | 4/2012 | Albrecht et al. |
| 8,182,527 | B2 | 5/2012 | Llanos et al. |
| 8,214,015 | B2 | 7/2012 | Macaulay et al. |
| 8,221,495 | B2 | 7/2012 | Shrivastava et al. |
| 8,226,592 | B2 | 7/2012 | Brenneman et al. |
| D665,500 | S | 8/2012 | Martin et al. |
| 8,282,591 | B2 | 10/2012 | Khan et al. |
| 8,308,682 | B2 | 11/2012 | Kramer et al. |
| 8,357,193 | B2 | 1/2013 | Phan et al. |
| 8,376,979 | B2 | 2/2013 | Kapadia |
| 8,382,697 | B2 | 2/2013 | Brenneman et al. |
| D679,015 | S | 3/2013 | Nakaji |
| 8,409,167 | B2 | 4/2013 | Roschak |
| 8,500,697 | B2 | 8/2013 | Kurth et al. |
| 8,506,984 | B2 | 8/2013 | Cook et al. |
| 8,518,062 | B2 | 8/2013 | Cole et al. |
| 8,518,662 | B2 | 8/2013 | Ritzen et al. |
| 8,545,552 | B2 | 10/2013 | Garrison et al. |
| 8,641,724 | B2 | 2/2014 | Brenneman et al. |
| 8,657,790 | B2 | 2/2014 | Tal et al. |
| 8,696,611 | B2 | 4/2014 | Nitzan et al. |
| D705,427 | S | 5/2014 | Jagger et al. |
| 8,768,487 | B2 | 7/2014 | Farnan et al. |
| 8,784,860 | B2 | 7/2014 | Falotico et al. |
| 8,882,830 | B2 | 11/2014 | Cartledge et al. |
| 8,920,449 | B2 | 12/2014 | Wilkinson |
| 8,926,545 | B2 | 1/2015 | Brenneman et al. |
| 8,932,341 | B2 | 1/2015 | Brenneman |
| D723,166 | S | 2/2015 | Igaki et al. |
| 8,951,276 | B2 | 2/2015 | Kellerman et al. |
| 9,005,155 | B2 | 4/2015 | Sugimoto |
| 9,044,588 | B2 | 6/2015 | Conn |
| 9,061,115 | B2 | 6/2015 | Ward et al. |
| 9,067,050 | B2 | 6/2015 | Gallagher et al. |
| 9,198,756 | B2 | 12/2015 | Aklog et al. |

(56) References Cited

U.S. PATENT DOCUMENTS

| | | | |
|---|---|---|---|
| 9,232,997 | B2 | 1/2016 | Sugimoto et al. |
| 9,277,995 | B2 | 3/2016 | Celermajer et al. |
| 9,345,485 | B2 | 5/2016 | Dakin et al. |
| 9,439,746 | B2 | 9/2016 | Bell et al. |
| 9,456,812 | B2 | 10/2016 | Finch et al. |
| 9,550,022 | B2 | 1/2017 | Brenneman et al. |
| 9,649,480 | B2 | 5/2017 | Sugimoto et al. |
| 9,681,948 | B2 | 6/2017 | Levi et al. |
| 9,693,800 | B2 | 7/2017 | Aman et al. |
| 9,775,636 | B2 | 10/2017 | Fazio et al. |
| 9,789,294 | B2 | 10/2017 | Taft et al. |
| 9,814,483 | B2 | 11/2017 | Vardi |
| 9,827,404 | B2 | 11/2017 | Nance et al. |
| 9,839,517 | B2 | 12/2017 | Centola et al. |
| 9,872,981 | B2 | 1/2018 | Sparks et al. |
| 9,980,815 | B2 | 5/2018 | Nitzan et al. |
| 10,039,905 | B1 | 8/2018 | Taft et al. |
| 10,076,403 | B1 | 9/2018 | Eigler et al. |
| 10,130,371 | B2 | 11/2018 | Dehdashtian et al. |
| 10,232,098 | B2 | 3/2019 | Brenneman et al. |
| 10,272,230 | B2 | 4/2019 | Malek et al. |
| 10,292,690 | B2 | 5/2019 | Celermajer et al. |
| 10,327,746 | B2 | 6/2019 | Glimsdale et al. |
| 10,413,284 | B2 | 9/2019 | McNamara et al. |
| 10,426,482 | B2 | 10/2019 | Rafiee et al. |
| 10,426,497 | B2 | 10/2019 | Chou et al. |
| 10,433,851 | B2 | 10/2019 | Adams et al. |
| 10,456,259 | B2 | 10/2019 | Subramanian et al. |
| 10,543,113 | B2 | 1/2020 | Vong et al. |
| 10,561,423 | B2 | 2/2020 | Sharma |
| 10,565,835 | B2 | 2/2020 | Harrington et al. |
| 10,568,751 | B2 | 2/2020 | McNamara |
| 10,595,999 | B2 | 3/2020 | Vettukattil et al. |
| 10,709,451 | B2 | 7/2020 | Gronberg et al. |
| 10,835,394 | B2 | 11/2020 | Nae et al. |
| 10,898,698 | B1 | 1/2021 | Eigler et al. |
| 10,925,731 | B2 | 2/2021 | Bishop et al. |
| 10,925,756 | B2 | 2/2021 | Perszyk |
| 10,940,296 | B2 | 3/2021 | Keren |
| 11,135,054 | B2 | 10/2021 | Nitzan et al. |
| 11,135,410 | B2 | 10/2021 | Finch et al. |
| 11,234,702 | B1 | 2/2022 | Eigler et al. |
| 11,291,807 | B2 | 4/2022 | Eigler et al. |
| 11,298,117 | B2 | 4/2022 | Hariton et al. |
| 11,304,698 | B2 | 4/2022 | Sharma |
| 11,395,644 | B2 | 7/2022 | Alanbaei |
| 11,420,034 | B2 | 8/2022 | Solomon et al. |
| 2001/0000041 | A1 | 3/2001 | Selmon et al. |
| 2001/0025643 | A1 | 10/2001 | Foley |
| 2001/0045698 | A1 | 11/2001 | Lo |
| 2002/0013616 | A1 | 1/2002 | Carter et al. |
| 2002/0029079 | A1 | 3/2002 | Kim et al. |
| 2002/0062146 | A1 | 5/2002 | Makower et al. |
| 2002/0169466 | A1 | 11/2002 | Peterson et al. |
| 2002/0193751 | A1 | 12/2002 | Theeuwes et al. |
| 2003/0017150 | A1 | 1/2003 | Torphy |
| 2003/0060876 | A1 | 3/2003 | Loshakove et al. |
| 2003/0065345 | A1 | 4/2003 | Weadock |
| 2003/0120292 | A1 | 6/2003 | Park et al. |
| 2003/0181928 | A1 | 9/2003 | Vidlund et al. |
| 2003/0225425 | A1 | 12/2003 | Kupiecki et al. |
| 2004/0064081 | A1 | 4/2004 | Stanish |
| 2004/0087984 | A1 | 5/2004 | Kupiecki et al. |
| 2004/0087997 | A1 | 5/2004 | Brenneman |
| 2004/0092879 | A1 | 5/2004 | Kraus et al. |
| 2004/0098105 | A1 | 5/2004 | Stinson et al. |
| 2004/0215168 | A1 | 10/2004 | Verrier et al. |
| 2004/0215220 | A1 | 10/2004 | Dolan et al. |
| 2004/0215323 | A1 | 10/2004 | Stiger |
| 2004/0230156 | A1 | 11/2004 | Schreck et al. |
| 2004/0249335 | A1 | 12/2004 | Faul et al. |
| 2004/0260318 | A1 | 12/2004 | Hunter et al. |
| 2005/0021085 | A1 | 1/2005 | Abrams et al. |
| 2005/0038501 | A1 | 2/2005 | Moore et al. |
| 2005/0043708 | A1 | 2/2005 | Gleeson et al. |
| 2005/0049675 | A1 | 3/2005 | Wallace |
| 2005/0060041 | A1 | 3/2005 | Phan et al. |
| 2005/0075655 | A1 | 4/2005 | Bumbalough et al. |
| 2005/0075656 | A1 | 4/2005 | Beaupre |
| 2005/0082226 | A1 | 4/2005 | Bene et al. |
| 2005/0107723 | A1 | 5/2005 | Wehman et al. |
| 2005/0149096 | A1 | 7/2005 | Hilal et al. |
| 2005/0165344 | A1 | 7/2005 | Dobak |
| 2005/0228402 | A1 | 10/2005 | Hofmann |
| 2005/0249770 | A1 | 11/2005 | Hunter |
| 2005/0249776 | A1 | 11/2005 | Chen et al. |
| 2005/0272806 | A1 | 12/2005 | Falotico et al. |
| 2006/0024359 | A1 | 2/2006 | Walker et al. |
| 2006/0034466 | A1 | 2/2006 | Form et al. |
| 2006/0047337 | A1 | 3/2006 | Brenneman |
| 2006/0111704 | A1 | 5/2006 | Brenneman et al. |
| 2006/0130591 | A1 | 6/2006 | Perkins |
| 2006/0130767 | A1 | 6/2006 | Herchen |
| 2006/0182536 | A1 | 8/2006 | Rice et al. |
| 2006/0198869 | A1 | 9/2006 | Furst et al. |
| 2006/0241342 | A1 | 10/2006 | Macaulay et al. |
| 2006/0264801 | A1 | 11/2006 | Bolling et al. |
| 2006/0264986 | A1 | 11/2006 | Park et al. |
| 2006/0271196 | A1 | 11/2006 | Saal et al. |
| 2006/0293701 | A1 | 12/2006 | Ainsworth et al. |
| 2007/0083258 | A1 | 4/2007 | Falotico et al. |
| 2007/0173787 | A1 | 7/2007 | Huang et al. |
| 2007/0179426 | A1 | 8/2007 | Selden |
| 2007/0213750 | A1 | 9/2007 | Weadock |
| 2008/0021485 | A1 | 1/2008 | Catanese et al. |
| 2008/0051883 | A1 | 2/2008 | Llanos et al. |
| 2008/0071178 | A1* | 3/2008 | Greenland ......... A61N 1/36564 600/486 |
| 2008/0091264 | A1 | 4/2008 | Machold et al. |
| 2008/0109069 | A1 | 5/2008 | Coleman et al. |
| 2008/0161904 | A1 | 7/2008 | Heuser et al. |
| 2008/0167595 | A1 | 7/2008 | Porter et al. |
| 2008/0234842 | A1 | 9/2008 | Zhang |
| 2009/0125097 | A1 | 5/2009 | Bruszewski et al. |
| 2009/0143713 | A1 | 6/2009 | Van Dam et al. |
| 2009/0149947 | A1 | 6/2009 | Frohwitter |
| 2009/0187116 | A1 | 7/2009 | Noishiki et al. |
| 2009/0281379 | A1 | 11/2009 | Binmoeller et al. |
| 2010/0030321 | A1 | 2/2010 | Mach |
| 2010/0106171 | A1 | 4/2010 | Arepally et al. |
| 2010/0198041 | A1 | 8/2010 | Christian et al. |
| 2010/0217382 | A1 | 8/2010 | Chau et al. |
| 2010/0268316 | A1 | 10/2010 | Brenneman et al. |
| 2010/0298930 | A1 | 11/2010 | Orlov |
| 2011/0096036 | A1 | 4/2011 | McIntosh et al. |
| 2011/0106118 | A1 | 5/2011 | Son et al. |
| 2011/0251482 | A1 | 10/2011 | Kellerman et al. |
| 2012/0041544 | A1 | 2/2012 | Wolf |
| 2012/0053686 | A1 | 3/2012 | McNamara et al. |
| 2012/0143141 | A1 | 6/2012 | Verkaik et al. |
| 2012/0265229 | A1 | 10/2012 | Rottenberg et al. |
| 2013/0022214 | A1 | 1/2013 | Dickins et al. |
| 2013/0030521 | A1 | 1/2013 | Nitzan et al. |
| 2013/0178784 | A1 | 7/2013 | McNamara et al. |
| 2013/0253342 | A1 | 9/2013 | Griswold et al. |
| 2013/0281988 | A1 | 10/2013 | Magnin et al. |
| 2014/0172060 | A1* | 6/2014 | Bornzin ................. A61N 1/059 607/126 |
| 2014/0183828 | A1 | 7/2014 | Xu et al. |
| 2014/0203939 | A1 | 7/2014 | Harrington et al. |
| 2014/0213916 | A1* | 7/2014 | Doan ................... A61B 5/0215 600/488 |
| 2014/0222040 | A1 | 8/2014 | Park et al. |
| 2014/0275865 | A1* | 9/2014 | Tammam ............. A61B 5/6882 606/151 |
| 2014/0276395 | A1 | 9/2014 | Wilson et al. |
| 2014/0277054 | A1 | 9/2014 | McNamara et al. |
| 2014/0278442 | A1 | 9/2014 | Hong et al. |
| 2015/0119796 | A1 | 4/2015 | Finch |
| 2015/0148731 | A1 | 5/2015 | Mcnamara et al. |
| 2015/0151101 | A1 | 6/2015 | Bonnette et al. |
| 2015/0230742 | A1* | 8/2015 | Silver .................. A61B 5/0031 600/348 |
| 2015/0238729 | A1 | 8/2015 | Jenson et al. |

(56) References Cited

U.S. PATENT DOCUMENTS

| | | | |
|---|---|---|---|
| 2016/0022293 | A1 | 1/2016 | Dubrul et al. |
| 2016/0022970 | A1 | 1/2016 | Forcucci et al. |
| 2016/0058452 | A1 | 3/2016 | Brenneman et al. |
| 2016/0120550 | A1 | 5/2016 | McNamara et al. |
| 2016/0220357 | A1 | 8/2016 | Anand et al. |
| 2016/0270810 | A1 | 9/2016 | Vardi et al. |
| 2016/0296317 | A1 | 10/2016 | Timmermans et al. |
| 2016/0323977 | A1 | 11/2016 | Sun et al. |
| 2017/0090865 | A1 | 3/2017 | Armstrong-Muntner et al. |
| 2017/0106176 | A1* | 4/2017 | Taft .................... A61M 27/008 |
| 2017/0113026 | A1 | 4/2017 | Finch |
| 2017/0128705 | A1 | 5/2017 | Forcucci et al. |
| 2017/0281339 | A1 | 10/2017 | Levi et al. |
| 2017/0303959 | A1 | 10/2017 | Feng et al. |
| 2017/0319823 | A1 | 11/2017 | Yacoby et al. |
| 2017/0340460 | A1 | 11/2017 | Rosen et al. |
| 2018/0177516 | A1 | 6/2018 | Vardi et al. |
| 2019/0008628 | A1 | 1/2019 | Eigler et al. |
| 2019/0054304 | A1* | 2/2019 | Maile ................... A61N 1/3756 |
| 2019/0269392 | A1 | 9/2019 | Celermajer et al. |
| 2019/0298909 | A1 | 10/2019 | Cully et al. |
| 2020/0023186 | A1* | 1/2020 | Reddy .................. A61N 1/0563 |
| 2020/0054867 | A1 | 2/2020 | Schwartz et al. |
| 2020/0085600 | A1 | 3/2020 | Schwartz et al. |
| 2020/0101270 | A1 | 4/2020 | Sutherland |
| 2020/0170662 | A1 | 6/2020 | Vardi et al. |
| 2020/0187945 | A1 | 6/2020 | Rowe et al. |
| 2020/0254228 | A1 | 8/2020 | Taft et al. |
| 2020/0261704 | A1 | 8/2020 | Wang et al. |
| 2020/0289196 | A1 | 9/2020 | Arevalos et al. |
| 2020/0315599 | A1 | 10/2020 | Nae et al. |
| 2020/0368505 | A1 | 11/2020 | Nae et al. |
| 2020/0391016 | A1 | 12/2020 | Passman et al. |
| 2021/0007790 | A1 | 1/2021 | Takahashi et al. |
| 2021/0007791 | A1 | 1/2021 | Takahashi et al. |
| 2021/0007800 | A1 | 1/2021 | Takahashi et al. |
| 2021/0045691 | A1 | 2/2021 | Zou et al. |
| 2021/0059650 | A1 | 3/2021 | Eidenschink et al. |
| 2021/0077186 | A1 | 3/2021 | Pate et al. |
| 2021/0085935 | A1 | 3/2021 | Fahey et al. |
| 2021/0092522 | A1 | 3/2021 | Draper et al. |
| 2021/0121179 | A1 | 4/2021 | Ben-David et al. |
| 2021/0153776 | A1 | 5/2021 | Minar et al. |
| 2021/0161637 | A1 | 6/2021 | Eigler et al. |
| 2021/0177508 | A1 | 6/2021 | Kellerman |
| 2021/0236138 | A1 | 8/2021 | Perszyk et al. |
| 2021/0290214 | A1 | 9/2021 | Cole et al. |
| 2021/0369321 | A1 | 12/2021 | Yang et al. |
| 2021/0401494 | A1 | 12/2021 | Passman et al. |
| 2022/0001154 | A1 | 1/2022 | Rowe et al. |
| 2022/0008014 | A1 | 1/2022 | Rowe et al. |
| 2022/0031327 | A1 | 2/2022 | Manash et al. |
| 2022/0039667 | A1 | 2/2022 | Schmitt et al. |
| 2022/0039671 | A1 | 2/2022 | Fahey |
| 2022/0039833 | A1 | 2/2022 | Thai et al. |
| 2022/0088355 | A1 | 3/2022 | Rabito et al. |
| 2022/0096087 | A1 | 3/2022 | Valdez |
| 2022/0110679 | A1 | 4/2022 | Wang et al. |
| 2022/0142652 | A1 | 5/2022 | Alexander et al. |
| 2022/0151784 | A1 | 5/2022 | Eigler et al. |
| 2022/0168015 | A1 | 6/2022 | Murray et al. |
| 2022/0184356 | A1 | 6/2022 | Nae et al. |
| 2022/0202443 | A1 | 6/2022 | Thai et al. |
| 2022/0203078 | A1 | 6/2022 | May |
| 2022/0211380 | A1 | 7/2022 | Pate |
| 2022/0218352 | A1 | 7/2022 | O'Halloran et al. |
| 2022/0218964 | A1 | 7/2022 | Fahey et al. |
| 2022/0241564 | A1 | 8/2022 | Shang et al. |
| 2022/0241565 | A1 | 8/2022 | Nae et al. |
| 2022/0257904 | A1 | 8/2022 | Passman et al. |
| 2022/0273279 | A1 | 9/2022 | Valdez et al. |
| 2022/0280160 | A1 | 9/2022 | Sharma |
| 2022/0280760 | A1 | 9/2022 | Thai et al. |
| 2022/0296865 | A1 | 9/2022 | Rafiee et al. |
| 2022/0313234 | A1 | 10/2022 | Mcnamara et al. |
| 2022/0323012 | A1 | 10/2022 | Pool et al. |
| 2022/0323196 | A1 | 10/2022 | Rafiee et al. |
| 2022/0346936 | A1 | 11/2022 | Scutti et al. |
| 2022/0347446 | A1 | 11/2022 | Fahey et al. |
| 2022/0370120 | A1 | 11/2022 | Yang et al. |
| 2022/0379100 | A1 | 12/2022 | Gutierrez et al. |
| 2022/0387009 | A1 | 12/2022 | Bukhdruker et al. |
| 2023/0099410 | A1 | 3/2023 | Primeaux |
| 2023/0165672 | A1 | 6/2023 | Fahey et al. |
| 2023/0181214 | A1 | 6/2023 | Vardi et al. |
| 2023/0191093 | A1 | 6/2023 | Nae et al. |
| 2023/0263949 | A1 | 8/2023 | Passman et al. |
| 2023/0285133 | A1 | 9/2023 | Eigler et al. |
| 2023/0330398 | A1 | 10/2023 | Nae et al. |

FOREIGN PATENT DOCUMENTS

| | | | | |
|---|---|---|---|---|
| WO | WO-2000016686 | A2 | 3/2000 | |
| WO | WO-2009006249 | A1 | 1/2009 | |
| WO | WO-2020123338 | A1 * | 6/2020 | ........... A61B 5/6862 |
| WO | 2020215090 | A1 | 10/2020 | |
| WO | 2021091566 | A1 | 5/2021 | |
| WO | 2022031317 | A1 | 2/2022 | |
| WO | 2022060630 | A1 | 3/2022 | |
| WO | 2022133070 | A1 | 6/2022 | |
| WO | 2022169865 | A1 | 8/2022 | |
| WO | 2022177737 | A1 | 8/2022 | |
| WO | 2022197454 | A1 | 9/2022 | |
| WO | 2022197455 | A1 | 9/2022 | |
| WO | 2022232133 | A1 | 11/2022 | |
| WO | 2022246158 | A1 | 11/2022 | |
| WO | 2022246166 | A1 | 11/2022 | |
| WO | 2022271473 | A1 | 12/2022 | |
| WO | 2023022883 | A1 | 2/2023 | |
| WO | 2023027926 | A1 | 3/2023 | |
| WO | 2023079498 | A1 | 5/2023 | |
| WO | 2023081127 | A1 | 5/2023 | |
| WO | 2023081129 | A1 | 5/2023 | |
| WO | 2023154235 | A1 | 8/2023 | |
| WO | 2023154308 | A1 | 8/2023 | |
| WO | 2023172435 | A1 | 9/2023 | |
| WO | 2023172436 | A1 | 9/2023 | |
| WO | 2023196243 | A1 | 10/2023 | |
| WO | 2023239784 | A1 | 12/2023 | |
| WO | 2023239785 | A1 | 12/2023 | |
| WO | 2023239788 | A2 | 12/2023 | |

OTHER PUBLICATIONS

Kong, et al.—Creation Of An Intra-atrial Communication With A New Amplatzer Shunt Prosthesis, Catheterization and Cardiovascular Interventions 56:267-271 (2002).

P.K. Kong, et al., Title: Unroofed Coronary Sinus and Persistent Left Superior Vena Cava, The European Society of Cardiology, 2006, pp. 398401.

Ruebben et al., "Arteriovenous fistulas induced by femoral arterial catheterization: percuntaneous treatment," Radiology, 209:729, 1998.

Vandhana Scheller, et al., Title: Coronary Sinus to Left Atrial Communication, Case Report in Medicine, Ohio Heart and Vascular Center, vol. 2009, Article ID 790715, pp. 13.

* cited by examiner

SENSOR STABILIZER

CROSS-REFERENCE TO RELATED APPLICATIONS

This application claims the benefit of PCT/US21/12799, filed Jan. 8, 2021, which claim priority to U.S. Provisional Patent Application No. 63/060,333, filed on Aug. 3, 2020, the entire contents of each of which are hereby incorporated by reference.

BACKGROUND

Field

The present disclosure generally relates to the field of medical devices and procedures.

Description of Related Art

Certain physiological parameters associated with chambers of the heart, such as fluid pressure and blood flow, can have an impact on patient health prospects. In particular, high cardiac fluid pressure can lead to heart failure, embolism formation, and/or other complications in some patients. Therefore, information relating to physiological conditions, such as pressure, in one or more chambers of the heart can be beneficial.

SUMMARY

Described herein are one or more methods and/or devices to facilitate monitoring of physiological parameter(s) using certain sensor devices, as well as stabilizer mechanisms to facilitate stabilization of implanted sensor devices.

In some implementations, the present disclosure relates to a sensor-retention structure comprising a sensor-support arm configured to hold a sensor device and a stabilizer structure associated with the sensor-support arm and configured to project away from the sensor-support arm and provide stabilizing support for the sensor-support arm.

The stabilizer structure can comprise an elongate leg portion, an end portion, and a base portion that is integrated with the sensor-support arm. The stabilizer structure can be configured to bend at the base portion to cause the end portion of the stabilizer structure to project away from a distal end of the sensor-support arm. In some embodiments, the stabilizer structure is configured to bend at the base portion to cause the end portion of the stabilizer structure to project away from a proximal end of the sensor-support arm. The end portion of the stabilizer structure have an atraumatic coating disposed over at least a portion thereof. In some embodiments, the end portion of the stabilizer structure comprises two feet configured to be bent in opposite directions. The end portion can comprise a foot portion having a width at one or more portions thereof that is greater than a width of the elongate leg portion. In some embodiments, the end portion comprises a foot portion that is configured to deflect at an angle relative to the elongate leg portion to provide a tissue-contact surface.

The stabilizer structure may comprise a first leg and a second leg. For example, the first leg and the second leg can be relatively oriented in parallel. In some embodiments, the first leg and the second leg are angled relative to one another.

In some implementations, the present disclosure relates to a method of deploying a sensor implant device. The method comprises implanting an implant structure in a tissue wall, the implant structure including a sensor-support member configured to retain a sensor device and projecting a distal portion of a stabilizer form associated with the sensor-support member away from the sensor-support member and towards the tissue wall.

The method may further comprise stabilizing the sensor-support member with respect to an angle of the sensor-support member relative to a surface of the tissue wall. In some implementations, the method further comprises deflecting an end portion of the stabilizer form to provide a tissue-contact structure. In some implementations, the stabilizer form comprises shape-memory material and said projecting the distal portion of the stabilizer form involves deploying the implant structure from a delivery system and allowing the shape-memory material to cause the stabilizer form to bend at a base thereof to deflect the stabilizer form away from the sensor-support member.

In some implementations, the present disclosure relates to a method of retracting a sensor stabilizer. The method comprises providing a sensor implant device including a sensor-support structure and a stabilizer member including a suture-engagement feature, engaging a suture with the suture-engagement feature, implanting the sensor implant device in a tissue wall, deploying the stabilizer member at least in part by projecting at least a portion of the stabilizer member away from the sensor-support structure, and pulling one or more portions of the suture to thereby pull the stabilizer member into alignment with the sensor-support structure.

The suture-engagement feature may comprise an aperture associated with an end portion of the stabilizer member. In some implementations, the method further comprises pulling a suture tail of the suture proximally through a delivery system associated with the sensor implant device to withdraw the suture from the sensor implant device. The method may further comprise advancing a delivery catheter to the tissue wall, the delivery catheter having disposed therein a plurality of suture tail portions of the suture. In some implementations, the tissue wall is a wall separating a coronary sinus from a left ventricle of a heart.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the inventions. In addition, various features of different disclosed embodiments can be combined to form additional embodiments, which are part of this disclosure. Throughout the drawings, reference numbers may be reused to indicate correspondence between reference elements.

FIGS. 20-1 and 20-2 are a flow diagram illustrating a process for deploying and retracting a sensor stabilizer in accordance with one or more embodiments.

FIGS. 21-1 and 21-2 provide images of cardiac anatomy and certain devices/systems corresponding to operations associated with the process of FIGS. 20-1 and 20-2 in accordance with one or more embodiments.

DETAILED DESCRIPTION

The headings provided herein are for convenience only and do not necessarily affect the scope or meaning of the claimed inventive subject matter. The present disclosure relates to systems, devices, and methods for stabilizing sensor devices configured to be implanted in the body (e.g., heart). To such end, one or more stabilizers may be implemented to provide stabilizing contact/support between a sensor holder/retention structure and a tissue wall or other anatomy.

Although certain preferred embodiments and examples are disclosed below, inventive subject matter extends beyond the specifically disclosed embodiments to other alternative embodiments and/or uses, and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The following includes a general description of human cardiac anatomy that is relevant to certain inventive features and embodiments disclosed herein and is included to provide context for certain aspects of the present disclosure. In humans and other vertebrate animals, the heart generally comprises a muscular organ having four pumping chambers, wherein the flow of blood between the pumping chambers is at least partially controlled by various heart valves, namely, the aortic, mitral (or bicuspid), tricuspid, and pulmonary valves. The valves may be configured to open and close in response to a pressure gradient present during various stages of the cardiac cycle (e.g., relaxation and contraction) to at least partially control the flow of blood to a respective region of the heart and/or to associated blood vessels (e.g., pulmonary, aorta, etc.).

Figure 1A:
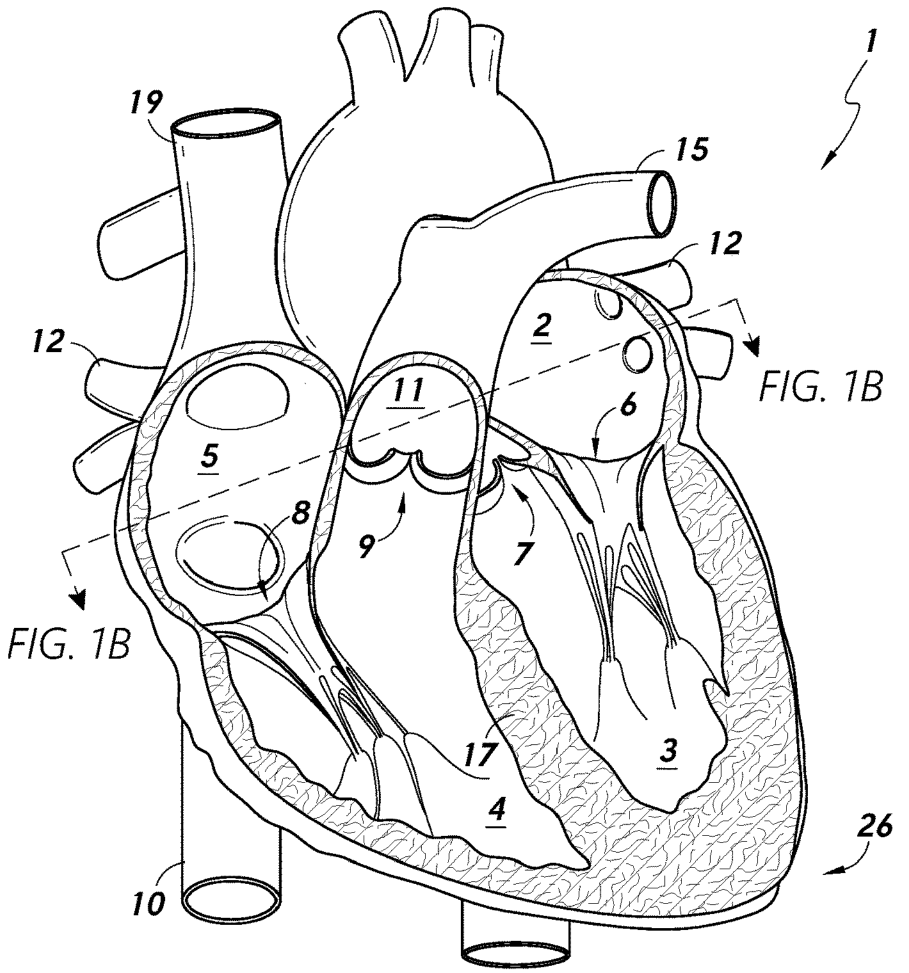
FIG. 1A shows a cross-sectional view of an example human heart.
Figure 1B:
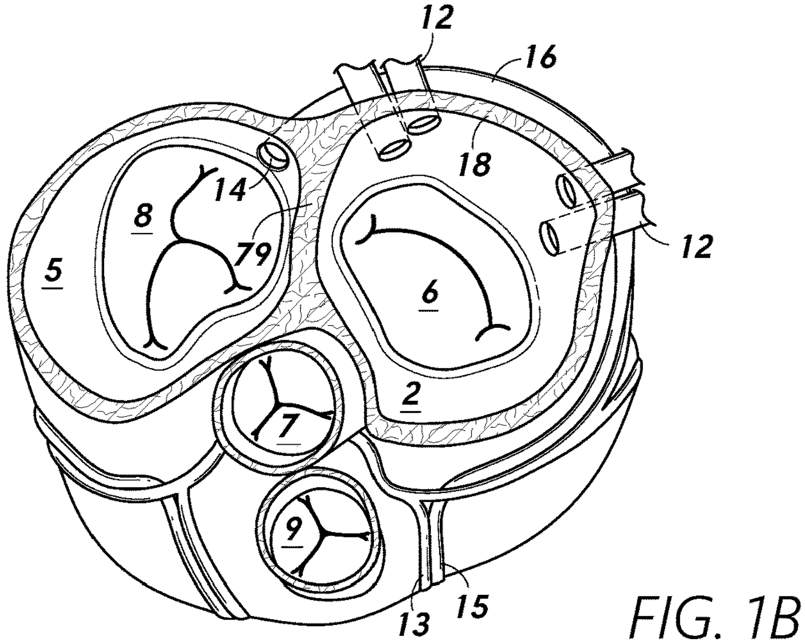
FIG. 1B shows a top-down atrial cross-sectional view of a human heart.

FIGS. 1A and 1B illustrate vertical and horizontal cross-sectional views, respectively, of an example heart 1 having various features/anatomy relevant to certain aspects of the present inventive disclosure. The heart 1 includes four chambers, namely the left ventricle 3, the left atrium 2, the right ventricle 4, and the right atrium 5. A wall of muscle, referred to as the septum, separates the left-side chambers from the right-side chambers. In particular, an atrial septum wall portion 79 (referred to herein as the "atrial septum," "interatrial septum," or "septum") separates the left atrium 2 from the right atrium 5, whereas a ventricular septum wall portion 17 (referred to herein as the "ventricular septum," "interventricular septum," or "septum") separates the left ventricle 3 from the right ventricle 4. The inferior tip 19 of the heart 1 is referred to as the apex and is generally located on the midclavicular line, in the fifth intercostal space. The apex 19 can be considered part of the greater apical region 39 identified in the drawings.

The left ventricle 3 is the primary pumping chamber of the heart 1. A healthy left ventricle is generally conical or apical in shape, in that it is longer (along a longitudinal axis extending in a direction from the aortic valve 7 (not shown in FIG. 1) to the apex 19) than it is wide (along a transverse axis extending between opposing walls 25, 26 at the widest point of the left ventricle) and descends from a base 15 with a decreasing cross-sectional diameter and/or circumference to the point or apex 19. Generally, the apical region 39 of the heart is a bottom region of the heart that is within the left and/or right ventricular region(s) but is distal to the mitral 6 and tricuspid 8 valves and disposed toward the tip 19 of the heart.

The pumping of blood from the left ventricle 3 is accomplished by a squeezing motion and a twisting or torsional motion. The squeezing motion occurs between the lateral wall 14 of the left ventricle 3 and the septum 17. The twisting motion is a result of heart muscle fibers that extend in a circular or spiral direction around the heart. When these fibers contract, they produce a gradient of angular displacements of the myocardium from the apex 19 to the base 15 about the longitudinal axis of the heart. The resultant force vectors extend at angles from about 30-60 degrees to the flow of blood through the aortic valve 7. The contraction of the heart is manifested as a counterclockwise rotation of the apex 19 relative to the base 15 when viewed from the apex 19. The contractions of the heart, in connection with the filling volumes of the left atrium 2 and ventricle 3, respectively, can result in relatively high fluid pressures in the left side of the heart at least during certain phase(s) of the cardiac cycle, the results of which are discussed in detail below.

The four valves of the heart aid the circulation of blood in the heart. The tricuspid valve 8 separates the right atrium 5 from the right ventricle 4. The tricuspid valve 8 generally has three cusps or leaflets and advantageously closes during ventricular contraction (i.e., systole) and opens during ventricular expansion (i.e., diastole). The pulmonary valve 9 separates the right ventricle 4 from the pulmonary artery 11 and generally is configured to open during systole so that blood may be pumped toward the lungs from the right ventricle 4, and close during diastole to prevent blood from leaking back into the right ventricle 4 from the pulmonary artery. The pulmonary valve 9 generally has three cusps/leaflets. The mitral valve 6 generally has two cusps/leaflets and separates the left atrium 2 from the left ventricle 3. The mitral valve 6 may generally be configured to open during diastole so that blood in the left atrium 2 can flow into the left ventricle 3, and close during diastole to prevent blood from leaking back into the left atrium 2. The aortic valve 7 separates the left ventricle 3 from the aorta 12. The aortic valve 7 is configured to open during systole to allow blood leaving the left ventricle 3 to enter the aorta 12, and close during diastole to prevent blood from leaking back into the left ventricle 3.

The atrioventricular (i.e., mitral and tricuspid) heart valves are generally associated with a sub-valvular apparatus, including a collection of chordae tendineae and papillary muscles securing the leaflets of the respective valves to promote and/or facilitate proper coaptation of the valve leaflets and prevent prolapse thereof. The papillary muscles, for example, may generally comprise finger-like projections from the ventricle wall. Surrounding the ventricles (3, 4) are a number of arteries 13 that supply oxygenated blood to the heart muscle and a number of veins 15 that return the blood from the heart muscle to the right atrium 5 via the coronary sinus 16 (see FIG. 1B). The coronary sinus 16 is a relatively large vein that extends generally around the upper portion of the left ventricle 3 and provides a return conduit for blood returning to the right atrium 5. A wall of muscle 18 separates the coronary sinus 16 from the left atrium. The coronary sinus 16 terminates at the coronary ostium 14, through which the blood enters the right atrium.

The primary roles of the left atrium 2 are to act as a holding chamber for blood returning from the lungs (not shown) and to act as a pump to transport blood to other areas of the heart. The left atrium 2 receives oxygenated blood from the lungs via the pulmonary veins 12. The oxygenated blood that is collected from the pulmonary veins 12 in the left atrium 2 enters the left ventricle 3 through the mitral valve 6. In some patients, the walls of the left atrium 2 are slightly thicker than the walls of the right atrium 5. Deoxygenated blood enters the right atrium 5 through the inferior 29 and superior 19 venae cavae. The right side of the heart then pumps this deoxygenated blood into the pulmonary arteries around the lungs. There, fresh oxygen enters the blood stream, and the blood moves to the left side of the heart via a network of pulmonary veins ultimately terminating at the left atrium 2, as shown. The ostia of the pulmonary veins 12 are generally located at or near the posterior left atrial wall of the left atrium 2.

Cardiac Pressure Monitoring for Prevention and Treatment of Heart Failure

As referenced above, certain physiological conditions or parameters associated with the cardiac anatomy can impact the health of a patient. For example, congestive heart failure is a condition associated with the relatively slow movement of blood through the heart and/or body, which causes the fluid pressure in one or more chambers of the heart to increase. As a result, the heart does not pump sufficient oxygen to meet the body's needs. The various chambers of the heart may respond to pressure increases by stretching to hold more blood to pump through the body or by becoming relatively stiff and/or thickened. The walls of the heart can eventually weaken and become unable to pump as efficiently. In some cases, the kidneys may respond to cardiac inefficiency by causing the body to retain fluid. Fluid build-up in arms, legs, ankles, feet, lungs, and/or other organs can cause the body to become congested, which is referred to as congestive heart failure. Acute decompensated congestive heart failure is a leading cause of morbidity and mortality, and therefore treatment and/or prevention of congestive heart failure is a significant concern in medical care.

The treatment and/or prevention of heart failure (e.g., congestive heart failure) can advantageously involve the monitoring of pressure in one or more chambers or regions of the heart or other anatomy, such as monitoring of left atrial pressure. As described above, pressure buildup in one or more chambers or areas of the heart can be associated with congestive heart failure. However, without direct or indirect monitoring of cardiac pressure (e.g., left atrial pressure, it can be difficult to infer, determine, or predict the presence or occurrence of congestive heart failure. For example, treatments or approaches not involving direct or indirect pressure monitoring may involve measuring or observing other present physiological conditions of the patient, such as measuring body weight, thoracic impedance, right heart catheterization, or the like.

In some solutions, pulmonary capillary wedge pressure can be measured as a surrogate of left atrial pressure. For example, a pressure sensor may be disposed or implanted in the pulmonary artery, and readings associated therewith may be used as a surrogate for left atrial pressure. However, with respect to catheter-based pressure measurement in the pulmonary artery or certain other chambers or regions of the heart, use of invasive catheters may be required to maintain such pressure sensors, which may be uncomfortable or difficult to implement. Furthermore, certain lung-related conditions may affect pressure readings in the pulmonary artery, such that the correlation between pulmonary artery pressure and left atrial pressure may be undesirably attenuated. As an alternative to pulmonary artery pressure measurement, pressure measurements in the right ventricle outflow tract may relate to left atrial pressure as well. However, the correlation between such pressure readings and left atrial pressure may not be sufficiently strong to be utilized in congestive heart failure diagnostics, prevention, and/or treatment.

Additional solutions may be implemented for deriving or inferring left atrial pressure. For example, the E/A ratio, which is a marker of the function of the left ventricle of the heart representing the ratio of peak velocity blood flow from gravity in early diastole (the E wave) to peak velocity flow in late diastole caused by atrial contraction (the A wave), can be used as a surrogate for measuring left atrial pressure. The E/A ratio may be determined using echocardiography or other imaging technology; generally, abnormalities in the E/A ratio may suggest that the left ventricle cannot fill with blood properly in the period between contractions, which may lead to symptoms of heart failure, as explained above. However, E/A ratio determination generally does not provide absolute pressure measurement values.

Various methods for identifying and/or treating congestive heart failure involve the observation of worsening congestive heart failure symptoms and/or changes in body weight. However, such signs may appear relatively late and/or be relatively unreliable. For example, daily body-weight measurements may vary significantly (e.g., up to 9% or more) and may be unreliable in signaling heart-related complications. Furthermore, treatments guided by monitoring signs, symptoms, weight, and/or other biomarkers have not been shown to substantially improve clinical outcomes. In addition, for patients that have been discharged, such treatments may necessitate remote telemedicine systems.

The present disclosure provides systems, devices, and methods for guiding the administration of medication relating to the treatment of congestive heart failure at least in part by directly monitoring pressure in the left atrium, or other chamber or vessel for which pressure measurements are indicative of left atrial pressure, in order to reduce hospital readmissions, morbidity, and/or otherwise improve the health prospects of patient at risk of heart failure.

Cardiac pressure monitoring in accordance with embodiments of the present disclosure may provide a proactive intervention mechanism for preventing or treating congestive heart failure. Generally, increases in ventricular filling pressures associated with diastolic and/or systolic heart failure can occur prior to the occurrence of symptoms that lead to hospitalization. For example, cardiac pressure indicators may present weeks prior to hospitalization for some patients. Therefore, pressure monitoring systems in accordance with embodiments of the present disclosure may advantageously be implemented to reduce instances of hospitalization by guiding the appropriate or desired titration and/or administration of medications before the onset of heart failure.

Dyspnea represents a cardiac pressure indicator characterized by shortness of breath or the feeling that one cannot breathe well enough. Dyspnea may result from elevated atrial pressure, which may cause fluid buildup in the lungs from pressure back-up. Pathological dyspnea can result from congestive heart failure. However, a significant amount of time may elapse between the time of initial pressure elevation and the onset of dyspnea, and therefore symptoms of dyspnea may not provide sufficiently-early signaling of elevated atrial pressure. By monitoring pressure directly according to embodiments of the present disclosure, normal ventricular filling pressures may advantageously be maintained, thereby preventing or reducing effects of heart failure, such as dyspnea.

Figure 2:
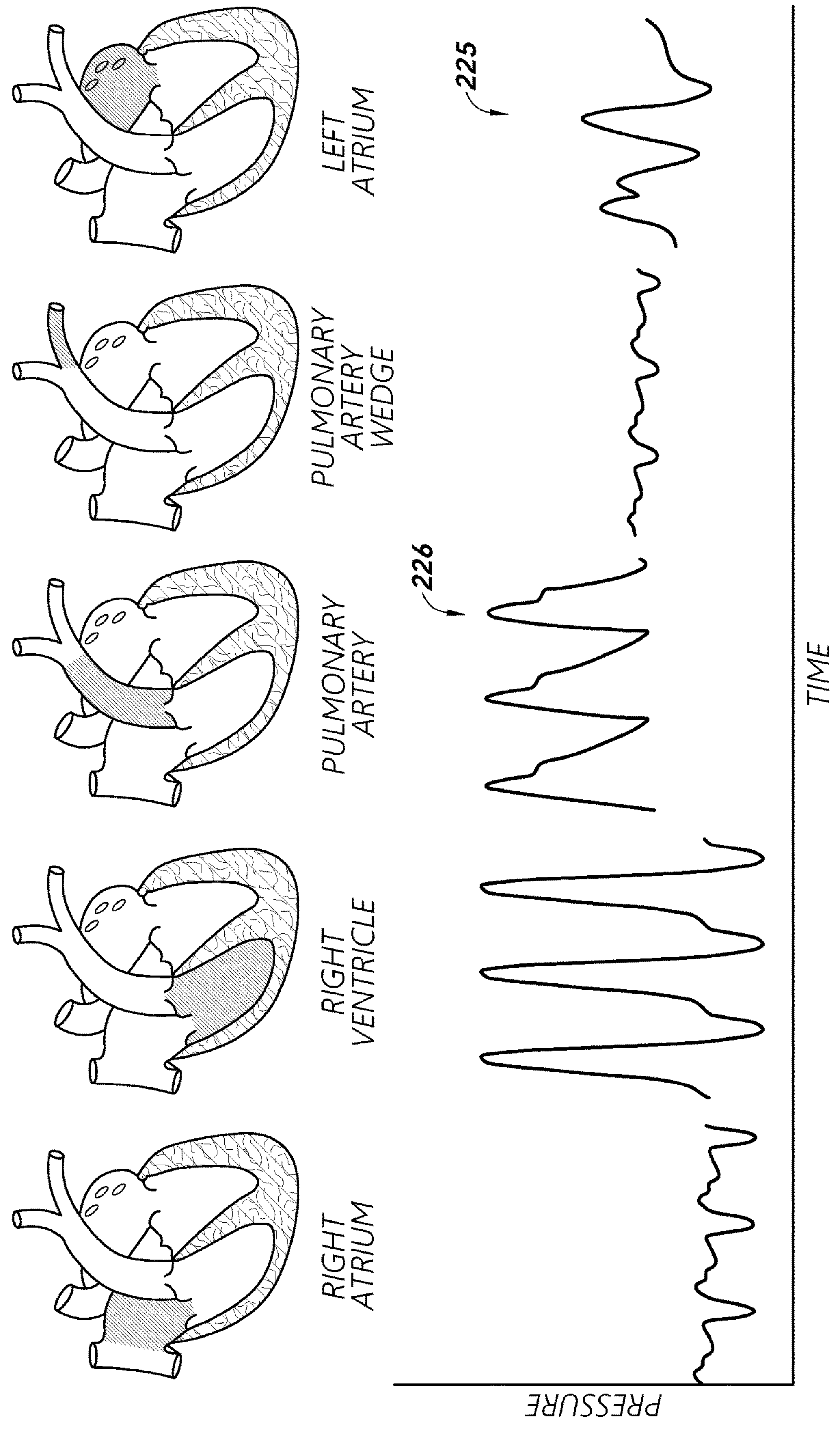
FIG. 2 illustrates example pressure waveforms associated with various chambers and vessels of the heart according to one or more embodiments.

As referenced above, with respect to cardiac pressures, pressure elevation in the left atrium may be particularly correlated with heart failure. FIG. 2 illustrates example pressure waveforms associated with various chambers and vessels of the heart according to one or more embodiments. The various waveforms illustrated in FIG. 2 may represent waveforms obtained using right heart catheterization to advance one or more pressure sensors to the respective illustrated and labeled chambers or vessels of the heart. As illustrated in FIG. 2, the waveform 225, which represents left atrial pressure, may be considered to provide the best feedback for early detection of congestive heart failure. Furthermore, there may generally be a relatively strong correlation between increases and left atrial pressure and pulmonary congestion.

Left atrial pressure may generally correlate well with left ventricular end-diastolic pressure. However, although left atrial pressure and end-diastolic pulmonary artery pressure can have a significant correlation, such correlation may be weakened when the pulmonary vascular resistance becomes elevated. That is, pulmonary artery pressure generally fails to correlate adequately with left ventricular end-diastolic pressure in the presence of a variety of acute conditions, which may include certain patients with congestive heart failure. For example, pulmonary-retention, which affects approximately 35-83% of patients with heart failure, can affect the reliability of pulmonary artery pressure measurement for estimating left-sided filling pressure. Therefore, pulmonary artery pressure measurement alone, as represented by the waveform 326, may be an insufficient or inaccurate indicator of left ventricular end-diastolic pressure, particularly for patients with co-morbidities, such as lung disease and/or thromboembolism. Left atrial pressure may further be correlated at least partially with the presence and/or degree of mitral regurgitation.

Left atrial pressure readings may be relatively less likely to be distorted or affected by other conditions, such as respiratory conditions or the like, compared to the other pressure waveforms shown in FIG. 2. Generally, left atrial pressure may be significantly predictive of heart failure, such as up two weeks before manifestation of heart failure. For example, increases in left atrial pressure, and both diastolic and systolic heart failure, may occur weeks prior to hospitalization, and therefore knowledge of such increases may be used to predict the onset of congestive heart failure.

Cardiac pressure monitoring, such as left atrial pressure monitoring, can provide a mechanism to guide administration of medication to treat and/or prevent congestive heart failure. Such treatments may advantageously reduce hospital readmissions and morbidity, as well as provide other benefits. An implanted pressure sensor in accordance with embodiments of the present disclosure may be used to predict heart failure up two weeks or more before the manifestation of symptoms or markers of heart failure (e.g., dyspnea). When heart failure predictors are recognized using cardiac pressure sensor embodiments in accordance with the present disclosure, certain prophylactic measures may be implemented, including medication intervention, such as modification to a patient's medication regimen, which may help prevent or reduce the effects of cardiac dysfunction. Direct pressure measurement in the left atrium can advantageously provide an accurate indicator of pressure buildup that may lead to heart failure or other complications. For example, trends of atrial pressure elevation may be analyzed or used to determine or predict the onset of cardiac dysfunction, wherein drug or other therapy may be augmented to cause reduction in pressure and prevent or reduce further complications.

Figure 3:
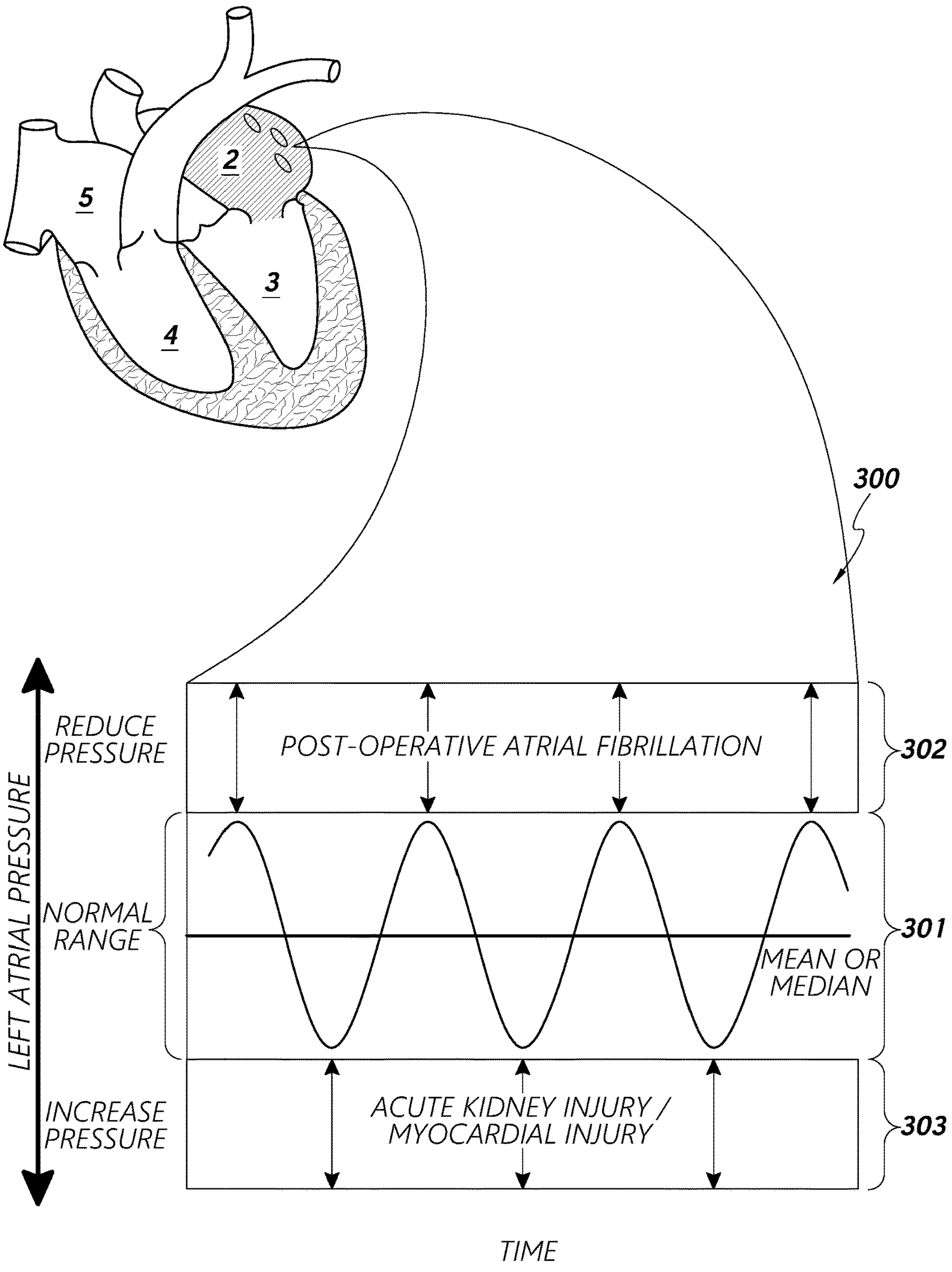
FIG. 3 illustrates a graph showing left atrial pressure ranges.

FIG. 3 illustrates a graph 300 showing left atrial pressure ranges including a normal range 301 of left atrial pressure that is not generally associated with substantial risk of postoperative atrial fibrillation, acute kidney injury, myocardial injury, heart failure and/or other health conditions. Embodiments of the present disclosure provide systems, devices, and methods for determining, using readings from sensor implant devices including sensor-retention structures and sensor stabilizer structures, whether a patient's left atrial pressure is within the normal range 301, above the normal range 303, or below the normal range 302. For detected left atrial pressure above the normal range, which may be correlated with an increased risk of heart failure, embodiments of the present disclosure as described in detail below can inform efforts to reduce the left atrial pressure until it is brought within the normal range 301. Furthermore, for detected left atrial pressure that is below the normal range 301, which may be correlated with increased risks of acute kidney injury, myocardial injury, and/or other health complications, embodiments of the present disclosure as described in detail below can serve to facilitate efforts to increase the left atrial pressure to bring the pressure level within the normal range 301.

Implant Devices with Associated Sensors and Sensor Stabilizers

Figure 4:
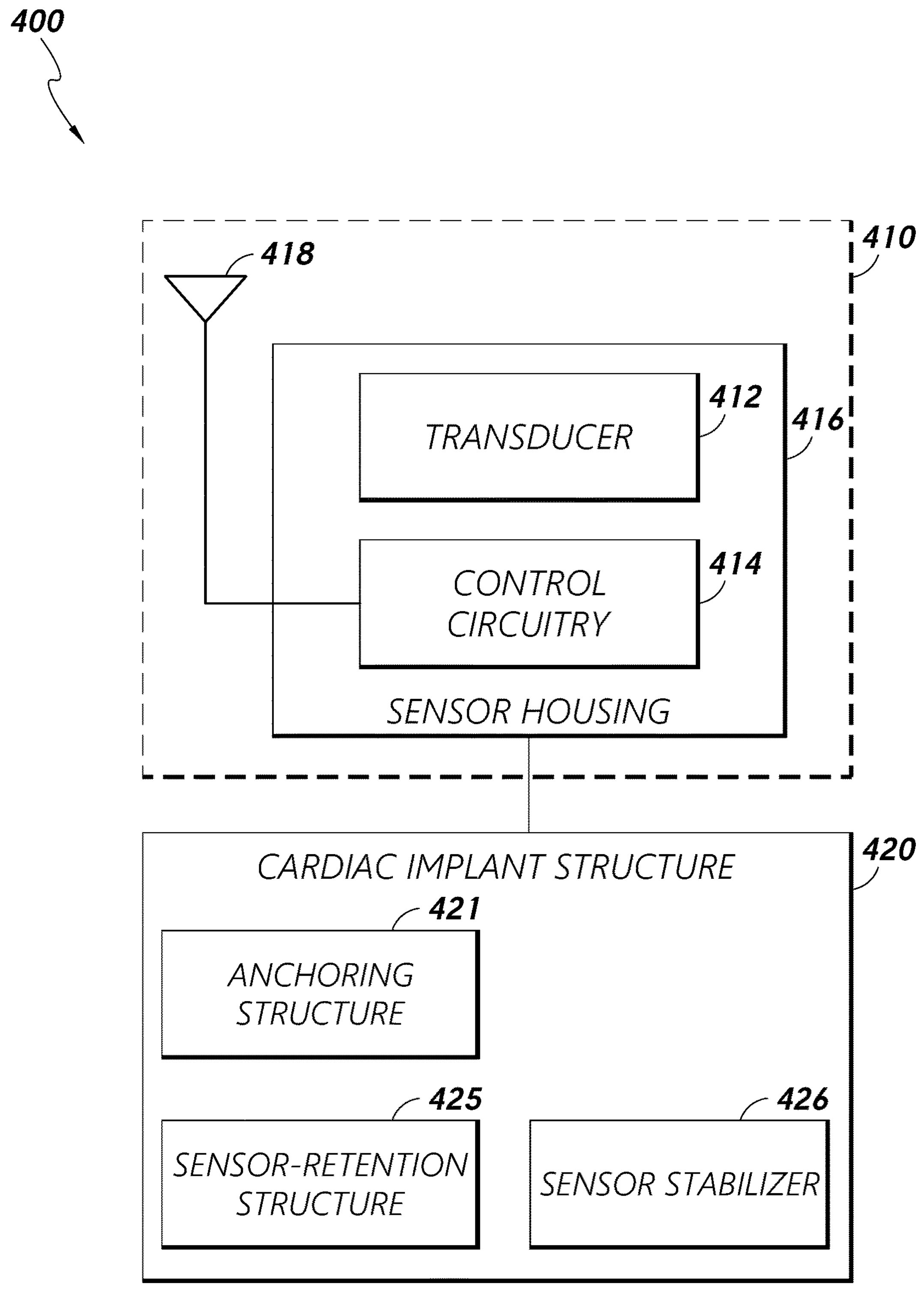
FIG. 4 is a block diagram representing an implant device in accordance with one or more embodiments.

In some implementations, the present disclosure relates to sensors associated or integrated with cardiac shunts or other implant devices/structures. Such integrated devices may be used to provide controlled and/or more effective therapies for treating and preventing heart failure and/or other health complications related to cardiac function. FIG. 4 is a block diagram illustrating an implant device 400 comprising a cardiac implant structure 420, which may comprise a shunt-type structure, as described in detail herein, or any other type of implant structure. The cardiac implant structure 420 can include certain anchoring structure 421 for anchoring the implant device 400 in place in the implant location/position. For example, the anchoring structure 421 may comprise one or more arms, barbs, sutures, suture-engagement features, corkscrew-type or other tissue-engagement features, or the like.

In some embodiments, the cardiac implant structure 420 is physically integrated with and/or connected to a sensor device 410. The sensor device 410 may be, for example, a pressure sensor, or other type of sensor. In some embodiments, the sensor 410 comprises one or more transducers 412, such as one or more pressure transducers, as well as certain control circuitry 414, which may be embodied in, for example, an application-specific integrated circuit (ASIC). The sensor device 410 can have a generally cylindrical shape with respect to one or more portions thereof. The sensor device 410 can be secured to the implant structure 420 by certain sensor-retention structure 425, examples of which are disclosed in detail herein. The sensor device 410 and/or sensor-retention structure 425 can be secured/stabilized using a stabilizer 426, which may be integrated or associated with the sensor-retention structure 425 or another component of the sensor implant device 400.

The control circuitry 414 may be configured to process signals received from the transducer 412 and/or communicate signals wirelessly through biological tissue using the antenna 418. The antenna 418 may comprise one or more coils or loops of conductive material, such as copper wire or the like. In some embodiments, at least a portion of the transducer 412, control circuitry 414, and/or the antenna 418 are at least partially disposed or contained within a sensor housing 416, which may comprise any type of material, and may advantageously be at least partially hermetically sealed. For example, the housing 416 may comprise glass or other rigid material in some embodiments, which may provide mechanical stability and/or protection for the components housed therein. In some embodiments, the housing 416 is at least partially flexible. For example, the housing may comprise polymer or other flexible structure/material, which may advantageously allow for folding, bending, or collapsing of the sensor 420 to allow for transportation thereof through a catheter or other introducing means. In some embodiments, the sensor housing 416 is at least partially cylindrical in shape.

The transducer 412 may comprise any type of sensor means or mechanism. For example, the transducer 412 may be a force-collector-type pressure sensor. In some embodiments, the transducer 412 comprises a diaphragm, piston, bourdon tube, bellows, or other strain- or deflection-measuring component(s) to measure strain or deflection applied over an area/surface thereof. The transducer 412 may be associated with the housing 46, such that at least a portion thereof is contained within or attached to the housing 46. The term "associated with" is used herein according to its broad and ordinary meaning. With respect to sensor devices/ components being "associated with" a shunt or other implant structure, such terminology may refer to a sensor device or component being physically coupled, attached, or connected to, or integrated with, the implant structure. That is, where a first feature, element, component, device, or member is described as being "associated with" a second feature, element, component, device, or member, such description should be understood as indicating that the first feature, element, component, device, or member is physically coupled, attached, or connected to, integrated with, embedded at least partially within, or otherwise physically related to the second feature, element, component, device, or member, whether directly or indirectly.

In some embodiments, the transducer 412 comprises or is a component of a piezoresistive strain gauge, which may be configured to use a bonded or formed strain gauge to detect strain due to applied pressure, wherein resistance increases as pressure deforms the component/material. The transducer 412 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 412 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon, and the like. In some embodiments, the transducer 412 comprises or is a component of an electromagnetic pressure sensor, which may be configured to measure the displacement of a diaphragm by means of changes in inductance, linear variable displacement transducer (LVDT) functionality, Hall Effect, or eddy current sensing. In some embodiments, the transducer 412 comprises or is a component of a piezoelectric strain sensor. For example, such a sensor may determine strain (e.g., pressure) on a sensing mechanism based on the piezoelectric effect in certain materials, such as quartz.

In some embodiments, the transducer 412 comprises or is a component of a strain gauge. For example, a strain gauge embodiment may comprise a pressure sensitive element on or associated with an exposed surface of the transducer 412. In some embodiments, a metal strain gauge is adhered to a surface of the sensor, or a thin-film gauge may be applied on the sensor by sputtering or other technique. The measuring element or mechanism may comprise a diaphragm or metal foil. The transducer 412 may comprise any other type of sensor or pressure sensor, such as optical, potentiometric, resonant, thermal, ionization, or other types of strain or pressure sensors.

Sensor Implant Systems

Embodiments of the present disclosure provide systems, devices, and methods for determining and/or monitoring fluid pressure and/or other physiological parameters or conditions in the left atrium using one or more implantable sensor devices, such as permanently implanted sensor devices. By placing a permanent sensor monitor device directly in the left atrium, embodiments of the present disclosure can advantageously allow physicians and/or technicians to gather real-time cardiac information, including left atrial pressure values and/or other valuable cardiac parameters.

Figure 5:
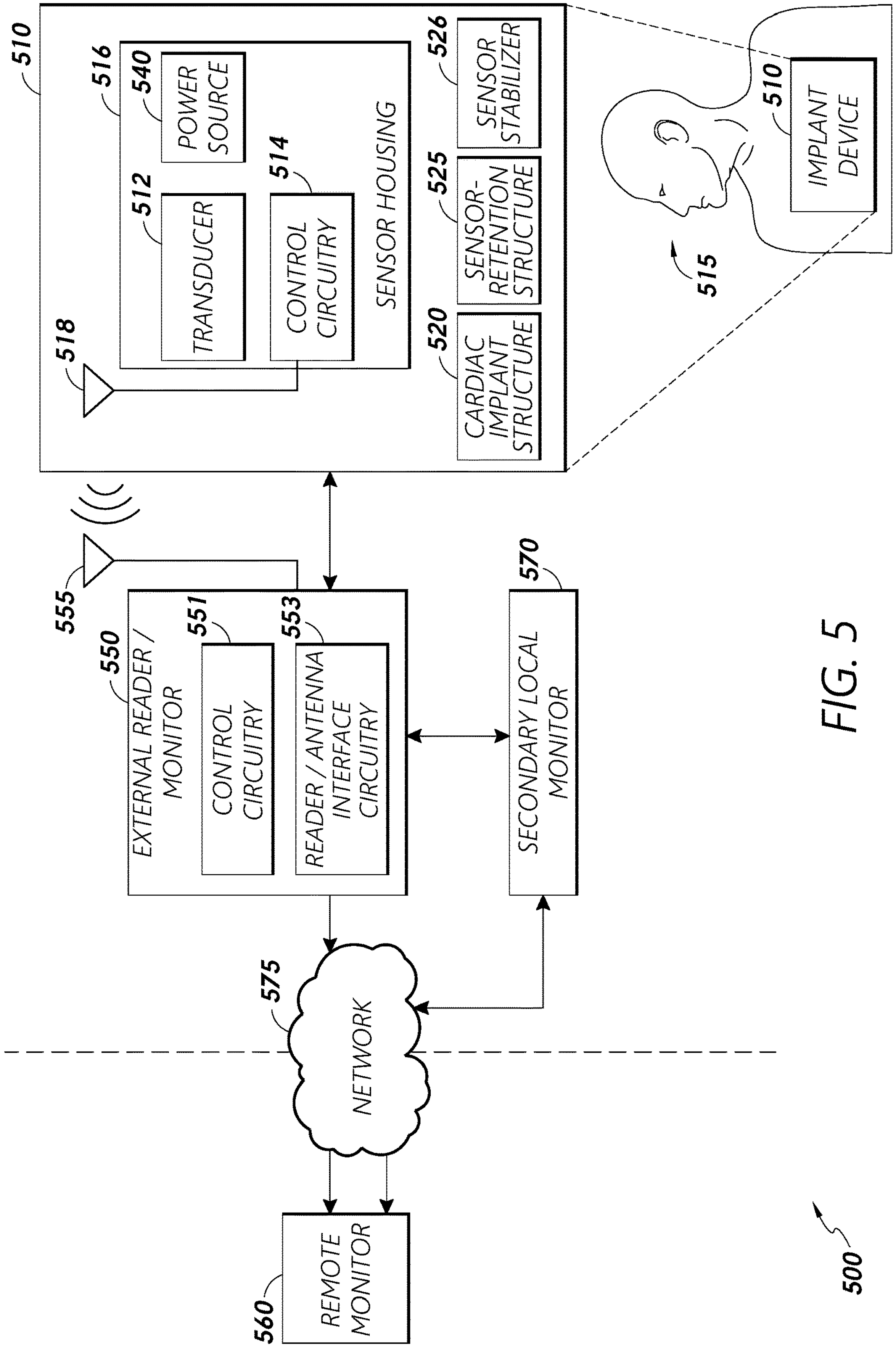
FIG. 5 shows a system for monitoring physiological parameter(s) according to one or more embodiments.

Disclosed solutions for implanting and maintaining sensor implant devices including certain stabilizer features may be implemented in connection with a pressure-monitoring system. FIG. 5 illustrates a system 500 for monitoring pressure and/or other parameter(s) associated with a patient 515 in accordance with embodiments of the present disclosure. Although the description of FIG. 5 and other embodiments herein is generally presented in the context of pressure monitoring, it should be understood that description of pressure sensing and pressure sensor stabilizing herein is applicable to sensing/stabilization of other types of sensors and sensing of other types of physiological parameters, wherein sensor devices used for such purposes are stabilized using certain stabilizer features.

The patient 515 can have a pressure sensor implant device 510 implanted in, for example, the heart (not shown), or associated physiology, of the patient. For example, the sensor implant device 510 can be implanted at least partially within the left atrium of the patient's heart. The sensor implant device 510 can include one or more sensor transducers 512, such as one or more microelectromechanical system (MEMS) devices, such as MEMS pressure sensors, or the like.

In certain embodiments, the monitoring system 500 can comprise at least two subsystems, including an implantable internal subsystem or device 510 that includes the sensor transducer(s) 512 (e.g., MEMS pressure sensor(s)), as well as control circuitry 514 comprising one or more microcontroller(s), discrete electronic component(s), and one or more power and/or data transmitter(s) 518 (e.g., antennae coil). The monitoring system 500 can further include an external (e.g., non-implantable) subsystem that includes an external reader 550 (e.g., coil), which may include a wireless transceiver that is electrically and/or communicatively coupled to certain control circuitry. In certain embodiments, both the internal and external subsystems include a corresponding antenna for wireless communication and/or power delivery through patient tissue disposed therebetween. The sensor implant device 510 can be any type of implant device.

The term "control circuitry" is used herein according to its broad and ordinary meaning, and may refer to any collection of processors, processing circuitry, processing modules/units, chips, dies (e.g., semiconductor dies including come or more active and/or passive devices and/or connectivity circuitry), microprocessors, micro-controllers, digital signal processors, microcomputers, central processing units, field programmable gate arrays, programmable logic devices, state machines (e.g., hardware state machines), logic circuitry, analog circuitry, digital circuitry, and/or any device that manipulates signals (analog and/or digital) based on hard coating of the circuitry and/or operational instructions. Control circuitry referenced herein may further comprise one or more, storage devices, which may be embodied in a single memory device, a plurality of memory devices, and/or embedded circuitry of a device. Such data storage may comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware and/or software state machine, analog circuitry, digital circuitry, and/or logic circuitry, data storage device(s)/register(s) storing any associated operational instructions may be embedded within, or external to, the circuitry comprising the state machine, analog circuitry, digital circuitry, and/or logic circuitry.

Certain details of the sensor implant device 510 are illustrated in the enlarged block 510 shown. The sensor implant device 510 can comprise implant/anchor structure 520 as described herein. For example, the implant structure 520 can include one or more shunt-type implants/anchors for anchoring in a cardiac tissue wall, as described in greater detail below. The implant structure 520 can further comprise one or more arm structures that physically hold/secure the implant structure 520 to a tissue wall, for example. Although certain components are illustrated in FIG. 5 as part of the sensor implant device 510, it should be understood that the sensor implant device 510 may only comprise a subset of the illustrated components/modules and can comprise additional components/modules not illustrated. The sensor implant device 510 includes one or more sensor transducers 512, which can be configured to provide a response indicative of one or more physiological parameters of the patient 515, such as atrial pressure and/or volume. Although pressure transducers are described, the sensor transducer(s) 512 can comprise any suitable or desirable types of sensor transducer(s) for providing signals relating to physiological parameters or conditions associated with the sensor implant device 510.

The sensor transducer(s) 512 can comprise one or more MEMS sensors, optical sensors, piezoelectric sensors, electromagnetic sensors, strain sensors/gauges, accelerometers, gyroscopes, and/or other types of sensors, which can be positioned in the patient 515 to sense one or more parameters relevant to the health of the patient. The transducer 512 may be a force-collector-type pressure sensor. In some embodiments, the transducer 512 comprises a diaphragm, membrane, piston, bourdon tube, bellows, or other strain- or deflection-measuring component(s) to measure strain or deflection applied over an area/surface thereof. The transducer 512 may be associated with a sensor housing 516, such that at least a portion thereof is contained within, or attached to, the housing 516.

In some embodiments, the transducer 512 comprises or is a component of a piezoresistive strain gauge, which may be configured to use a bonded or formed strain gauge to detect strain due to applied pressure, wherein resistance increases as pressure deforms the component/material. The transducer 512 may incorporate any type of material, including but not limited to silicon (e.g., monocrystalline), polysilicon thin film, bonded metal foil, thick film, silicon-on-sapphire, sputtered thin film, and/or the like.

In some embodiments, the transducer 512 comprises or is a component of a capacitive pressure sensor including a diaphragm and pressure cavity configured to form a variable capacitor to detect strain due to pressure applied to the diaphragm. The capacitance of the capacitive pressure sensor may generally decrease as pressure deforms the diaphragm. The diaphragm may comprise any material(s), including but not limited to metal, ceramic, silicon or other semiconductor, and the like. In some embodiments, the transducer 512 comprises or is a component of an electromagnetic pressure sensor, which may be configured to measures the displacement of a diaphragm by means of changes in inductance, linear variable displacement transducer (LVDT) functionality, Hall Effect, or eddy current sensing. In some embodiments, the transducer 512 comprises or is a component of a piezoelectric strain sensor. For example, such a sensor may determine strain (e.g., pressure) on a sensing mechanism based on the piezoelectric effect in certain materials, such as quartz.

In some embodiments, the transducer 512 comprises or is a component of a strain gauge. For example, a strain gauge embodiment may comprise a pressure sensitive element on or associated with an exposed surface of the transducer 512. In some embodiments, a metal strain gauge is adhered to the sensor surface, or a thin-film gauge may be applied on the sensor by sputtering or other technique. The measuring element or mechanism may comprise a diaphragm or metal foil. The transducer 512 may comprise any other type of sensor or pressure sensor, such as optical, potentiometric, resonant, thermal, ionization, or other types of strain or pressure sensors.

In some embodiments, the transducer(s) 512 is/are electrically and/or communicatively coupled to the control circuitry 514, which may comprise one or more application-specific integrated circuit (ASIC) microcontrollers or chips. The control circuitry 514 can further include one or more discrete electronic components, such as tuning capacitors or the like.

In certain embodiments, the sensor transducer(s) 512 can be configured to generate electrical signals that can be wirelessly transmitted to a device outside the patient's body 515, such as the illustrated local external monitor system 550. In order to perform such wireless data transmission, the sensor implant device 510 can include radio frequency (RF) transmission circuitry, such as a signal processing circuitry and an antenna 518. The antenna 518 can comprise an internal antenna coil or other structure implanted within the patient. The control circuitry 514 may comprise any type of transducer circuitry configured to transmit an electromagnetic signal, wherein the signal can be radiated by the antenna 518, which may comprise one or more conductive wires, coils, plates, or the like. The control circuitry 514 of the sensor implant device 510 can comprise, for example, one or more chips or dies configured to perform some amount of processing on signals generated and/or transmitted using the device 510. However, due to size, cost, and/or other constraints, the sensor implant device 510 may not include independent processing capability in some embodiments.

The wireless signals generated by the sensor implant device 510 can be received by the local external monitor device or subsystem 550, which can include a transceiver module 553 configured to receive the wireless signal transmissions from the sensor implant device 510, which is disposed at least partially within the patient 515. The external local monitor 550 can receive the wireless signal transmissions and/or provide wireless power using an external antenna 555, such as a wand device. The transceiver 553 can include radio-frequency (RF) front-end circuitry configured to receive and amplify the signals from the sensor implant device 510, wherein such circuitry can include one or more filters (e.g., band-pass filters), amplifiers (e.g., low-noise amplifiers), analog-to-digital converters (ADC) and/or digital control interface circuitry, phase-locked loop (PLL) circuitry, signal mixers, or the like. The transceiver 553 can further be configured to transmit signals over a network 575 to a remote monitor subsystem or device 560. The RF circuitry of the transceiver 553 can further include one or more of digital-to-analog converter (DAC) circuitry, power amplifiers, low-pass filters, antenna switch modules, antennas or the like for treatment/processing of transmitted signals over the network 575 and/or for receiving signals from the sensor implant device 510. In certain embodiments, the local monitor 550 includes control circuitry 551 for performing processing of the signals received from the sensor implant device 510. The local monitor 550 can be configured to communicate with the network 575 according to a known network protocol, such as Ethernet, Wi-Fi, or the like. In certain embodiments, the local monitor 550 is a smartphone, laptop computer, or other mobile computing device, or any other type of computing device.

In certain embodiments, the sensor implant device 510 includes some amount of volatile and/or non-volatile data storage. For example, such data storage can comprise solid-state memory utilizing an array of floating-gate transistors, or the like. The control circuitry 514 may utilize data storage for storing sensed data collected over a period of time, wherein the stored data can be transmitted periodically to the local monitor 550 or another external subsystem. In certain embodiments, the sensor implant device 510 does not include any data storage. The control circuitry 514 is configured to facilitate wireless transmission of data generated by the sensor transducer(s) 512, or other data associated therewith. The control circuitry 514 may further be configured to receive input from one or more external subsystems, such as from the local monitor 550, or from a remote monitor 560 over, for example, the network 575. For example, the sensor implant device 510 may be configured to receive signals that at least partially control the operation of the sensor implant device 510, such as by activating/deactivating one or more components or sensors, or otherwise affecting operation or performance of the sensor implant device 510.

The one or more components of the sensor implant device 510 can be powered by one or more power sources 540. Due to size, cost and/or electrical complexity concerns, it may be desirable for the power source 540 to be relatively minimalistic in nature. For example, high-power driving voltages and/or currents in the sensor implant device 510 may adversely affect or interfere with operation of the heart or other anatomy associated with the implant device. In certain embodiments, the power source 540 is at least partially passive in nature, such that power can be received from an external source wirelessly by passive circuitry of the sensor implant device 510. Examples of wireless power transmission technologies that may be implemented include but are not limited to short-range or near-field wireless power transmission, or other electromagnetic coupling mechanism(s). For example, the local monitor 550 may serve as an initiator that actively generates an RF field that can provide power to the sensor implant device 510, thereby allowing the power circuitry of the implant device to take a relatively simple form factor. In certain embodiments, the power source 540 can be configured to harvest energy from environmental sources, such as fluid flow, motion, pressure, or the like. Additionally or alternatively, the power source 540 can comprise a battery, which can advantageously be configured to provide enough power as needed over the relevant monitoring period.

In some embodiments, the local monitor device 550 can serve as an intermediate communication device between the sensor implant device 510 and the remote monitor 560. The local monitor device 550 can be a dedicated external unit designed to communicate with the sensor implant device 510. For example, the local monitor device 550 can be a wearable communication device, or other device that can be readily disposed in proximity to the patient 515 and/or sensor implant device 510. The local monitor device 550 can be configured to continuously, periodically, or sporadically interrogate the sensor implant device 510 in order to extract or request sensor-based information therefrom. In certain embodiments, the local monitor 550 comprises a user interface, wherein a user can utilize the interface to view sensor data, request sensor data, or otherwise interact with the local monitor system 550 and/or sensor implant device 510.

The system 500 can include a secondary local monitor 570, which can be, for example, a desktop computer or other computing device configured to provide a monitoring station or interface for viewing and/or interacting with the monitored cardiac data. In an embodiment, the local monitor 550 can be a wearable device or other device or system configured to be disposed in close physical proximity to the patient and/or sensor implant device 510, wherein the local monitor 550 is primarily designed to receive/transmit signals to and/or from the sensor implant device 510 and provide such signals to the secondary local monitor 570 for viewing, processing, and/or manipulation thereof. The external local monitor system 550 can be configured to receive and/or process certain metadata from or associated with the sensor implant device 510, such as device ID or the like, which can also be provided over the data coupling from the sensor implant device 510.

The remote monitor subsystem 560 can be any type of computing device or collection of computing devices configured to receive, process and/or present monitor data received over the network 575 from the local monitor device 550, secondary local monitor 570, and/or sensor implant device 510. For example, the remote monitor subsystem 560 can advantageously be operated and/or controlled by a healthcare entity, such as a hospital, doctor, or other care entity associated with the patient 515.

In certain embodiments, the antenna 555 of the external monitor system 550 comprises an external coil antenna that is matched and/or tuned to be inductively paired with the antenna 518 of the internal implant 510. In some embodiments, the sensor implant device 510 is configured to receive wireless ultrasound power charging and/or data communication between from the external monitor system 550. As referenced above, the local external monitor 550 can comprise a wand or other hand-held reader.

In some embodiments, at least a portion of the transducer 512, control circuitry 514, power source 540 and/or the antenna 518 is at least partially disposed or contained within the sensor housing 516, which may comprise any type of material, and may advantageously be at least partially hermetically sealed. For example, the housing 516 may comprise glass or other rigid material in some embodiments, which may provide mechanical stability and/or protection for the components housed therein. In some embodiments, the housing 516 is at least partially flexible. For example, the housing may comprise polymer or other flexible structure/material, which may advantageously allow for folding, bending, or collapsing of the sensor 510 to allow for transportation thereof through a catheter or other percutaneous introducing means.

The sensor housing 516 can be secured to certain sensor-retention structure 525, which may be physically coupled to and/or integrated with the cardiac implant structure 520. For example, in some embodiments, the sensor-retention structure 525 is integrated with an arm component of the implant structure 520. The sensor-retention structure 525 may be stabilized against a tissue wall using one or more sensor stabilizer features 526, which may be coupled to and/or integrated with the sensor-retention structure 525. Therefore, the stabilizer(s) 526 can serve to stabilize the sensor housing 516 when implanted in the patient 515. The sensor stabilizer(s) 526 may be similar in certain respects to one or more of the embodiments disclosed herein relating to stabilizer features and structures.

The sensor implant device 510 may be implanted in any location in the body the patient 515. In some embodiments of the present disclosure, the sensor implant device 510 is advantageously implanted in the heart of the patient 515, such as in or near the left atrium of the heart, as described in detail herein. Placement of the sensor implant device 510 at least partially within the left atrium can advantageously provide a desirable location for measuring and/or monitoring left atrial pressure, blood viscosity, temperature, and/or other cardiac crammer(s). Sensor implant devices in accordance with one or more embodiments of the present disclosure may be implanted using transcatheter procedures, or any other percutaneous procedures. Alternatively, sensor implant devices in accordance with aspects of the present disclosure may be placed during open-heart surgery (e.g., sternotomy), mini-sternotomy, and/or other surgical operation.

Cardiac Implant Devices and Structures

Figure 6:
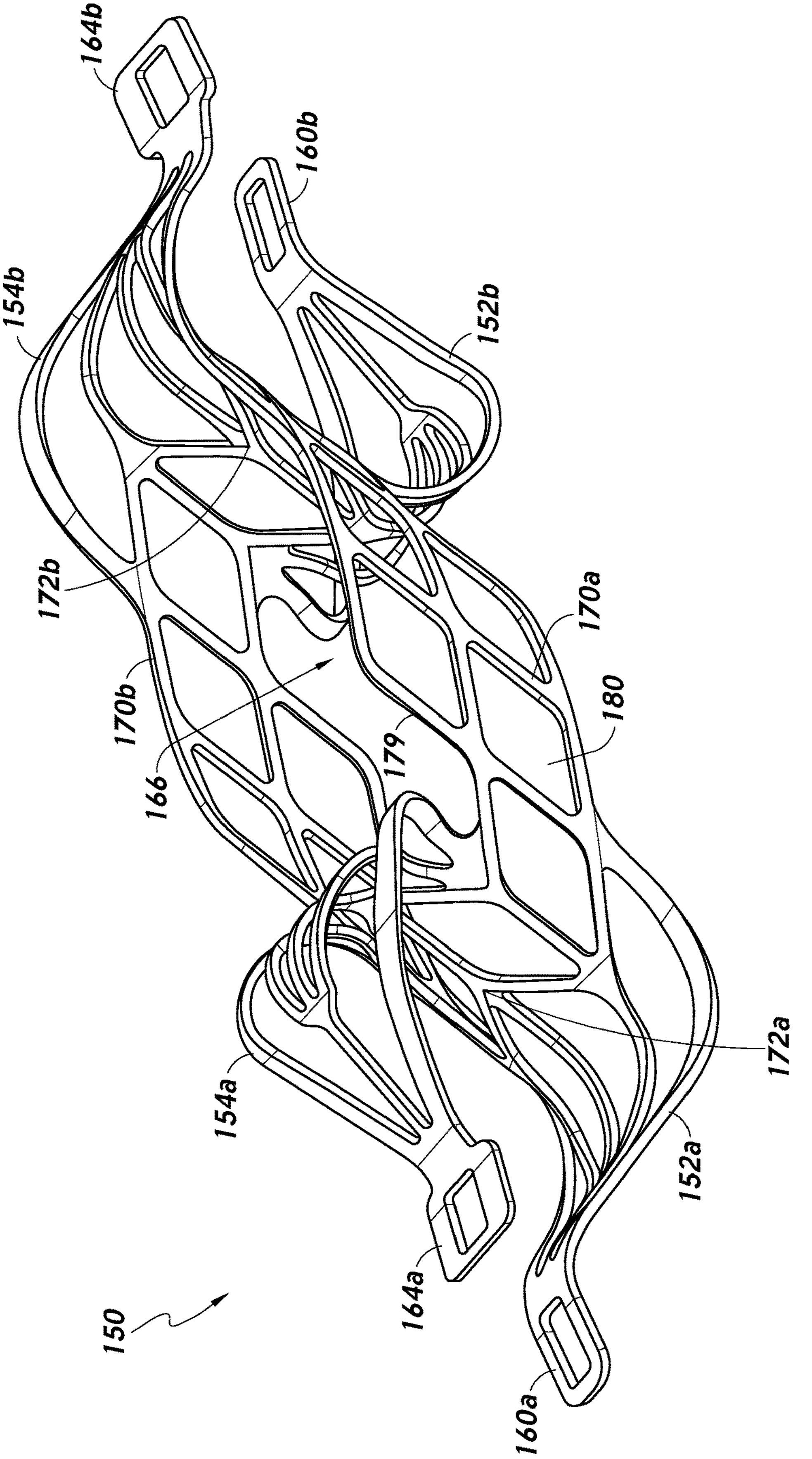
FIG. 6 illustrates an example shunt-type anchor structure in accordance with one or more embodiments.

FIG. 6 illustrates an example shunt structure 150 in accordance with one or more embodiments. The shunt structure 150 may represent an embodiment of a cardiac implant device that may be integrated with pressure sensor functionality in accordance with certain embodiments disclosed herein. The shunt structure 150 may be an expandable shunt. When expanded, a central flow channel 166 of the shunt 150 may define a generally circular or oval opening/barrel. The channel/barrel 166 may be configured to hold the sides of a puncture opening in a tissue wall to form a blood flow path between chamber(s) or vessel(s) of the heart that are separated by the tissue wall. For example, the shunt 150 may be configured to be implanted in the wall separating the coronary sinus and the left atrium. The central flow channel/barrel 166 may be partly formed by a pair of side walls 170*a*, 170*b* defined by a generally parallelogram arrangement of thin struts 179 that forms an array of parallelogram-shaped cells or openings 180. In some embodiments, substantially the entire shunt 150 is formed by super-elastic struts that are configured to be compressed and fit into a catheter (not shown) and subsequently expanded back to the relaxed shape as shown in FIG. 6.

Formation of the shunt 150 using a plurality of interconnected struts forming cells therebetween may serve to at least partially increase the flexibility of the shunt, thereby enabling compression thereof and expansion at the implant site. The interconnected struts around the central flow channel/barrel 166 advantageously provide a cage having sufficient rigidity and structure to hold the punctured tissue in an open position. End walls 172*a*, 172*b* of the central flow channel/barrel 166 can serve to connect the side walls 170*a*, 170*b* and extend between distal and proximal flanges, or arms, 152, 154 on each side. The side walls 170*a*, 170*b* and end walls 172*a*, 172*b* together may define a tubular lattice, as shown. The end walls 172*a*, 172*b* can comprise thin struts 179 extending at a slight angle from a central flow axis of the shunt 150.

Although the illustrated shunt 150 comprises struts that define a tubular or circular lattice of open cells forming the central flow channel/barrel 166, in some embodiments, the structure that makes up the channel/barrel 166 forms a substantially contiguous wall surface over at least a portion thereof. In the illustrated embodiment, the tilt of the shunt structure 150 may facilitate collapse of the shunt into a delivery catheter (not shown), as well as the expansion of the flanges/arm 152, 154 on both sides of a target tissue wall. The central flow channel 166 may remain essentially unchanged between the collapsed and expanded states of the shunt 150, whereas the flanges/arms 152, 154 may transition in and out of alignment with the angled flow channel.

Although certain embodiments of shunts disclosed herein comprise flow channels/barrels having substantially circular or elliptical cross-sections, in some embodiments, shunt structures in accordance with the present disclosure have rectangular, diamond-shaped, or other-shaped flow channel configurations. For example, relatively elongated side walls compared to the illustrated configuration of FIG. 6 may produce a rectangular or oval-shaped flow channel. Such shapes of shunt flow channels may be desirable for larger punctures, while still being configured to collapse down to a relatively small delivery profile.

In some embodiments, each of the distal and proximal flanges/arms 152, 154 is configured to curl outward from the end walls 172*a*, 172*b* and be set to point approximately radially away from the central flow channel 166 in the expanded configuration. The expanded flanges/arms may serve to secure the shunt 150 to a target tissue wall. Additional aspects and features of shunt structures that may be integrated with sensor devices/functionality in accordance with embodiments of the present disclosure are disclosed in U.S. Pat. No. 9,789,294, entitled "Expandable Cardiac Shunt," issued on Oct. 17, 2017, the disclosure of which is hereby expressly incorporated by reference in its entirety. Although certain embodiments are disclosed herein in the context of shunt structures similar to that shown in FIG. 6 and described above, it should be understood that shunt structures or other implant devices integrated with pressure sensor functionality in accordance with embodiments of the present disclosure may have any type, form, structure, configuration, and/or may be used or configured to be used for any purpose, whether for shunting or other purpose or functionality.

Sensor-Retention Structures Integrated with Shunts and Other Implant Devices

Figure 7A:
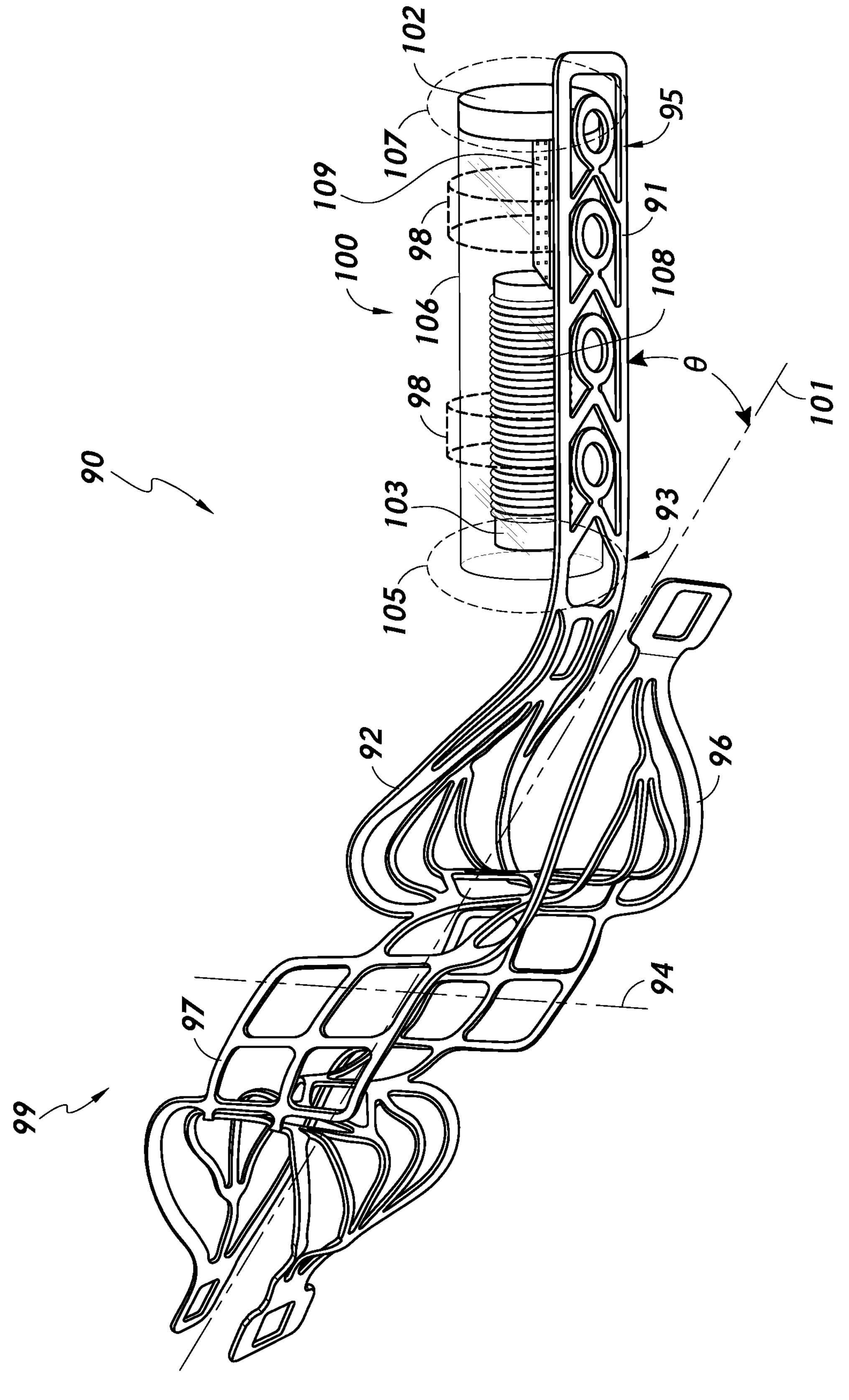
FIGS. 7A and 7B illustrate sensor implant devices having sensor-support struts in accordance with one or more embodiments.

Sensor devices in accordance with embodiments of the present disclosure may be integrated with cardiac shunt structures/devices or other implant devices using any suitable or desirable attachment or integration mechanism or configuration. FIG. 7A illustrates a sensor implant device 90 comprising a shunt structure 99 and an integrated sensor 100 in accordance with one or more embodiments. In some embodiments, the sensor 100 may be built or manufactured together with and/or into the shunt structure 99 to form a unitary structure. In some embodiments, the sensor 100 may be attached to or integrated with a sensor-support strut/arm member 95 of the shunt structure 99.

The sensor 100 includes a sensor element 102, such as a pressure sensor transducer. Relative to the arm member 95 of the shunt structure 99, the transducer element 102 (e.g., pressure transducer) may be oriented/positioned at a distal 107 or proximal 105 end or area of the sensor 100. For example, the illustrated embodiment of FIG. 7A includes the sensor element/transducer 102 disposed at the distal end 107 of the sensor 100.

As described herein, the sensor 100 may be configured to implement wireless data and/or power transmission. The sensor 100 may include an antenna component 108 and control circuitry 109 configured to facilitate wireless data and/or power communication functionality. In some embodiments, the antenna 108 comprises one or more conductive coils, which may facilitate inductive powering and/or data transmission. The coil 108 can be wrapped around magnetic (e.g., ferrite) and/or air core 103 in some embodiments.

The sensor 100 may advantageously be biocompatible. For example, the sensor 100 may comprise a biocompatible housing 106, such as a cylindrical or other-shaped housing comprising glass or other biocompatible material. The circuitry 109, sensor element 102, and/or antenna 108 may be at least partially contained within the housing 106, wherein the housing 106 is sealed to prevent exposure of such components to the external environment. However, at least a portion of the sensor element 102, such as a sensor diaphragm/membrane or other component, may be exposed to the external environment at least in part in some embodiments in order to allow for pressure readings, or other parameter sensing, to be implemented. The housing 106 may comprise an at least partially rigid cylindrical or tube-like form, such as a glass cylinder form, wherein the sensing probe 102 is disposed at one or both ends 105, 107 of the sensor assembly 106. In some embodiments, the sensor assembly is approximately 3 mm or less in diameter and/or approximately 20 mm or less in length. The sensor element 102 may comprise a pressure transducer, as described herein.

The sensor assembly 100 may be configured to communicate with an external system when implanted in a heart or other area of a patient's body. For example, the sensor 100 may receive power wirelessly from the external system and/or communicate sensed data or waveforms to and/or from the external system. The sensor assembly 106 may be attached to, retained/held by, and/or integrated with, the shunt structure 99 in any suitable or desirable way. For example, in some implementations, the sensor 100 may be attached to and/or retained by the shunt structure 99 using mechanical attachment means. In some embodiments, as described in detail below, the sensor assembly 106 may be contained in a pouch or other receptacle that is attached to the shunt structure 99.

The sensor element 102 may comprise a pressure transducer. For example, the pressure transducer may be a microelectromechanical system (MEMS) transducer comprising a semiconductor diaphragm component. In some embodiments, the transducer may include an at least partially flexible or compressible diaphragm component, which may be made from silicone or other flexible material. The diaphragm component may be configured to be flexed or compressed in response to changes in environmental pressure. The control circuitry 109 may be configured to process signals generated in response to said flexing/compression to provide pressure readings. In some embodiments, the diaphragm component is associated with a biocompatible layer on the outside surface thereof, such as silicon nitride (e.g., doped silicon nitride) or the like. The diaphragm component and/or other components of the pressure transducer 102 may advantageously be fused or otherwise sealed to/with the housing 106 in order to provide hermetic sealing of at least some of the sensor assembly components.

The control circuitry 109 may comprise one or more electronic application-specific integrated circuit (ASIC) chips or die, which may be programmed and/or customized or configured to perform monitoring functionality as described herein and/or facilitate transmission of sensor signals wirelessly. The antenna 108 may comprise a ferrite core wrapped with conductive material in the form of a plurality of coils (e.g., wire coil). In some embodiments, the coils comprise copper or other metal. The antenna 108 may advantageously be configured with coil geometry that does not result in substantial displacement or heating in the presence of magnetic resonance imaging. In some implementations, the sensor implant device 90 may be delivered to a target implant site using a delivery catheter (not shown), wherein the delivery catheter includes a cavity or channel configured to accommodate the advancement of the sensor assembly 106 therethrough. The sensor-support strut/structure 95 may deflect by some amount θ with respect to an axis 101 of a tissue wall in which the sensor implant device 90 is configured to be implanted.

In some embodiments, the sensor 100 is pre-attached to the sensor-retention structure 95 and/or integrated therewith prior to implantation. For example, in some embodiments, the sensor-retention structure 95 forms at least a portion of the housing of the sensor 100, such that the sensor-retention structure 95 and at least a portion of the housing of the sensor 100 are a unitary form.

In some embodiments, the angle or position of the sensor-retention structure 95 and/or sensor 100 relative to a longitudinal axis 101 of the shunt structure 99 is such that the sensor 100 projects away from the longitudinal axis 101. For example, where the shunt structure 99 is engaged with biological tissue along the dimension/plane of the longitudinal axis 101, the sensor 100 may advantageously project at least partially away from the biological tissue, such as into a chamber cavity (e.g., atrium of a heart). In some embodiments, the sensor-retention structure 95 is configured, or can be configured, substantially at a right angle or 90° orientation with respect to the axis/plane 101, such that the sensor 100 is substantially orthogonal to the longitudinal axis/plane of the shunt. Such configurations may advantageously allow for the sensor element 102 to be positioned a desirable distance away from the shunted flow flowing through the flow path axis 94.

The sensor element 102 of the sensor 100 may be disposed or positioned at any area/location of the sensor 100. For example, the sensor element 102 may advantageously be disposed at or near a distal portion 107 of the sensor 100. Alternatively or additionally, a sensor element may be disposed or positioned at or near a proximal portion 105 of the sensor 100.

Figure 7B:
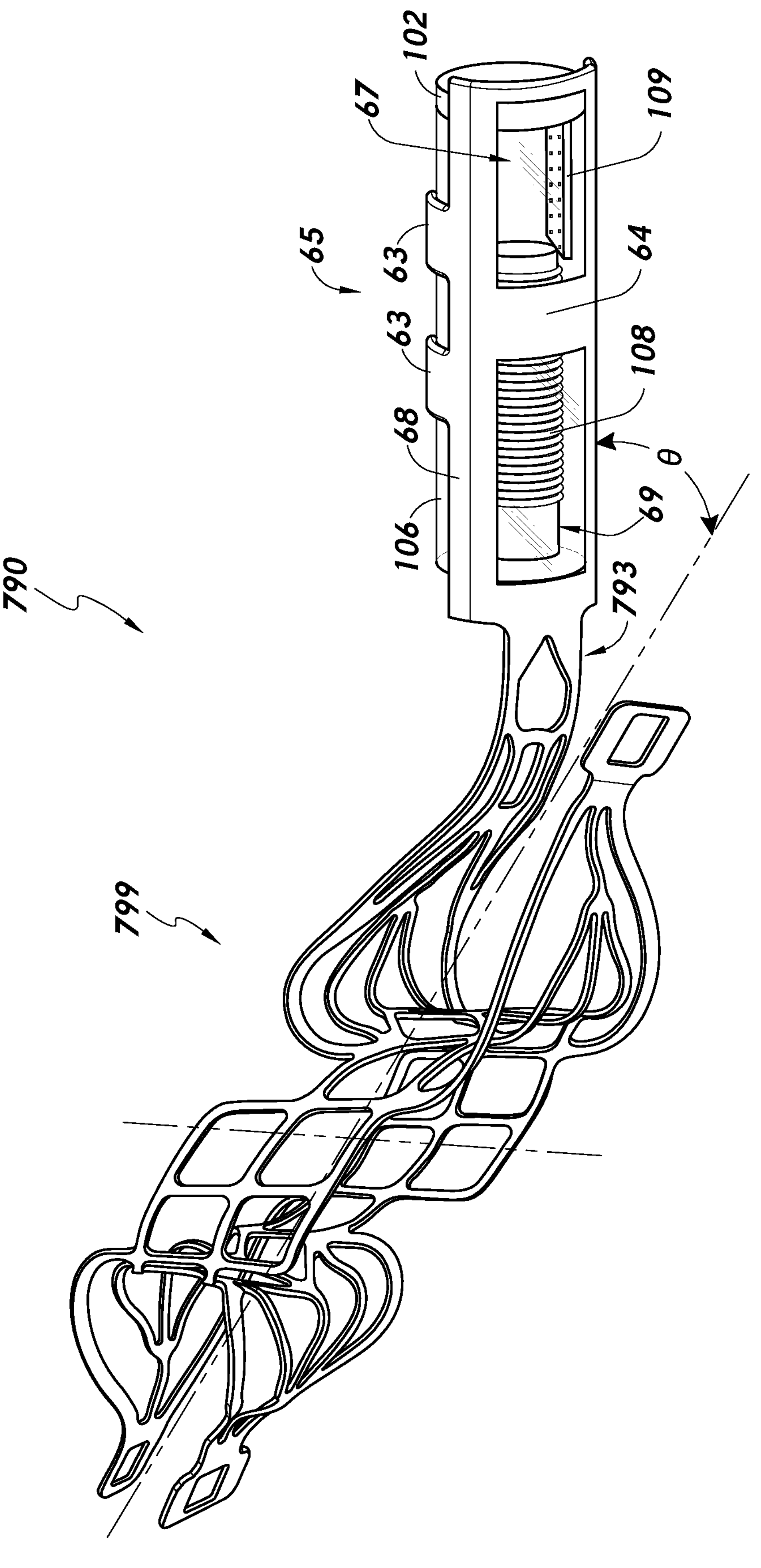

The embodiment of FIG. 7A shows a strut/backbone-type sensor-retention structure 95 which may be associated with one or more strap-type retention features 98 configured to hold the sensor device 100 to the strut 95. FIG. 7B shows a sensor implant device 790 including a shunt structure 799 and a sensor-retention structure 65 having certain curved features associated with back support 64 and side support 68 features thereof, wherein such curved features are configured to cradle/hold the sensor cylinder 106 thereon. The sensor-retention structure 65 further includes one or more retention fingers 63 for holding the sensor cylinder 106 against the structure 65. The sensor-retention structure 65 may be attached to or integrated with an arm 793 of the sensor implant device 799. The sensor-retention structure 65 can include a window feature 69 that provides an opening that is at least partially axially-aligned with the antenna 108, thereby reducing interference with signals transmitted to/from the antenna 108. In some embodiments, an additional window 67 is also formed in the structure 65. Further details of sensor-retention structures like that shown in FIG. 7B are provided below.

Figure 8:
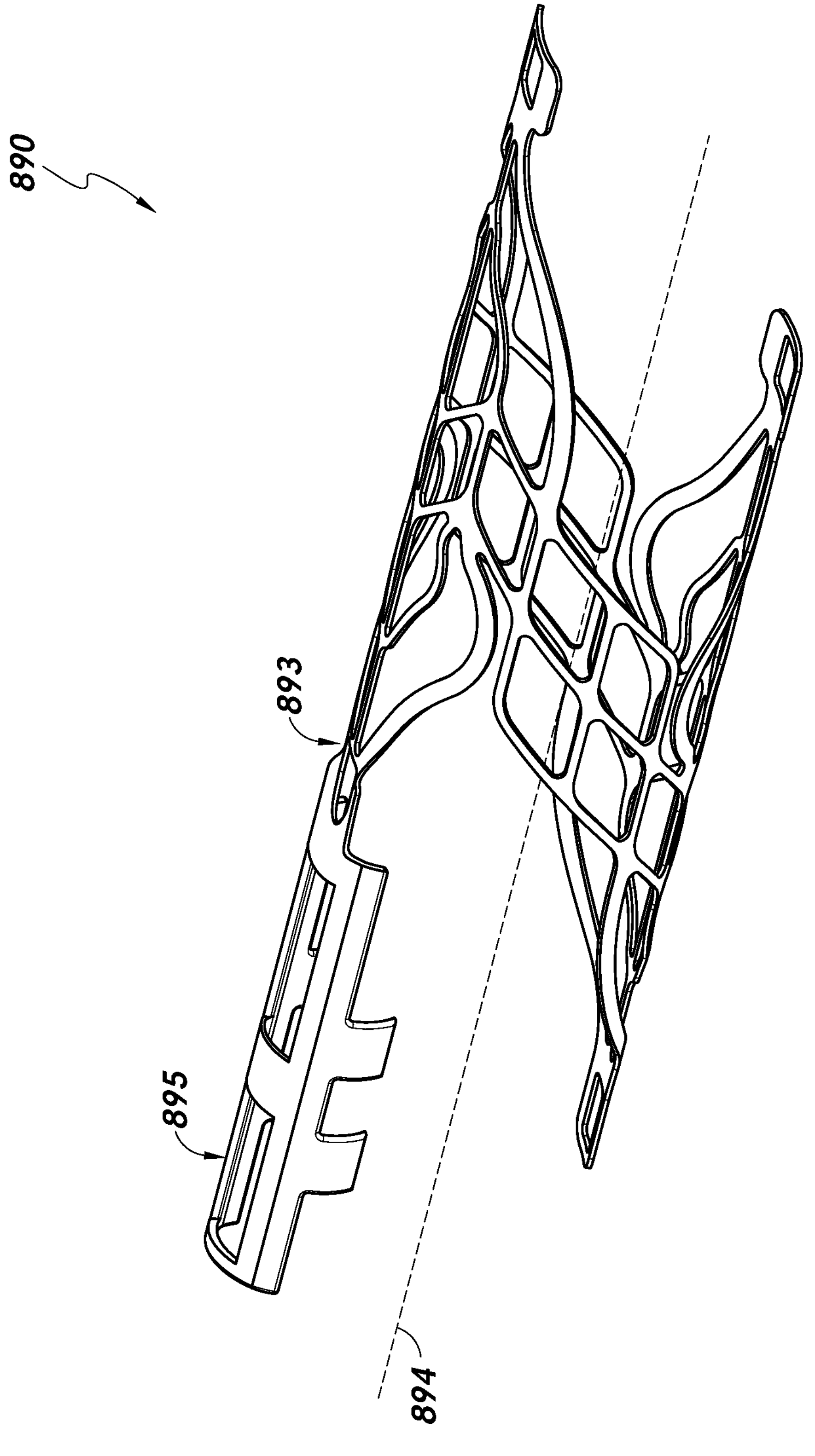
FIG. 8 shows a perspective view of an implant device including a sensor-retention structure in a catheter-delivery (e.g., at least partially collapsed) configuration in accordance with one or more embodiments.

FIG. 8 shows a perspective view of a sensor implant device 890 in an at least partially collapsed configuration for delivery through a delivery sheath or catheter (not shown). The shunt device 890 includes a sensor-retention structure/arm 895 attached or associated with an arm 893 of the shunt device. After deployment of the sensor implant device 890, the arms of the implant may expand radially outward to secure the implant device 890 to a target tissue wall.

Sensor Holder Stabilizers

Generally, pressure conditions in the left atrium, or other chamber of the body in which sensor implant devices in accordance with aspects of the present disclosure may be implanted, can be such that components of such implant devices that are not sufficiently stabilized can experience vibration, dislodgment, movement, and/or other torque or tension conditions. Therefore, sensor-retention struts/arms that are associated with various embodiments of the present disclosure can suffer from mechanical vibration after implantation in some biological environments. Such vibration and/or other pressure-related effects can affect sensor readings in some instances. For example, mechanical vibration can affect the ability of a sensor element to obtain/generate desirably consistent and/or accurate signals. As an example, with respect to embodiments utilizing compression-based pressure sensing functionality (e.g., capacitive or piezoresistive diaphragm-deflection sensors), where mechanical vibration and/or other pressure-induced movement of a sensor-retention strut/arm is not in sync with the cardiac rhythm of the heart, constructive and/or destructive interference may corrupt sensor readings, such that such pressure sensor readings are inaccurate and/or subject to undesirable signal noise.

Embodiments of the present disclosure can include certain sensor stabilization features and/or systems and processes associated therewith. With respect to any of the disclosed embodiments, sensor-retention struts/structures and/or associated stabilizers can be placed at or near the atrial septum wall or the wall separating the left atrium from the coronary sinus, as described in detail herein. Stabilizer features in accordance with aspects of the present disclosure may be attached and/or integrated with a sensor-retention structure, such as integrated with a frame of a stent device or other implant device.

In some embodiments, the present disclosure relates to sensor-retention structures having associated therewith one or more stand-type stabilizer components/features. Such stabilizer features can advantageously serve to secure a sensor-retention structure/holder and/or minimize unwanted motion or vibration. In some embodiments, sensor-retention structures having integrated/associated stabilizer(s) can be configured to be delivered using certain minimally-invasive (e.g., percutaneous) procedure(s).

Figure 9:
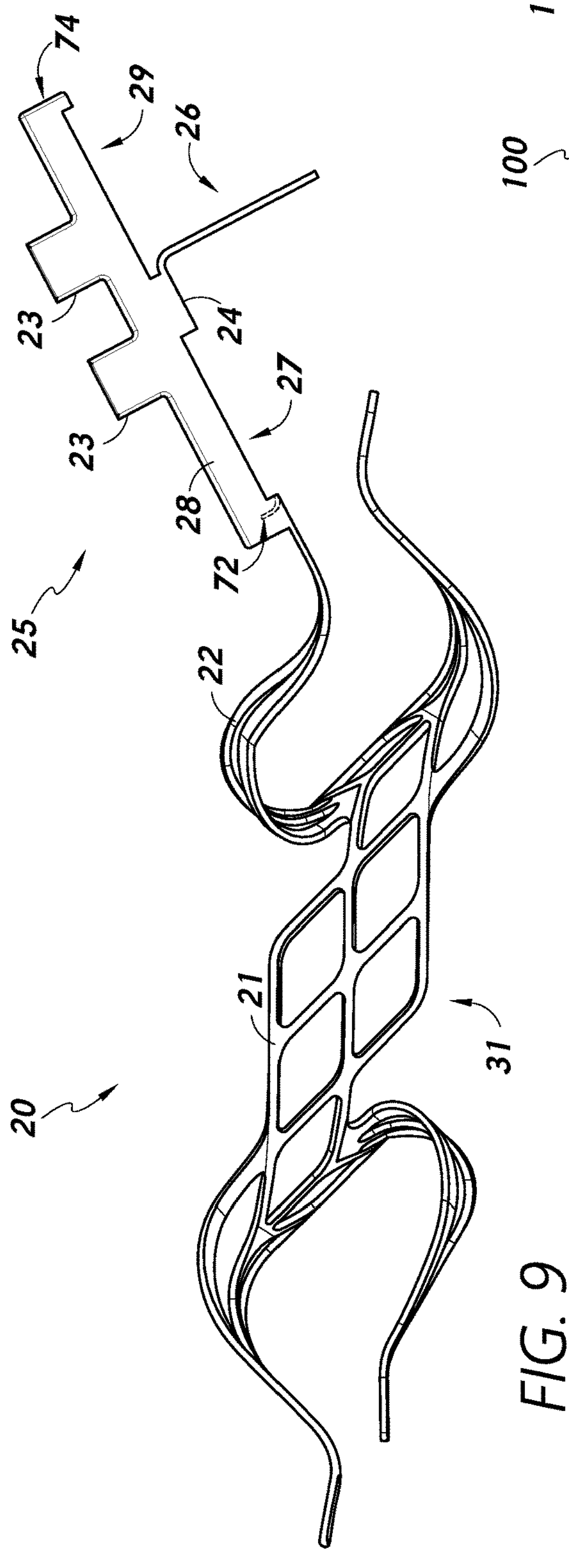
FIG. 9 shows a side view of a medical implant device including a sensor-retention structure and a sensor stabilizer feature in accordance with one or more embodiments.
Figure 10:
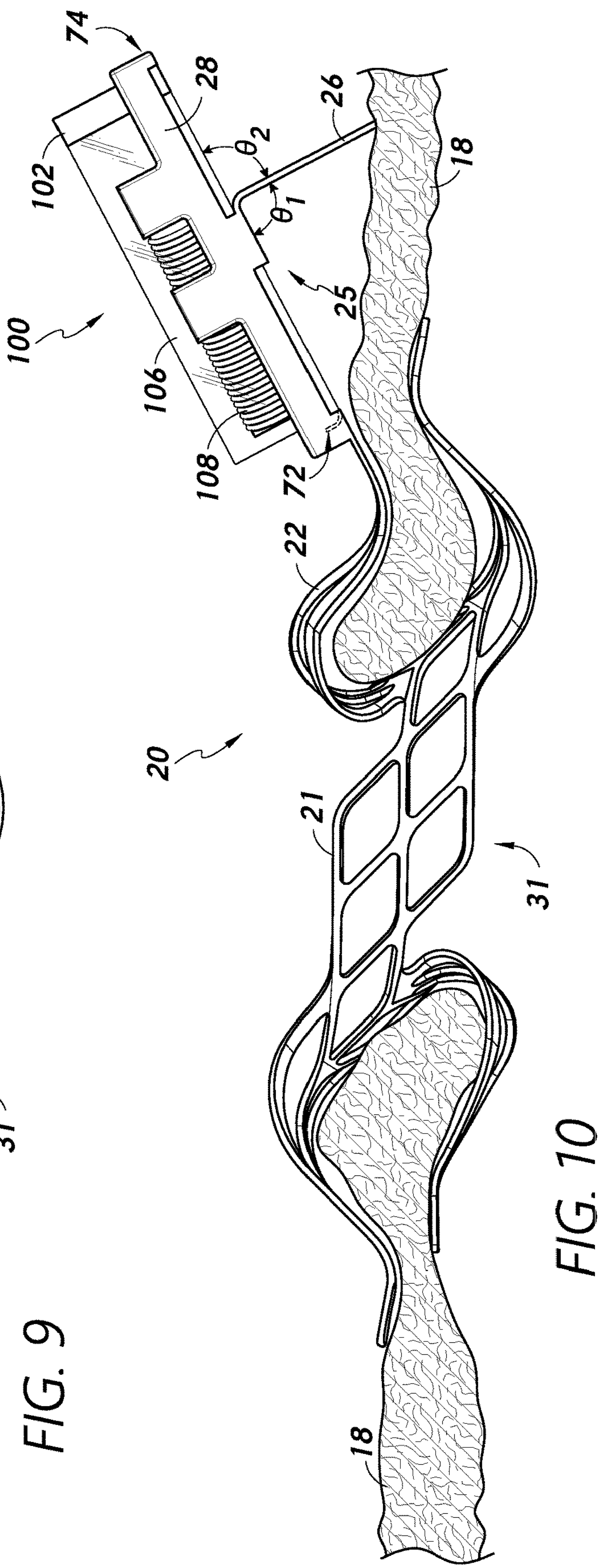
FIG. 10 shows a side view of a medical implant device including a sensor-retention structure and a sensor stabilizer feature implanted in a tissue wall in accordance with one or more embodiments.

FIG. 9 illustrates a sensor implant device 20 configured to hold a sensor 100 that is mechanically attached or fastened to a portion of a sensor-retention structure 25. The sensor implant device 20 includes a sensor stabilizer feature 26 configured to stabilize the sensor 100 and/or sensor-retention structure 25 when implanted in a patient. FIG. 10 shows a side view of the sensor implant device 20 including the sensor-retention structure 25 and the sensor stabilizer feature 26 as implanted in a tissue wall 18 in accordance with one or more embodiments.

The sensor-retention structure/arm 25 may be a unitary form with the arm 22 of the implant structure 20. In some embodiments, the sensor-retention structure 25 is an extension of, or otherwise associated with, the arm member 22. The sensor 100 may be attached to the retention/support structure 25 by any suitable or desirable attachment means, including adhesive attachment or mechanical engagement. For example, the sensor-retention structure 25 may comprise or be associated with one or more retention features 23, which may comprise one or more clamps, straps, ties, sutures, collars, clips, tabs, or the like. Such retention features 23 may circumferentially encase or retain the sensor 100, or a portion thereof. In some embodiments, the sensor 100 may be attached to the sensor-retention structure 25 through the application of mechanical force, either through sliding the sensor 100 through the retention features 23 or through clipping, locking, or otherwise engaging the sensor 100 with the sensor-retention structure 25 by pressing or applying other mechanical force thereto.

In some embodiments, the sensor-retention structure 25 includes one or more distal and/or proximal stopper features 72, 74. The stopper features 72, 74 can comprise one or more tabs that may be configured to pop-up or extend on one or more sides of the sensor-retention structure 25 for impeding axial sliding/movement of the sensor 100. Such tabs may comprise memory metal (e.g., Nitinol) or other at least partially rigid material.

In some embodiments, various components of sensor implant devices, sensor-retention structures, and/or stabilizer structures, or portions thereof, may be treated with anticoagulant drugs and/or coated with certain materials designed to reduce the risk of blood clotting associated with implantation of such devices. Stabilizers in accordance with embodiments of the present disclosure can comprise, for example, nickel-titanium metal alloy (e.g., Nitinol), or another shape-memory material.

As shown, the sensor-retention structure 25 shown in FIGS. 9 and 10 includes a radially-projecting stabilizer 26, which may be configured or configurable to project away from the body 28 of the sensor-retention structure 25 to provide a contact with the tissue wall 18. For example, FIG. 10 shows the sensor implant device 20 implanted in a tissue wall 18, wherein the stabilizer component/feature 26 is shown in a deployed configuration. In the deployed configuration, the stabilizer 26 projects away from the structure 25 at an angle $\theta_1$ with respect to a proximal side of the stabilizer 26 and an angle $\theta_2$ with respect to a distal side of the stabilizer 26. Generally, the angles $\theta_1$, $\theta_2$ may sum to 180°, and may be any value between about 15° and 165°.

The sensor-retention structure 25 can have any suitable or desirable form, shape, and/or configuration. The illustrated embodiment of FIGS. 9 and 10 is provided as an example only, and it should be understood that stabilizer devices/features may be associated with sensor-retention structures having any suitable or desirable size or configuration. Example sensor-retention structures that may have stabilizer devices/features of the present disclosure associated therewith are disclosed in U.S. Provisional Application No. 62/926,829, entitled SENSOR INTEGRATION IN CARDIAC IMPLANT DEVICES, the disclosure of which is incorporated by reference herein in its entirety.

The sensor-retention structure 25 may have one or more sensor-retention fingers 23, which may project/extend from a body 28 of the sensor-retention structure 25, may serve to hold/retain the sensor device 100 to the sensor-retention structure 25. That is, the finger(s) 23 may impede or prevent the sensor cylinder 106 from being drawn away from the body 28 of the sensor-retention search 25 in a radial direction with respect to an axis of the sensor-retention structure 25.

In some embodiments, the stabilizer 26 may be coupled to and/or integrated with a back portion/segment 24 of the sensor-retention structure 25. For example, the back segment 24 may span a circumferential portion of the sensor cylinder 106 and provide support thereto. In some embodiments, the stabilizer 26 may be configured to bend, such as may be caused by shape-memory characteristics of the stabilizer 26 and/or through manual bending/manipulation thereof using, for example, a surgical tool. The sensor-retention structure 25 may include one or more window features 27, 29, which may advantageously reduce the bulkiness of the implant device and/or reduce interference with transmission coils 108 of the sensor device 100, which may allow for wireless data transmission in some embodiments, as disclosed in detail above.

The sensor-retention structure 25 may further comprise one or more distal and/or proximal axial retention features 72, 74. For example, the illustrated proximal tab 72 may prevent the sensor 100 from sliding proximally on the sensor-retention structure 25. Furthermore, the distal retention bar 74 may be configured to contact at least a portion of a distal face of the sensor element 102 to prevent distal sliding thereof on the sensor-retention structure 25.

The implementation of the stabilizer device/feature 26 can help reduce vibration and/or other movement towards and away from the tissue wall 18. In some embodiments, the stabilizer 26 may further reduce side-to-side motion/vibration (e.g., motion parallel to the tissue wall 18). The stabilizer 26 may further reduce stress on the arm 22 of the sensor implant device 20 from repetitive motion during, for example, cardiac cycling.

Figure 11B:
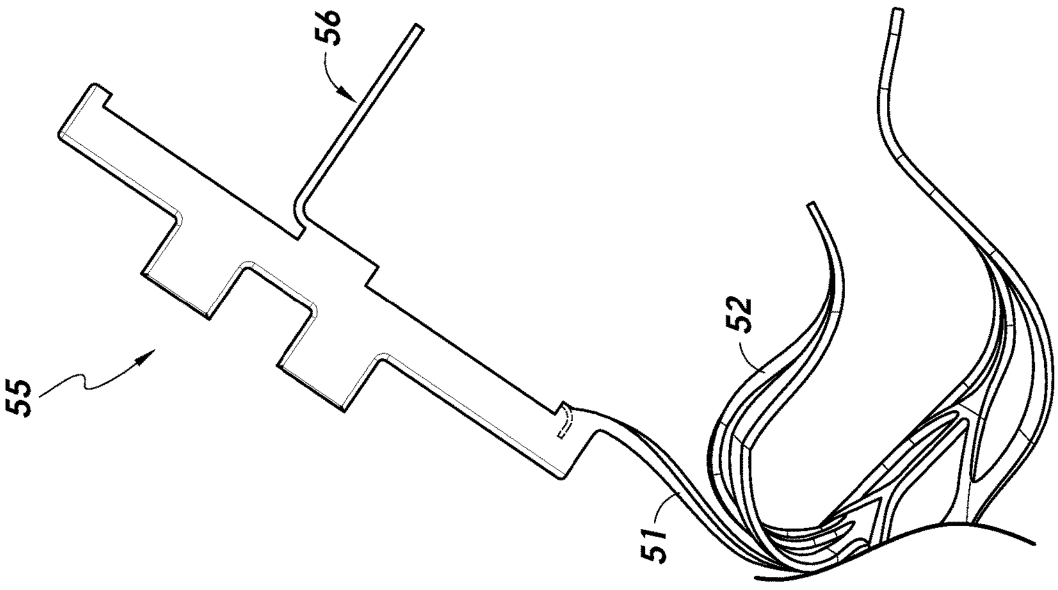
FIGS. 11A and 11B illustrate perspective and side views, respectively, of a sensor-retention structure configured to be bent away from an arm of a medical implant device in accordance with one or more embodiments.
Figure 11A:
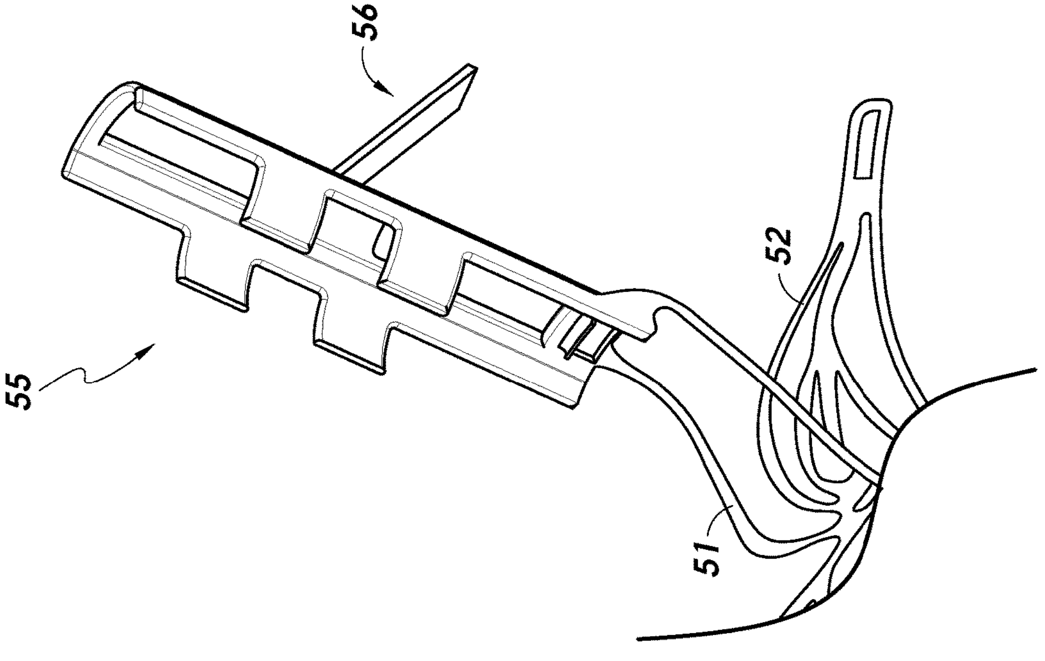

FIGS. 11A and 11B illustrate perspective and side views, respectively, of a sensor-retention structure 55 configured to be bent away from an arm 52 of a medical implant device in accordance with one or more embodiments. The sensor-retention structure 55 can be coupled to one or more outer (or inner) arms 51 that are provided in addition to the tissue-contact arm 52 of the associated implant device, the sensor-retention structure 55 includes a stabilizer 56, which may be similar in various respects to other sensor stabilizer features/devices disclosed herein.

Figure 12B:
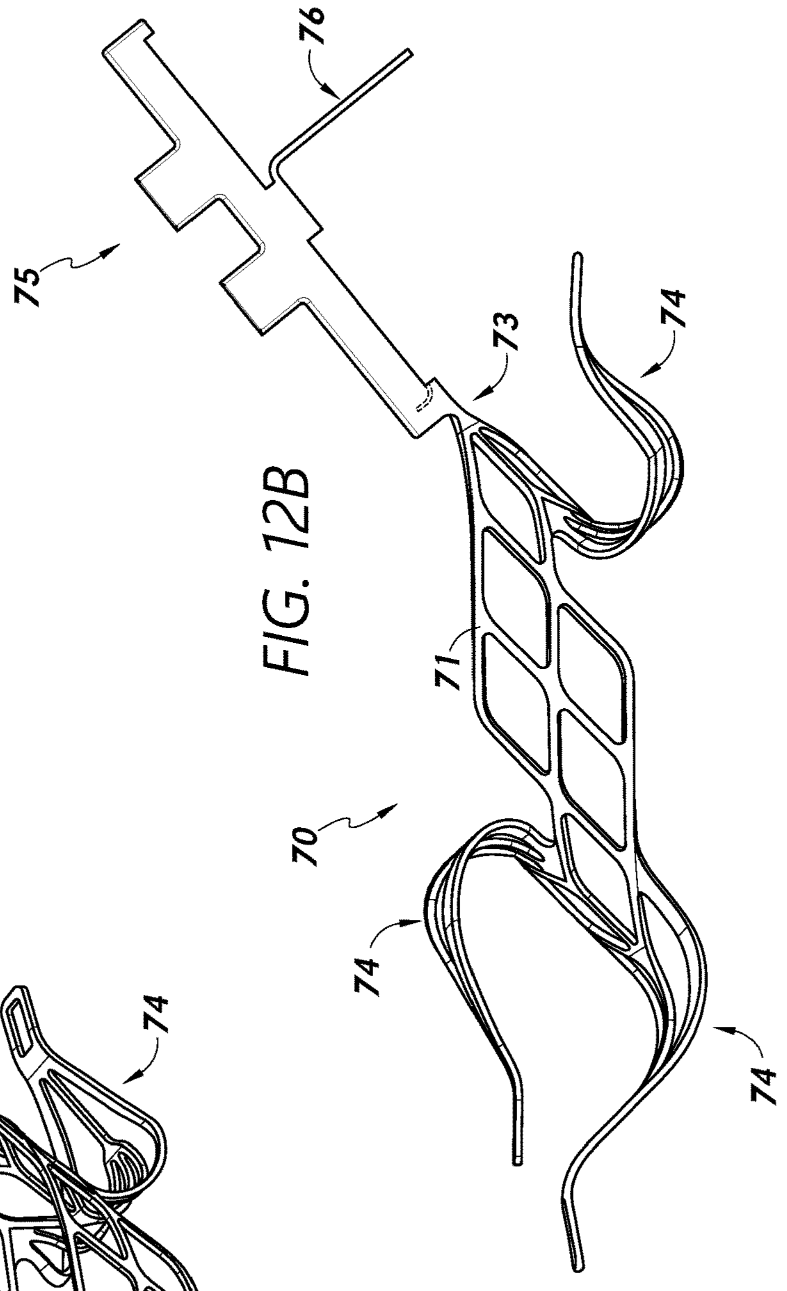
FIGS. 12A and 12B illustrate perspective and side views, respectively, of a medical implant device including a sensor-retention arm structure with a stabilizer in accordance with one or more embodiments.
Figure 12A:
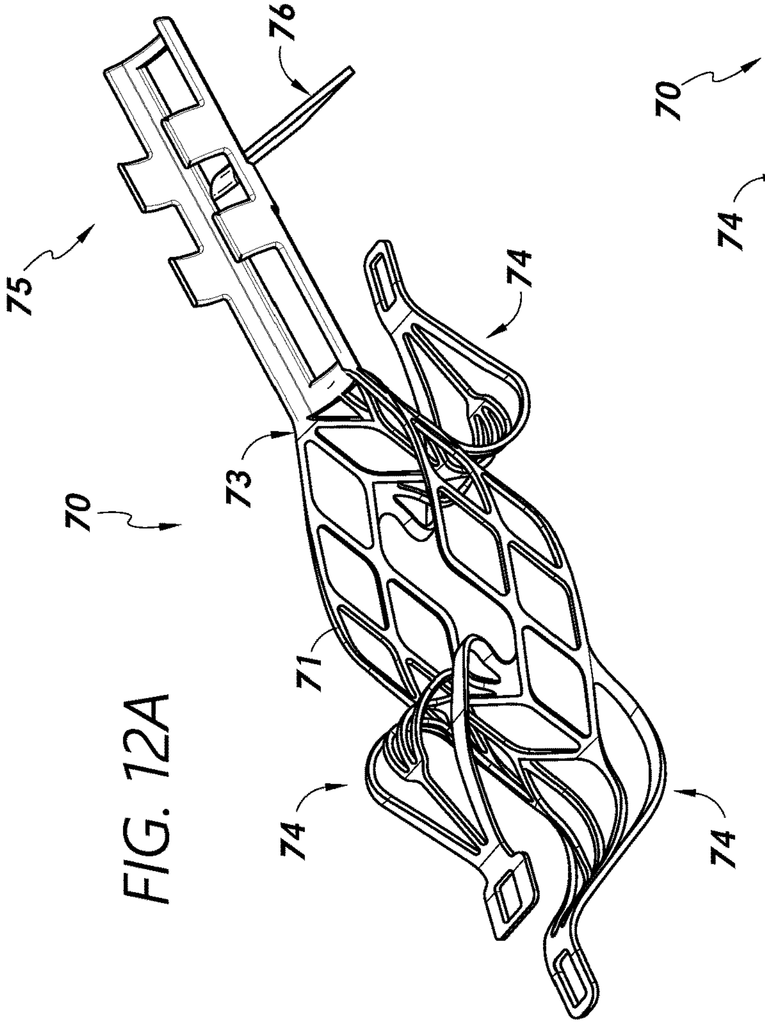

As described in detail herein, sensor-retention structures in accordance with aspects of the present disclosure can be integrated and/or associated with a distal portion of an arm member of an implant device, such as a shunt implant device or the like. By positioning such sensor-retention structures at a distal end of an implant support arm, the implant support arm may be configured to provide stabilization for the implant device. In some embodiments, an implant device may utilize a sensor-retention structure in place of one or more implant-stabilizing arms. FIGS. 12A and 12B illustrate perspective and side views, respectively, of a medical implant device 70 including a sensor-retention arm structure 75 with a stabilizer 76 in accordance with one or more embodiments. As shown in FIGS. 12A and 12B, the sensor-retention structure 75 may effectively serve as an implant-stabilizing arm without the need for an additional implant support arm at the area of the implant device associated with the retention structure 75.

As shown in FIGS. 12A and 12B, the sensor-retention structure 75 may be coupled to or otherwise associated with the implant device 70 at or near a base portion 73 thereof corresponding to where an implant-stabilizing arm may otherwise be positioned. For example, the base portion 73 may correspond to an outer portion of a barrel 71 of a shunt implant device as shown in FIGS. 12A and 12B. The implant device 70 may further comprise a plurality of additional arms 74 positioned at each of three corner portions of the implant device 70 with respect to the side view of FIG. 12B, such as corner portions of the barrel 71. One of the four corner portions of the implant device 70, rather than comprising a similar arm member like the other arm members 74, may comprise a sensor-retention structure 75 having a stabilizer 76 configured to provide mechanical contact with a tissue wall when implanted therein, thereby providing sensor-stabilization/support functionality similar to the functionality of the arms 74.

By positioning the sensor-retention structure 75 relatively close to the orifice/channel of the barrel 71, the stability of the sensor-retention structure 75 may be greater compared to certain other embodiments in which the sensor-retention structure is positioned greater distance away from the barrel 71. It should be understood that sensor-retention structures in accordance with aspects of the present disclosure may be associated with sensor-stabilizing arms having any desirable length, shape, and/or configuration.

Figure 13B:
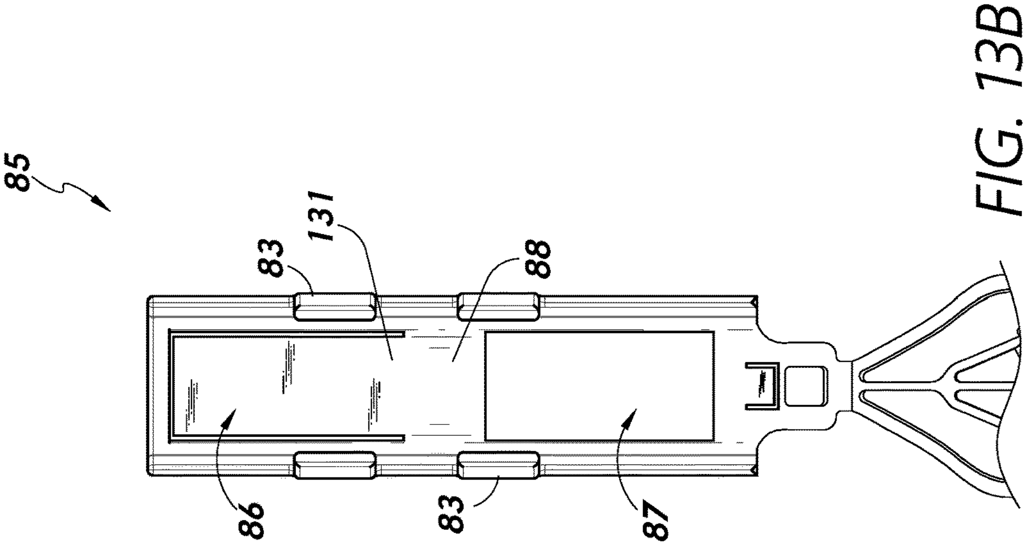
FIGS. 13A and 13B show a deployed side view and a non-deployed top view, respectfully, of a sensor-retention structure having a top-down projecting stabilizer in accordance with one or more embodiments.
Figure 13A:
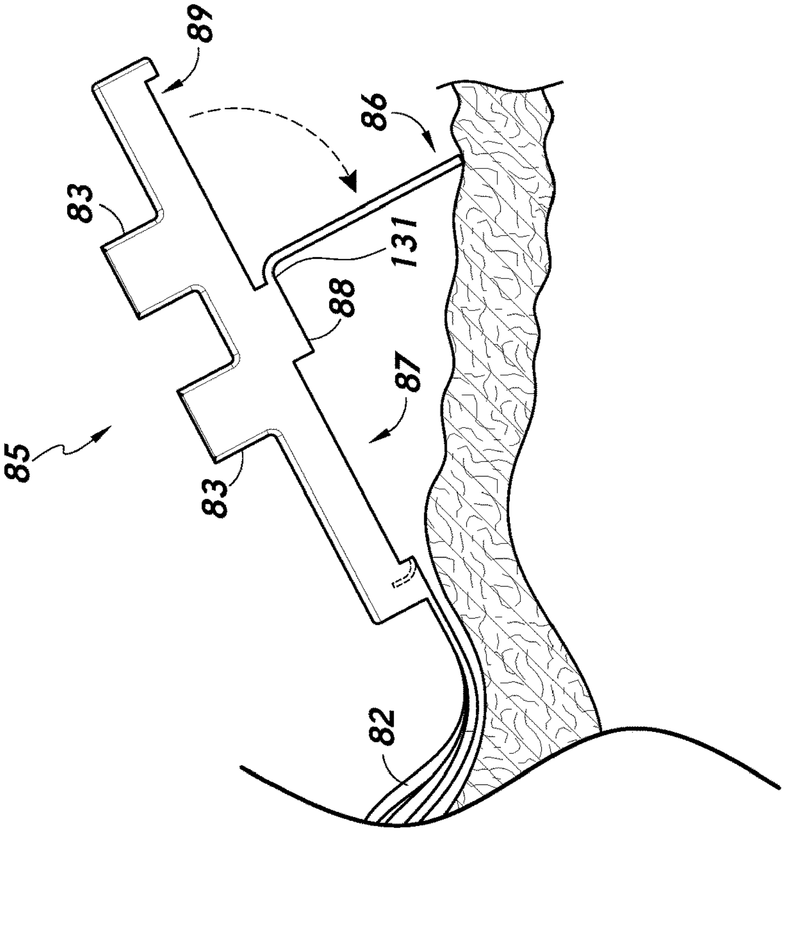

As described in detail herein, sensor stabilizers in accordance with aspects of the present disclosure may be integrated with and/or otherwise associated with a sensor-retention structure. For example, such stabilizers may be configured to be bent/folded and/or automatically bend or fold in accordance with shape-memory characteristics of the stabilizer and/or associated sensor-retention structure away from a body portion of the sensor-retention structure. Such bending/folding may be generally away from a distal end of the sensor-retention structure or a proximal end of the sensor-retention structure, depending on the configuration. FIGS. 13A and 13B show a deployed side view and a non-deployed top view, respectfully, of a sensor-retention structure 85 having a top-down extending stabilizer 86 in accordance with one or more embodiments.

In FIG. 13A, the sensor-retention structure 85 includes a stabilizer 86 that is integrated with the sensor-retention structure 85. For example, the stabilizer 86, as shown in the top-down view of FIG. 13B, may be laser-cut or otherwise cut out of the material of the body 88 of the sensor-retention structure 85. In embodiments in which the stabilizer 86 is cut out or otherwise formed such that a base 131 of the stabilizer 86 is on a proximal side of the stabilizer 86 with respect to the orientation of the sensor-retention structure 85, the stabilizer 86 may be configured to bend/fold downward (i.e. away from a distal end of the sensor-retention structure 85).

With respect to downward-bending/folding stabilizers as shown in FIGS. 13A and 13B, the deployment of the stabilizer 86 may leave a window/opening 89 in the sensor-retention structure 85, as shown. In some embodiments, the sensor-retention structure 85 may further comprise a proximal window/opening 87. Such windows/openings 87, 89 may be desirable in some cases in order to provide a sensor retention structure having reduced bulkiness, while still providing sufficient sensor support. For example, the sensor-retention structure 85 may comprise one or more sensor-retention fingers 83, which may hold a sensor disposed in the sensor-retention structure 85 against the body 88 of the structure, such that additional longitudinal support of the sensor is not necessary in order to retain the sensor in the desired position. The window(s) 87, 89 may further provide openings through which wireless signals can propagate, thereby reducing interference with wireless signal transmissions to/from a sensor device retained by the structure 85. For example, antenna feature(s) of the sensor may axially and/or circumferentially overlap, at least in part, with one or both of the window(s) 87, 89.

In some embodiments, the stabilizer 86 may be deployed automatically when the sensor-retention structure 85 is released from the delivery system (e.g., delivery catheter) used to deliver the implant device to the target tissue/location. For example, the sensor-retention structure 85 and/or stabilizer 86 may comprise a shape-set memory metal, such as Nitinol or the like. In some implementations, a wire may be used in connection with the delivery system, wherein the wire may be used to deploy the stabilizer 86 manually, such as by pushing or pulling on one or more features of the stabilizer 86. For example, the stabilizer 86 may comprise one or more apertures, hooks, or other engaged features with which a deployment wire may engage in order to deploy the stabilizer.

Figure 14B:
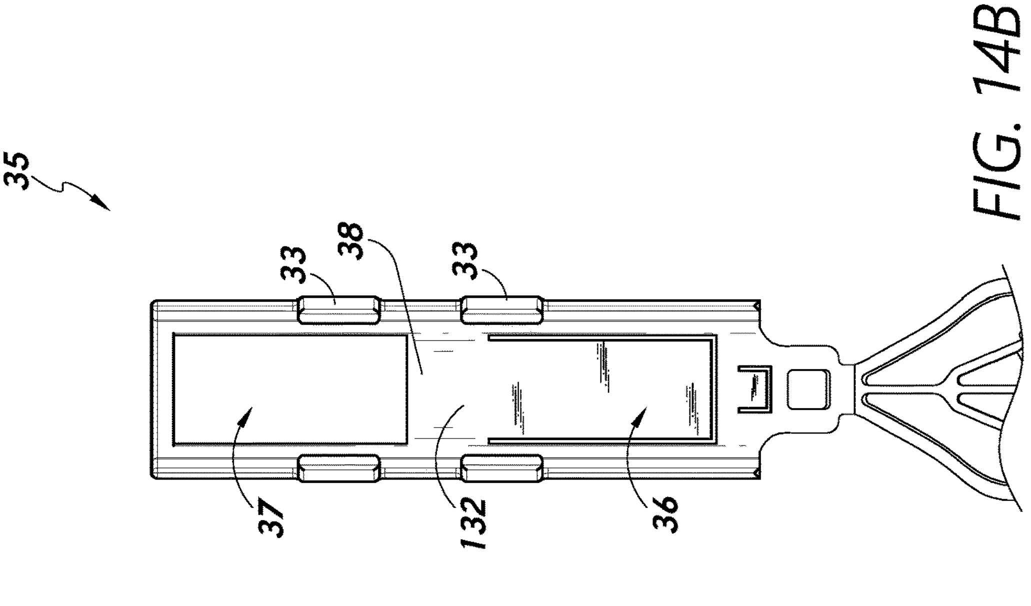
FIGS. 14A and 14B show a deployed side view and a non-deployed top view, respectfully, of a sensor-retention structure having a bottom-up projecting stabilizer in accordance with one or more embodiments.
Figure 14A:
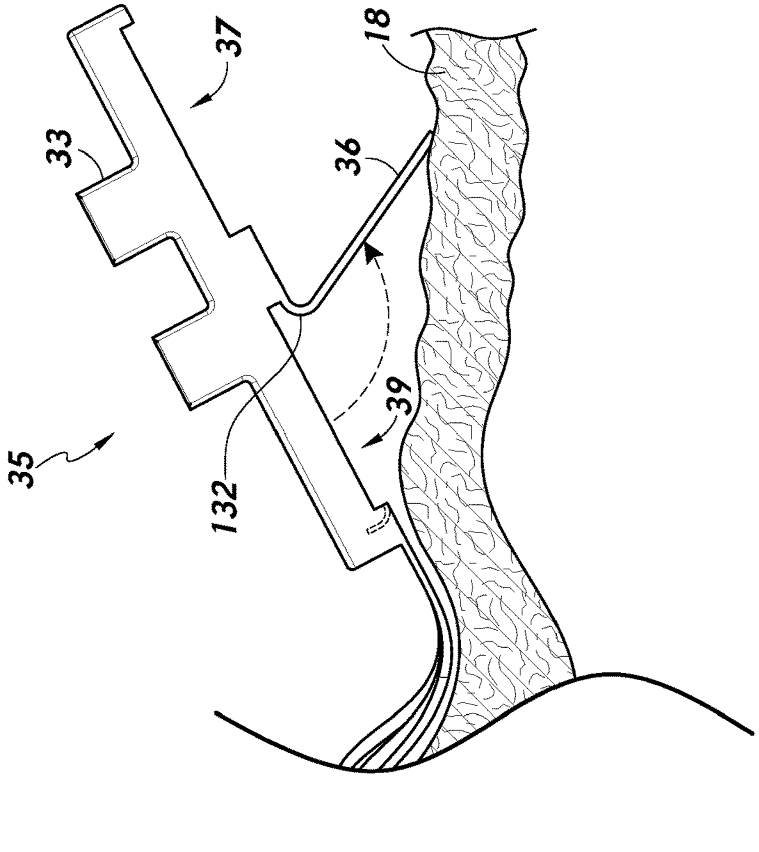

FIGS. 14A and 14B show a deployed side view and a non-deployed top view, respectfully, of a sensor-retention structure 35 having a bottom-up extending stabilizer 36 in accordance with one or more embodiments. In FIG. 14A, the sensor-retention structure 35 includes a stabilizer 36 that is integrated with the sensor-retention structure 35. For example, the stabilizer 36, as shown in the top-down view of FIG. 14B, may be laser-cut or otherwise cut out of the material of the body 38 of the sensor-retention structure 35. In embodiments in which the stabilizer 36 is cut out or otherwise formed such that a base 132 of the stabilizer 36 is on a distal side of the stabilizer 36 with respect to the orientation of the sensor-retention structure 35, the stabilizer 36 may be configured to bend/fold upward (i.e. away from a proximal end of the sensor-retention structure 35).

With respect to upward-bending/folding stabilizers as shown in FIGS. 14A and 14B, the deployment of the stabilizer 36 may leave a window/opening 39 in the sensor-retention structure 35, as shown. In some embodiments, the sensor-retention structure 35 may further comprise a distal window/opening 37. Such windows/openings 37, 39 may be desirable in some cases in order to provide a sensor-retention structure having reduced bulkiness, while still providing sufficient sensor-retention support. For example, the sensor-retention structure 35 may comprise one or more sensor-retention fingers 33, which may hold a sensor disposed in the sensor-retention structure 35 against the body 38 of the structure, such that additional longitudinal support of the sensor is not necessary in order to retain the sensor in the desired position. The window(s) 37, 39 may further provide openings through which wireless signals can propagate, thereby reducing interference with wireless signal transmissions to/from a sensor device retained by the structure 35. For example, antenna feature(s) of the sensor may axially and/or circumferentially overlap, at least in part, with one or both of the window(s) 37, 39.

As described above in connection with FIGS. 13A and 13B, the stabilizer 36 may be deployed automatically and/or manually. Furthermore, retraction of the stabilizer 36 may be achieved through manual and/or automatic mechanical movement. For example, in some embodiments, the stabilizer 36 may be bent as shown in FIG. 14A and placed against the tissue wall 18, wherein the tissue wall 18 holds the stabilizer 36 in the bent configuration shown in FIG. 14A. In such embodiments, pulling the sensor-retention structure 35 away from the tissue wall 18 may allow the stabilizer to automatically retract to occupy the space 39 previously vacated when the stabilizer 36 was bent/folded away from the sensor-retention structure 35.

Figure 15B:
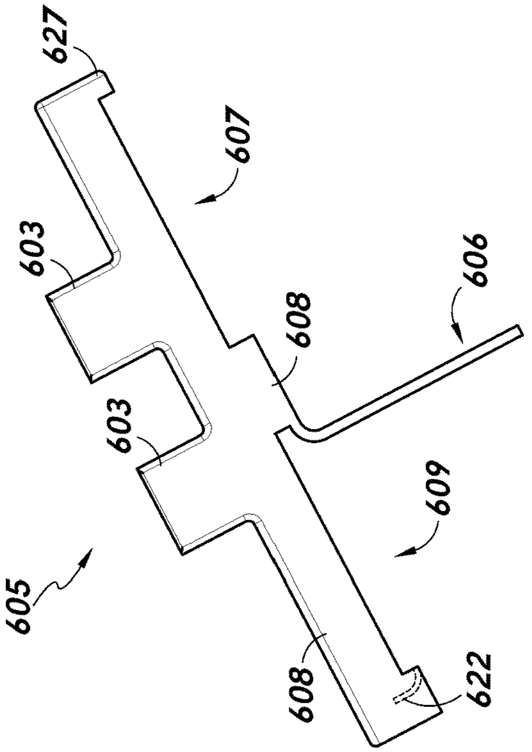
FIGS. 15A-C show perspective, side, and end views, respectively, of a sensor-retention structure having a stabilizer in accordance with one or more embodiments.
Figure 15D:
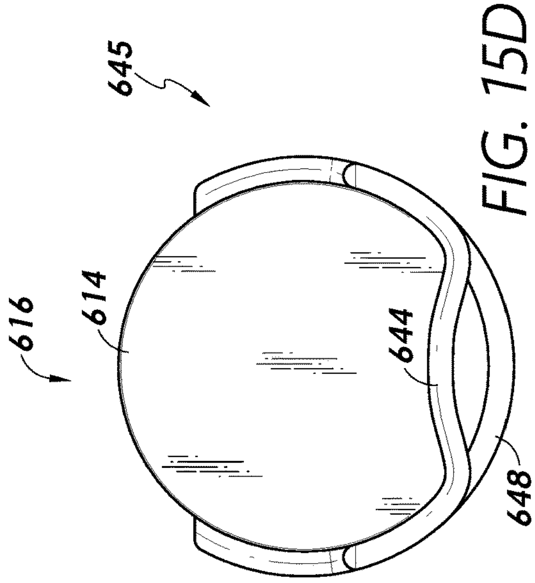
FIG. 15D shows an end view of a sensor-retention structure having a distal stopper feature in accordance with one or more embodiments.
Figure 15A:
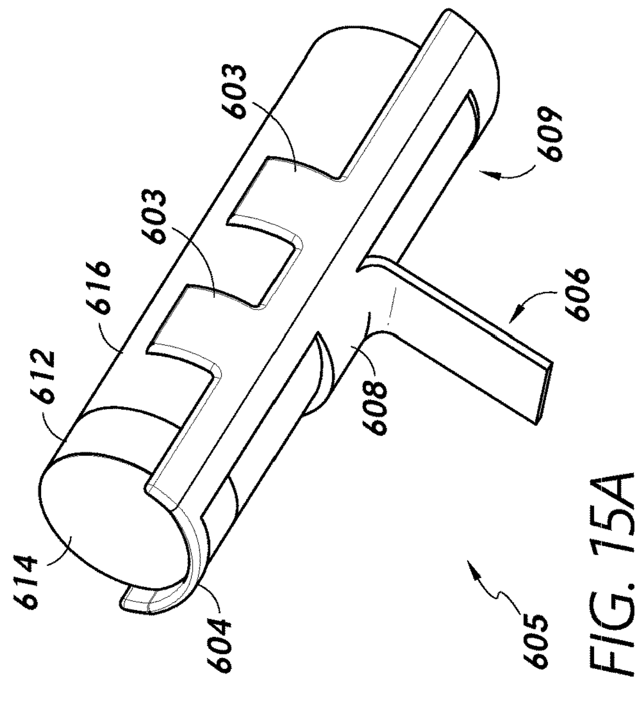
Figure 15C:
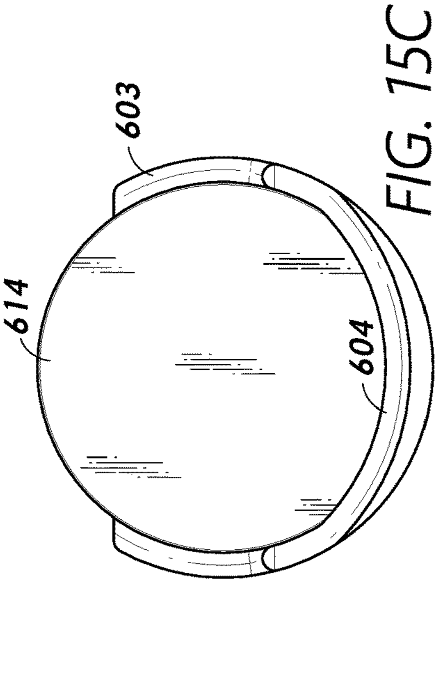

FIGS. 15A-C show views of a sensor-retention structure 605 having a stabilizer 606 in accordance with one or more embodiments. The sensor-retention structure 605, as shown in FIG. 15A, can include a distal stopper feature 604. For example, in some embodiments, the sensor-retention structure 605 has a generally curved/concave transverse shape, providing a cradle-type shape in which a cylindrical sensor 616 can be placed/rested. In some embodiments, a distal portion 604 of the curved form can have a radius of curvature that is less than that of a body portion 608 of the sensor-retention structure 605. That is, the distal stopper portion 604 can be at least partially flatter than the body portion 608 with respect to one or more arc-lengths thereof. Such configuration of the distal stopper bar/portion 604 is shown clearly in the end view of FIG. 15C. With the sensor cylinder 616 disposed within the curvature of the body portion 608 of the sensor-retention structure 605, wherein the curvature of the sensor-retention structure 605 may generally correspond to a curvature of the sensor 616, the relatively flatter stopper bar/portion 604 may radially overlap by some amount with the distal face 614 of the sensor 616, thereby preventing distal axial movement beyond the point of contact of the sensor face 614 with the stopper bar/portion 604.

FIG. 15D shows an alternate embodiment in which a distal stopper bar 644 has a similar circumferential length relative to the corresponding arc segment of the body 648 of the sensor-retention structure 645, wherein the distal bar 644 is pushed radially towards a central axis of the sensor 616 to thereby form an inward protrusion, as shown, that encroaches radially over the face 614 of the sensor 616, thereby providing axial obstruction to prevent distal movement of the sensor 616 beyond the stopper bar 644.

In some embodiments, as shown in FIG. 15B, the sensor-retention structure 605 includes a proximal trap/stopper 622, which may have a tab-type form. In some embodiments, the stopper 622 may be configured to manually and/or automatically fold/bend radially inward with respect to the axis defined by the curvature of the sensor-retention structure 605. Although the embodiment of FIGS. 15A and 15B includes a single kickstand-type stabilizer 606, it should be understood that, as with any other embodiment of the present disclosure, the sensor-retention structure 605 may comprise any suitable or desirable number of stabilizer features. Furthermore, as with any of the other embodiments disclosed herein, although the stabilizer 606 shown in FIGS. 15A and 15B is shown as a bottom-up stabilizer design, as described above in connection with FIGS. 14A and 14B, it should be understood that the stabilizer 606 may be a top-down stabilizer, or may have any other configuration in accordance with aspects of the present disclosure.

Figure 16B:
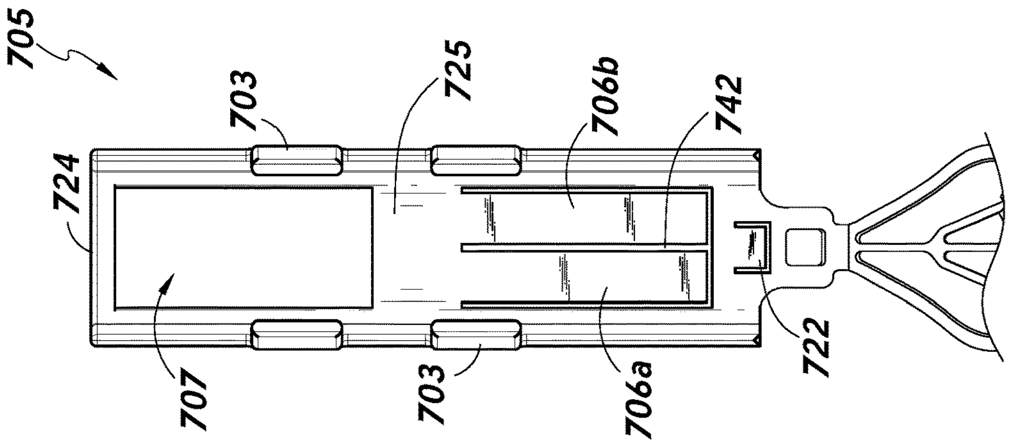
FIGS. 16A and 16B show a perspective deployed view and a non-deployed top view, respectively, of a sensor-retention structure having a plurality of stabilizers in accordance with one or more embodiments.
Figure 16A:
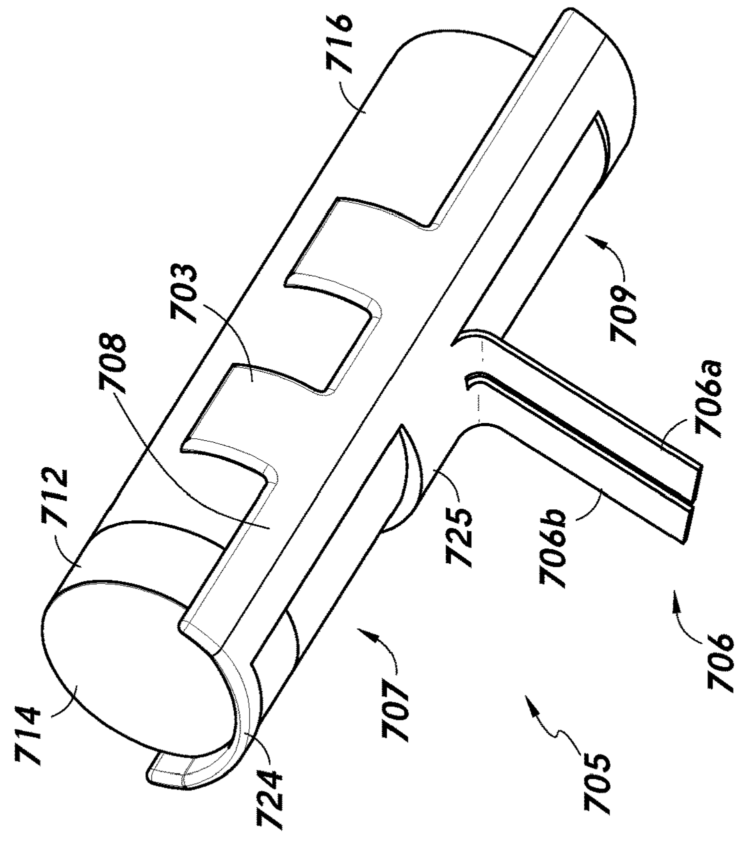

FIGS. 16A and 16B show a perspective deployed view and a non-deployed top view, respectively, of a sensor-retention structure 705 having a plurality of stabilizers 706 in accordance with one or more embodiments. Particularly, the illustrated sensor-retention structure 705 has a dual-kickstand configuration. That is, whereas certain embodiments are disclosed herein in the context of sensor-retention structures comprising a single stabilizer form/feature, the embodiment shown in FIGS. 16A and 16B includes two stabilizer features **706*a*, 706*b***.

The two stabilizers **706*a*, 706*b* may be substantially independent of one another, such that one of the stabilizers may be bent and/or manipulated independently of the other. In some embodiments, as shown in FIG. 16A, the stabilizer features 706*a*, 706*b* may extend in a substantially parallel relative orientation. In some embodiments, when the stabilizers 706*a*, 706*b* are bent/projected away from the sensor-retention structure 705, the stabilizers 706*a*, 706*b* may be inclined to project radially outward and somewhat away from one another with respect to distal end portions thereof. That is, in the deployed configuration, the respective distal ends of the sensor stabilizers 706*a*, 706*b*** may be farther apart than proximal portions thereof.

As shown in FIG. 16B, the stabilizers **706*a*, 706*b* may be cut (e.g., laser cut) from the form of the body 725 of the sensor-retention structure 705. As with other embodiments disclosed herein, the deployment of the stabilizers 706*a*, 706*b* may occur after deployment of the sensor-retention structure 705 based on shape-memory characteristics of the sensor-retention structure 705 and/or stabilizers 706*a*, 706*b*. Although the embodiment of FIG. 16B shows the stabilizers 706*a*, 706*b* positioned relative to one another such that a gap 742 is present between the stabilizers when in the delivery configuration shown in FIG. 16B, in some embodiments, a form of material of the base 725 of the sensor-retention structure 705 may be present between the stabilizers 706*a*, 706*b*, such that such a form of material separates the stabilizers, in addition to any space formed through laser cutting of the stabilizers 706*a*, 706*b***.

Figure 17B:
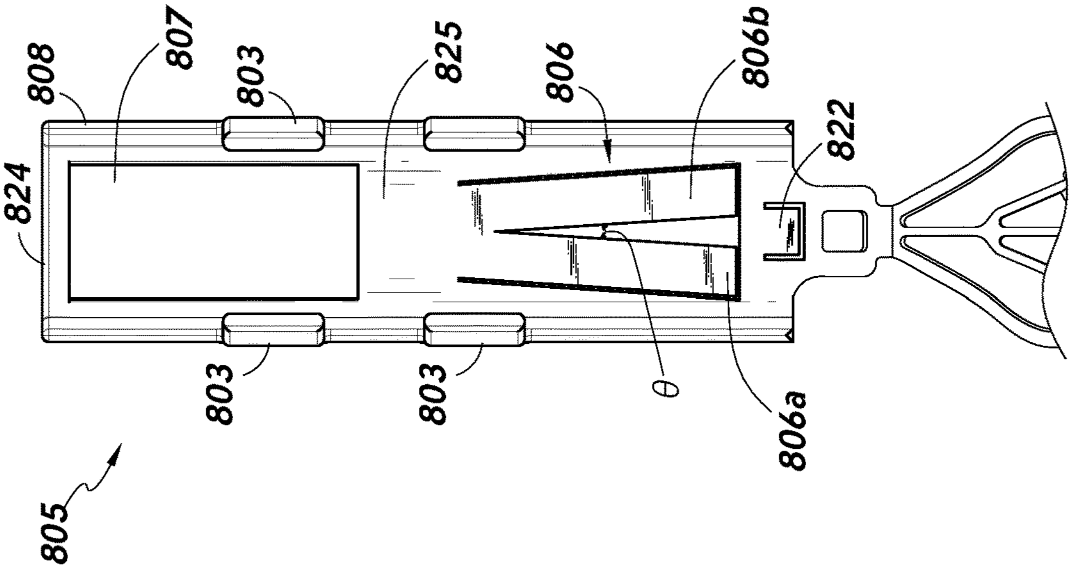
FIGS. 17A and 17B show a perspective deployed view and a non-deployed top view, respectively, of a sensor-retention structure having a plurality of stabilizers in accordance with one or more embodiments.
Figure 17A:
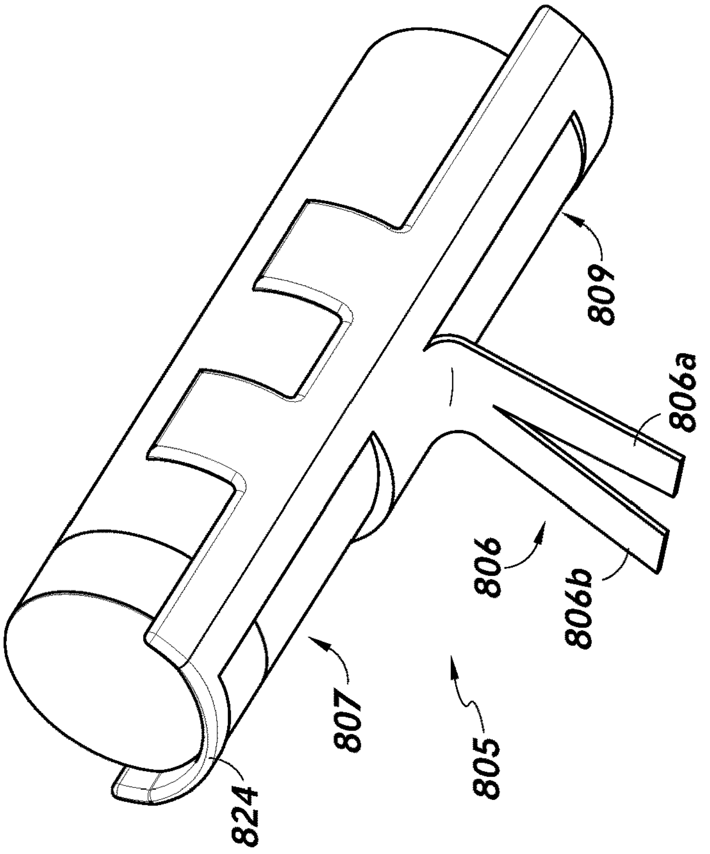

FIGS. 17A and 17B show a perspective deployed view and a non-deployed top view, respectively, of a sensor-retention structure 805 having a plurality of stabilizers 806 in accordance with one or more embodiments. The particular configuration of FIGS. 17A and 17B represents an alternative dual-stabilizer embodiment, wherein the stabilizers 806*a*, 806*b* are angled relative to one another. By constructing the stabilizers 806*a*, 806*b* at an angle, as shown in FIGS. 17A and 17B, such stabilizers may provide desirable lateral stability. For example, the angles of incidence of the respective stabilizers 806*a*, 806*b* with respect to contact with a tissue wall may be different relative to one another, thereby providing stability against movement/vibration at a wider range of angles. Although the overhead view shown in FIG. 17B shows the stabilizers 806*a*, 806*b* cut out such that uneven gaps are formed between the stabilizers 806*a*, 806*b* and/or between the stabilizers and the body 825 of the sensor-retention structure 805, in some embodiments, no such gaps exist. That is, the stabilizers 806*a*, 806*b* may be cut out of the sensor-retention structure form without producing gaps beyond the cut edges around the stabilizers 806A, 806B. Such may be true for any of the embodiments of cut-out stabilizer features disclosed herein.

Trauma Protection Features

Stabilizer features disclosed herein, as described in detail above, can provide stabilization for a sensor-retention structure or other component of an implant device through contact with a tissue wall, thereby providing mechanical coupling between the sensor-retention structure and the tissue wall via the stabilizer structure/feature. In view of such tissue contact, it may be desirable to design/configure stabilizer features in accordance with aspects of the present disclosure in a manner as to reduce the risk of injury and/or other damage to biological tissue through contact with a stabilizer feature. For example, where the sensor-retention structure is subject to certain vibration and/or other mechanical movements/forces, such forces/movement can result in repeated contact with the tissue wall, thereby breaking down the biological tissue and/or otherwise causing damage thereto over time. In some embodiments, the distal end of a stabilizer feature may be relatively sharp, thereby allowing for and/or causing penetration of the distal end of the stabilizer into the relevant biological tissue. Therefore, it may be desirable for certain embodiments to incorporate trauma protection features with respect to distal end portions of a stabilizer feature.

Figure 18B:
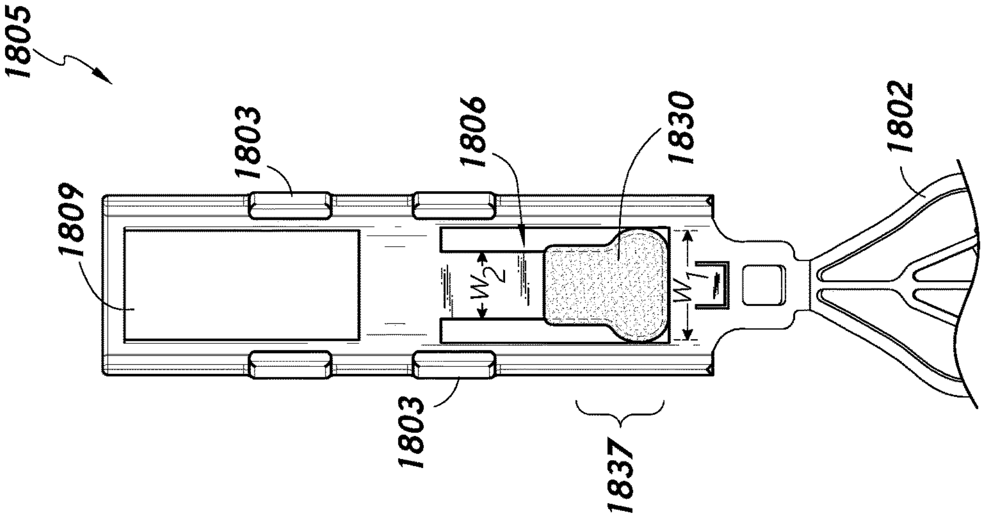
FIGS. 18A and 18B show a side deployed view and a non-deployed top view, respectively, of a sensor-retention structure comprising a sensor stabilizer in accordance with one or more embodiments.
Figure 18A:
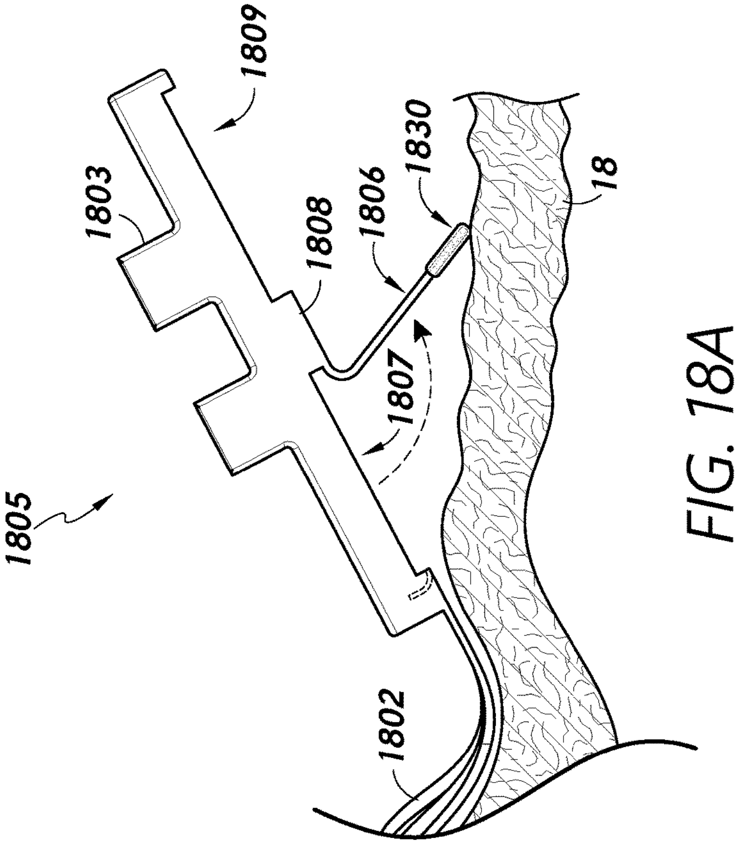

FIGS. 18A and 18B show side and straight-on views, respectively, of a sensor stabilizer 1806 associated with a sensor-retention structure 1805 in accordance with one or more embodiments. The stabilizer 1806 may have any configuration according to any of the embodiments disclosed herein. The stabilizer 1806 further comprises a trauma-protection coating or covering 1830 that covers at least a portion of a distal end portion of the stabilizer 1806.

The coating or material 1830 can serve to prevent and/or protect against tissue trauma resulting from contact between the stabilizer 1806 and biological tissue. Furthermore, in some embodiments, the coating/covering 1830 can provide a greater friction coefficient compared to a stabilizer not including such a coating/covering. Therefore, the coating/covering 1830 may advantageously reduce and/or prevent sliding of the stabilizer 1806 on the tissue wall 18. In some embodiments, when the distal end of the stabilizer 1806 punctures and/or becomes embedded at least partially within the tissue wall 18, the coating 1830 may be configured to facilitate and/or accelerate tissue in-growth between the tissue wall 18 and the coating 1830, which may serve to provide additional stability for the stabilizer and sensor-retention structure 1805.

As shown in FIG. 18B, the stabilizer 1806 may include a foot feature 1837, at least a portion of which may be covered by the coating/material 1830 in some embodiments. However, it should be understood that embodiments of the present disclosure may include stabilizers having foot features without trauma-protection coatings/coverings thereon. The foot feature 1837 may have a width dimension $w_1$ that is greater than a width dimension $w_2$ of the medial and/or base portions of the stabilizer 1806. In some embodiments, the foot feature 1837 is rounded with respect to one or more corners or edges thereof, thereby providing a less traumatic physical contact interface for contacting the biological tissue without puncturing or irritating the same. Although the foot feature 1837 is shown as having an at least partially flat distal end surface, in some embodiments, the distal end of the foot feature 1837 may be rounded and/or circular. Although FIG. 18B shows a foot feature 1837 associated with the stabilizer 1806, in some embodiments, stabilizers including trauma-protection coverings/coatings do not include identifiable foot features.

Figure 19B:
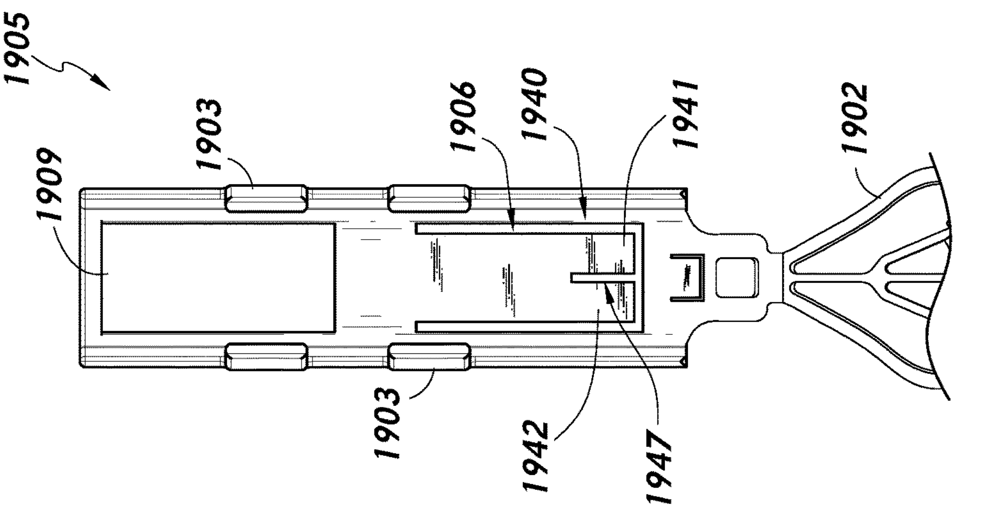
FIGS. 19A and 19B show a side deployed view and a non-deployed top view, respectively, of a sensor-retention structure comprising a sensor stabilizer in accordance with one or more embodiments.
Figure 19A:
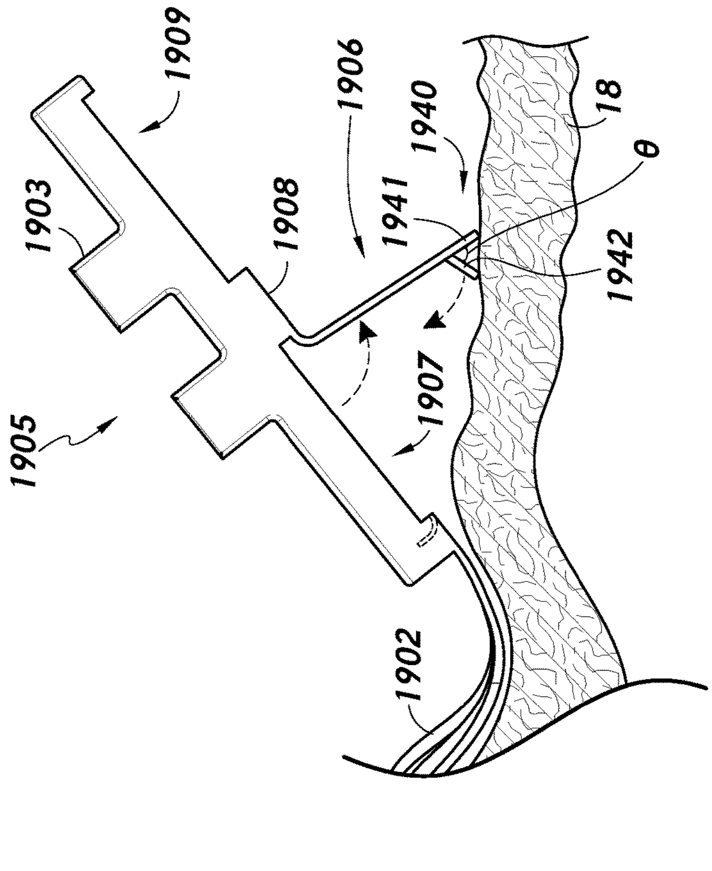

FIGS. 19A and 19B show side and straight-on views, respectively, of a sensor stabilizer 1906 associated with a sensor-retention structure 1905 in accordance with one or more embodiments. The stabilizer feature 1906 may be configured according to any of the embodiments disclosed herein. In addition, the stabilizer 1906 may comprise certain additional trauma-protection and/or stabilization features associated therewith. For example, as shown, the stabilizer 1906 may include one or more splaying foot features 1941, 1942. For example, as shown in the view of FIG. 19B, which shows the stabilizer 1906 in a pre-deployment configuration, the stabilizer 1906 may include a cut 1947 at or near a distal end portion of the stabilizer 1906, wherein such cut 1947 forms separate foot features 1941, 1942, which may be splayed in opposite directions relative to one another in a deployed configuration in order to provide a foot stabilizer feature 1940.

FIG. 19A shows the foot stabilizer 1940 with the foot feature 1942 bent away from the plane of the stabilizer 1906. With the foot feature 1942 and the foot feature 1941 separated, as shown in FIG. 19A, the contact force of the stabilizer 1906 on the tissue wall 18 may be distributed between the foot feature 1941 and the foot feature 1942, thereby potentially reducing the trauma and/or impact on the tissue wall 18 from the stabilizer 1906. Although the angle θ illustrated in FIG. 19A between the foot feature 1942 and the foot feature 1941 are shown as being less than approximately 90°, it should be understood that, as deployed, the angle between the foot features 1941, 1942 may be any suitable or desirable angle. For example, the angle theta may be an angle of about 90°, between about 90° and 135°, between about 135° and 180°, about 180°, or greater than 180°. Furthermore, although FIGS. 19A and 19B show two foot features 1941, 1942, and a cut 1947 separating them, in some embodiments, the foot feature 1940 does not include separate foot features. Rather, a distal portion of the stabilizer 1906 may be bent/bendable away from the plane of the stabilizer 1906, thereby provide a contact surface that is closer to parallel with the tissue surface 18 than is the medial portion of the stabilizer 1906. For example, with respect to the view of FIG. 19A, such a foot feature may advantageously be bent in the direction of the distal end of the sensor-retention structure 1905, to thereby present a tissue-contact surface that is more in-line with the tissue surface 18 than the plane of the medial portion of the stabilizer 1906 is. Various configurations of foot features disclosed herein can prevent deep-tissue penetration of stabilizer features in some implementations.

Figures 1, 20:
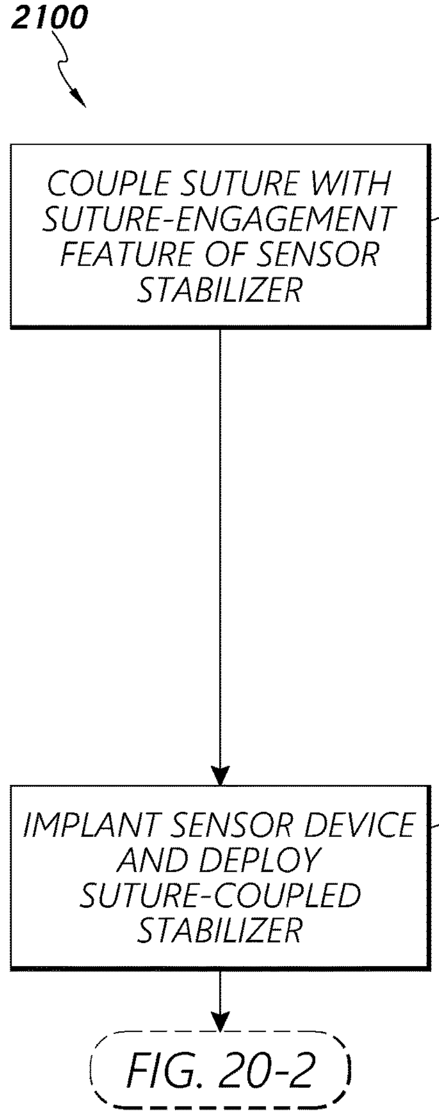
Figures 1, 21:
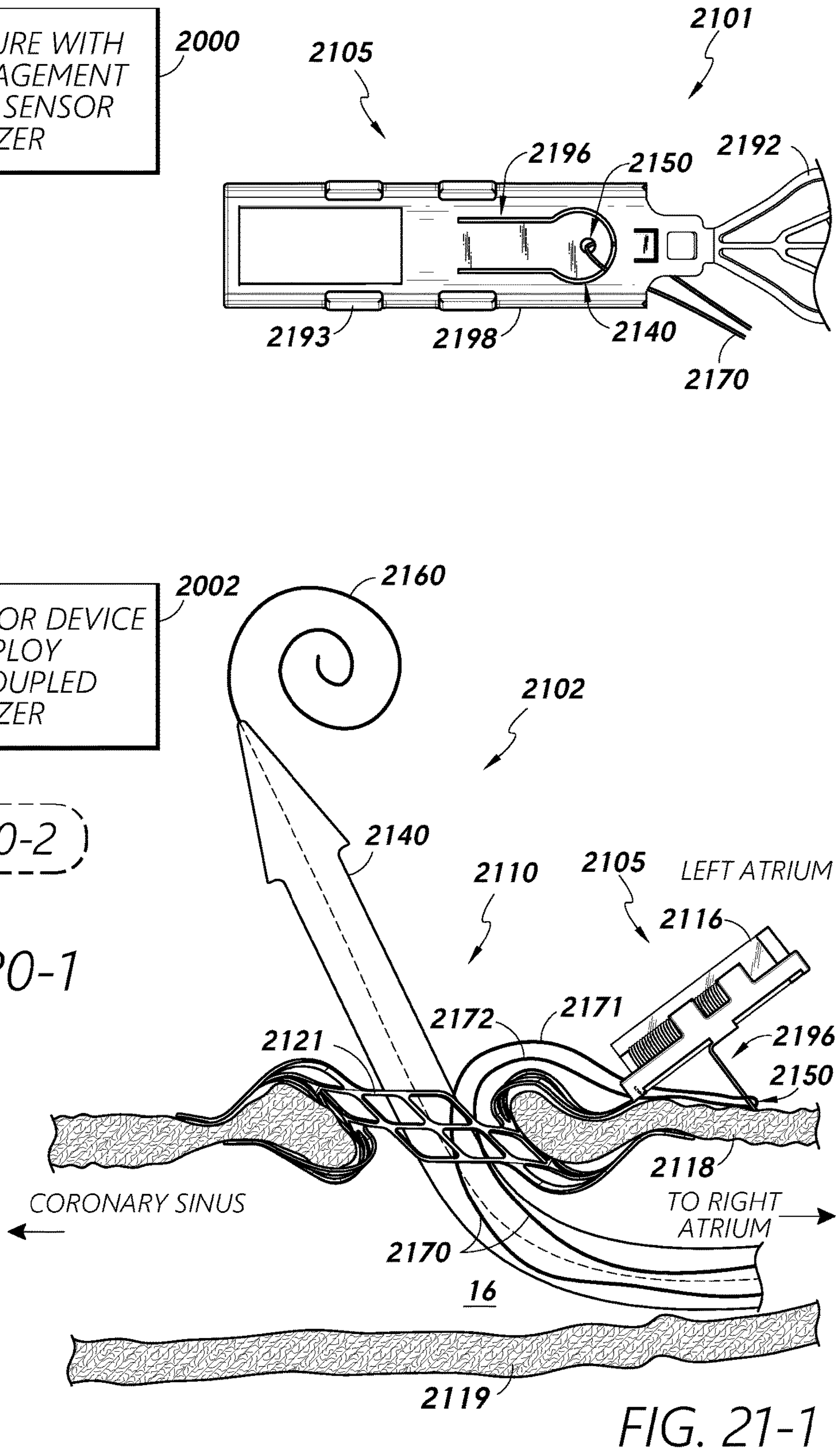
Figures 2, 20:
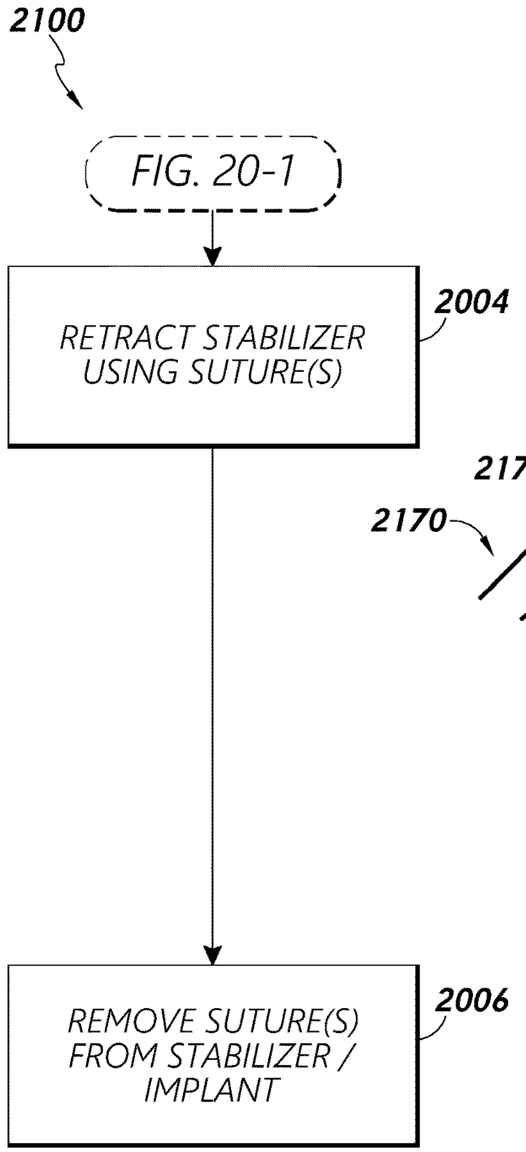
Figures 2, 21:
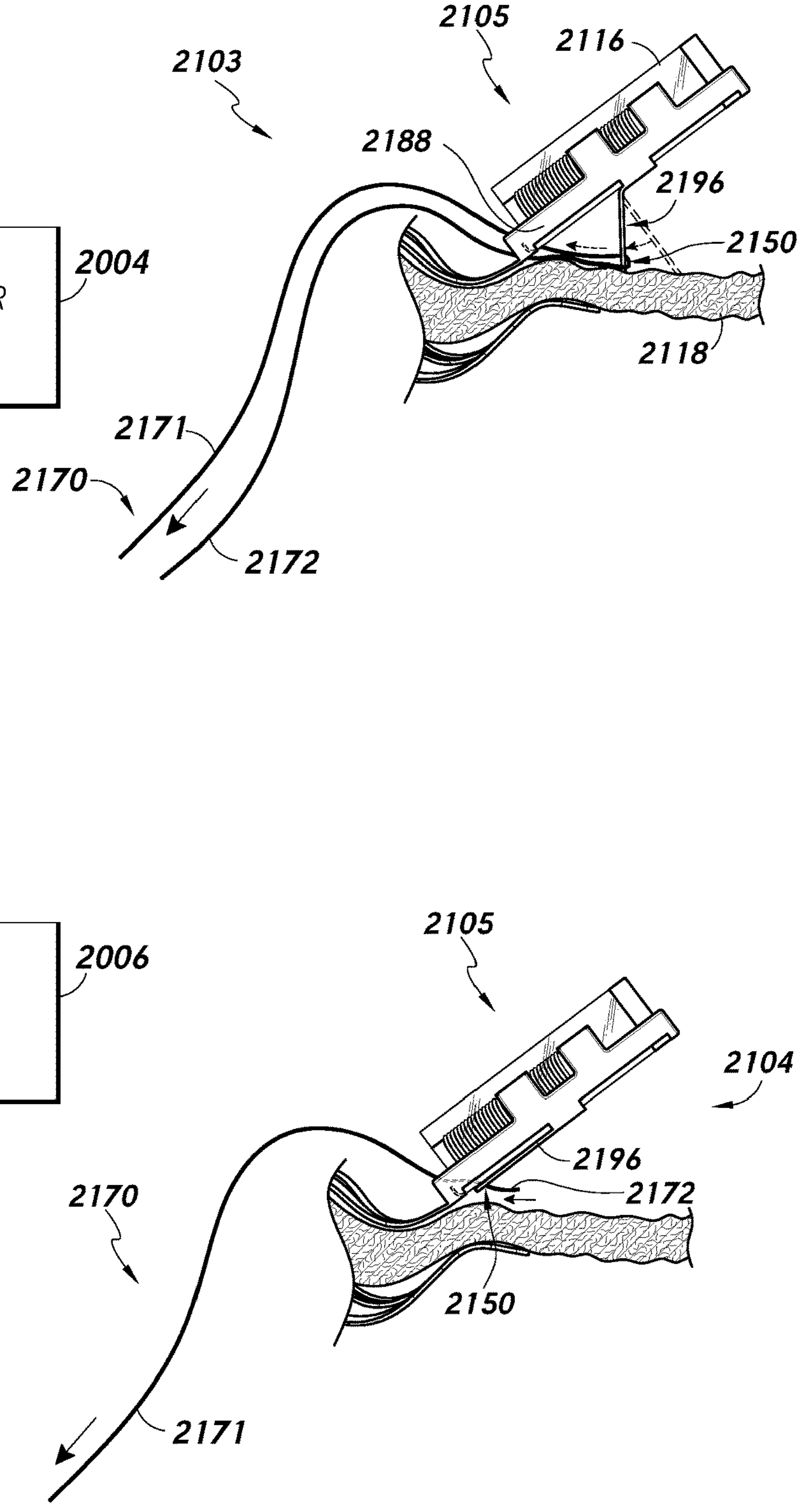

FIGS. 20-1 and 20-2 provide a flow diagram illustrating a process 2100 for implanting and retracting a sensor stabilizer in accordance with one or more embodiments. FIGS. 21-1 and 21-2 provide images of certain cardiac anatomy and devices/systems corresponding to operations of the process 2100 of FIGS. 20-1 and 20-2 according to one or more embodiments. The process 2100 relates to implantation, deployment, positioning, adjustment, and/or retraction of sensor-retention structures and/or associated retractable/retrievable stabilizer features.

The process 2100 involves, at block 2000, coupling a suture 2170 with a suture-engagement feature 2150 of a sensor stabilizer 2196, as shown in image 2101. For example, the stabilizer 2196 may be configured according to any of the embodiments of stabilizer features disclosed herein. Furthermore, although the process 2100 is described in the context of a sensor stabilizer, such as a stabilizer associated with a sensor-retention structure 2105 configured to retain/support a sensor device 2116, it should be understood that the principles disclosed herein are applicable to stabilizers used to stabilize any type of structure, whether or not associated with a medical implant device.

As shown in image 2101 of FIG. 21-1, the stabilizer 2196 may be associated with a sensor-retention structure 2105, which may be coupled to and/or associated with an arm 2192 of an implant device. In connection with the operation(s) of block 2000, a suture 2170 may be threaded through an aperture 2150 or another suture-engagement feature of the stabilizer 2196. In some embodiments, the stabilizer 2196 may include an at least partially rounded foot portion 2140, wherein the suture-engagement feature 2150 is associated with the foot feature 2140. The suture 2170 may be configured in a temporary suture loop through the suture-engagement feature 2150, which allows for recapturing or bail-out of the stabilizer feature 2196.

At block 2002, the process 2100 involves implanting a medical implant device 2110 including the sensor-retention structure 2105, which may be configured to hold a sensor device 2116, as shown in image 2102 of FIG. 21-1. The operation(s) associated with block 2002 may further involve deploying the suture-coupled stabilizer 2196, which, as described above, may have the suture 2170 engaged with a suture-engagement feature 2150 thereof. With the suture 2170 looped through and/or otherwise engaged with the suture-engagement feature 2150 of the stabilizer 2196, first 2171 and second 2172 suture tails may run from the stabilizer 2196, as shown in image 2102.

In some implementations, the sensor implant device 2110 may be delivered to the target implantation site as disposed at least partially around a delivery catheter or device 2140. The catheter 2140 may access the target anatomy, such as the left atrium or other anatomical cavity or channel by following a guide wire 2160, which may be previously disposed along the desired access path. In some embodiments, the suture tales 2171, 2172 may generally run along the catheter 2140 and/or other delivery system/device. In some implementations, the catheter 2140 may access the internal anatomy of the patient through one or more access sheaths.

At block 2004, the process 2100 involves retracting the stabilizer 2196 using the coupled suture 2170. For example, as shown in image 2103 of FIG. 21-2, retraction of the stabilizer 2196 may be accomplished by proximally pulling one or both of the suture tales 2171, 2172, thereby pulling the distal end of the stabilizer 2196, which is associated with the suture-engagement feature 2150, in a generally proximal direction and/or towards a body portion 2188 of the sensor-retention structure 2105. Pulling the stabilizer 2196 back to the body 2188 of the sensor-retention structure 2105 may return the stabilizer 2196 approximately to the delivery configuration illustrated in image 2101. In some implementations, pulling the stabilizer 2196 with the suture 2170 may not completely retract the stabilizer 2196 into the delivery configuration of image 2101, but may nevertheless retract the stabilizer 2196 to a sufficient degree to allow for removal, re-positioning, and/or adjustment of the sensor-retention structure 2105.

At block 2006, the process 2100 involves removing the suture(s) 2170 from the stabilizer 2196 and/or implant device 2110. For example, removing the suture 2170 may involve pulling on one 2171 of the suture tales, thereby causing the other suture tale 2172 to be drawn through the suture-engagement feature 2150 and removed therefrom. Although removal of the suture 2170 is shown as being performed with the stabilizer 2196 having been retracted to the delivery configuration, as shown in image 2104 of FIG. 21-2, it should be understood that suture removal from the suture-engagement feature 2150 may take place with the stabilizer 2196 in the deployed configuration as shown in image 2102, or in the retracted configuration shown in images 2103 and/or 2104.

Implant Locations for Stabilizer-Equipped Implant Devices

Implant devices incorporating stabilizer features as described in connection with the various embodiments disclosed herein can be any type of implant devices. That is, although certain shunt-type implant devices are described in detail and shown in figures of the present disclosure, it should be understood that such implant devices may be any type of implant device, including non-shunt implant devices configured to hold/retain sensor devices. Furthermore, stabilizer-equipped/supplied implant devices in accordance with aspects of the present disclosure may be implanted in any suitable or desirable anatomy, examples of which are described in detail below for reference.

Figure 22:
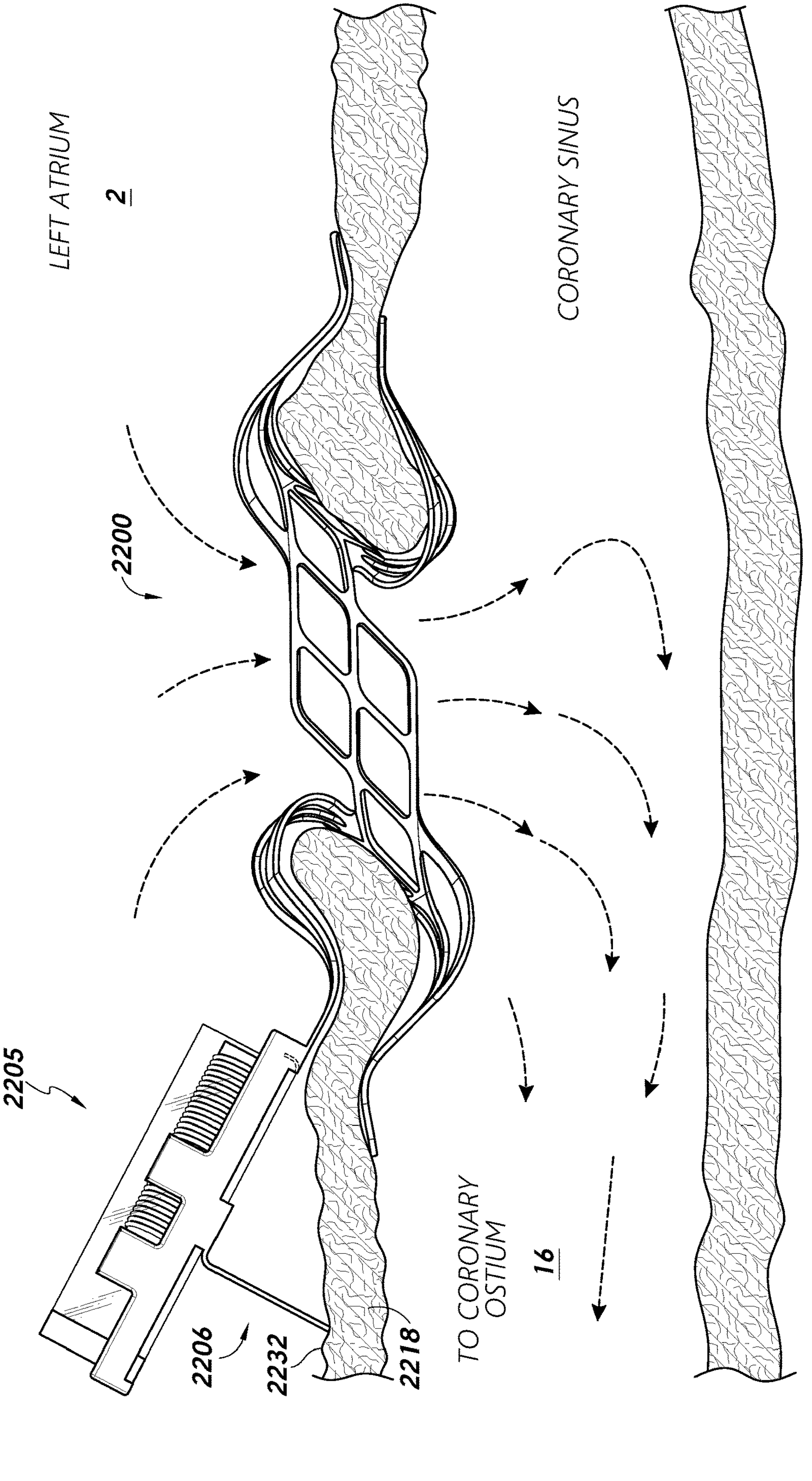
FIG. 22 shows a sensor implant device implanted in a wall separating a coronary sinus from a left atrium in accordance with one or more embodiments.

FIG. 22 shows a sensor implant device 2200 implanted in a wall 2218 separating a coronary sinus 16 from a left atrium 2 in accordance with one or more embodiments. FIG. 22, as well as a number of the following figures, shows a section of the heart from a top-down perspective with the posterior aspect oriented at the top of the page. The sensor implant device 2200 of FIG. 22 includes a sensor-retention structure 2205 having associated therewith a stabilizer feature 2206. The stabilizer 2206 may be any type of stabilizer feature as disclosed herein. With the sensor implant device 2200 implanted in the wall 2218 separating the left atrium 2 from the coronary sinus 16, the stabilizer 2206, as deployed, may contact the atrial surface 2232 of the wall 2218 separating the left atrium 2 from the coronary sinus 16.

Interatrial shunting through implantation of the implant device 2200 in the wall 18 between the left atrium 2 and the coronary sinus 16 can be preferable to shunting through the interatrial septum in some situations. For example, shunting through the coronary sinus 16 can provide reduced risk of thrombus and embolism. The coronary sinus is less likely to have thrombus/emboli present for several reasons. First, the blood draining from the coronary vasculature into the right atrium has just passed through capillaries, so it is essentially filtered blood. Second, the ostium of the coronary sinus in the right atrium is often partially covered by a pseudo-valve called the Thebesian valve. The Thebesian valve is not always present, but some studies show it is present in most hearts and can block thrombus or other emboli from entering in the event of a spike in right atrium pressure. Third, the pressure gradient between the coronary sinus and the right atrium into which it drains is generally relatively low, such that thrombus or other emboli in the right atrium is likely to remain there. Fourth, in the event that thrombus/emboli do enter the coronary sinus, there will be a much greater gradient between the right atrium and the coronary vasculature than between the right atrium and the left atrium. Most likely, thrombus/emboli would travel further down the coronary vasculature until right atrium pressure returned to normal and then the emboli would return directly to the right atrium.

Some additional advantages to locating the implant device 2200 between the left atrium and the coronary sinus is that this anatomy is generally more stable than the interatrial septal tissue. By diverting left atrial blood into the coronary sinus, sinus pressures may increase by a small amount. This can cause blood in the coronary vasculature to travel more slowly through the heart, increasing perfusion and oxygen transfer, which can be more efficient and also can help a dying heart muscle to recover.

In addition to the above-mentioned benefits, by implanting the implant device 2200 in the wall 2218 of the coronary sinus, damage to the interatrial septum may be prevented. Therefore, the interatrial septum may be preserved for later transseptal access for alternate therapies. The preservation of transseptal access may be advantageous for various reasons. For example, heart failure patients often have a number of other comorbidities, such as atrial fibrillation and/or mitral regurgitation; certain therapies for treating these conditions require a transseptal access.

It should be noted, that in addition to the various benefits of placing shunt implants between the coronary sinus and the left atrium, certain drawbacks may be considered. For example, by shunting blood from the left atrium to the coronary sinus, oxygenated blood from the left atrium may be passed to the right atrium and/or non-oxygenated blood from the right atrium may be passed to the left atrium, both of which may be undesirable with respect to proper functioning of the heart.

Figure 23B:
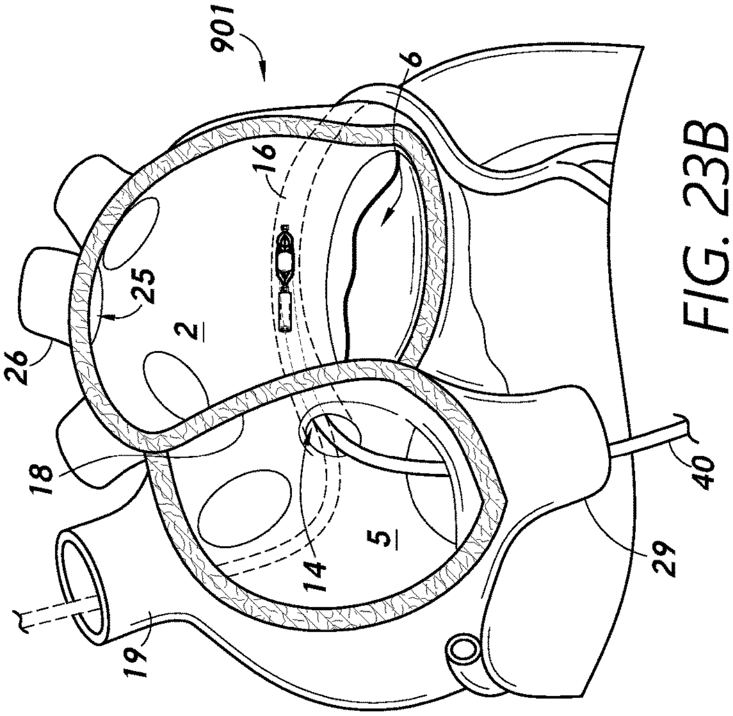
FIGS. 23A and 23B show views of cardiac anatomy showing catheter access paths to a wall separating the coronary sinus from the left atrium of a heart in accordance with one or more embodiments.
Figure 23A:
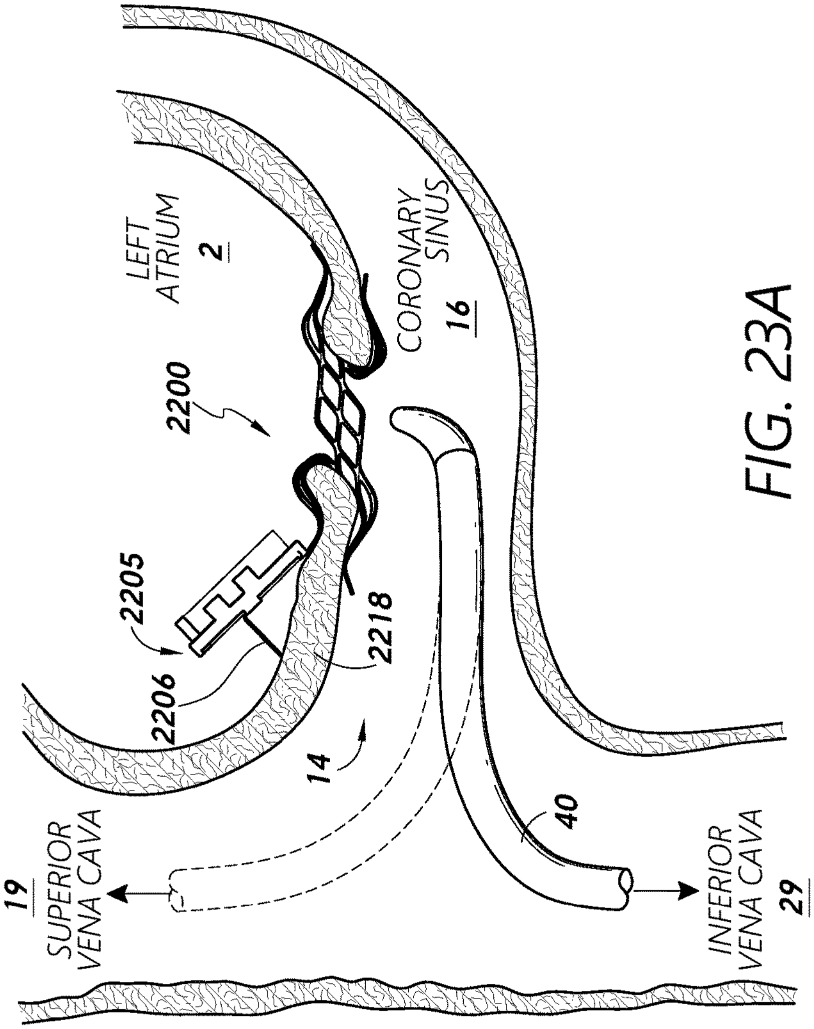

Access to the target wall 2218 via the coronary sinus 16 may be achieved using any suitable or desirable procedure. For example, various access pathways may be utilized in maneuvering guidewires and catheters in and around the heart to deploy an expandable shunt integrated or associated with a pressure sensor in accordance with embodiments of the present disclosure. FIGS. 23A and 23B show views of cardiac anatomy showing catheter access paths to the coronary sinus 16 of a heart in accordance with one or more embodiments.

In some embodiments, access may be achieved through the subclavian or jugular veins into the superior vena cava 19, right atrium 5 and from there into the coronary sinus 16. Alternatively, the access path may start in the femoral vein and through the inferior vena cava 29 into the heart. Other access routes may also be used, each of which may typically utilize a percutaneous incision through which the guidewire and catheter are inserted into the vasculature, normally through a sealed introducer, and from there the system may be designed or configured to allow the physician to control the distal ends of the devices from outside the body.

In some embodiments of procedures for advancing implant devices in accordance with aspects of the present disclosure, a guidewire is introduced through the subclavian or jugular vein, through the superior vena cava and into the coronary sinus. Once the guidewire provides a path, an introducer sheath may be routed along the guidewire and into the patient's vasculature, typically with the use of a dilator. The delivery catheter may be advanced through the superior vena cava to the coronary sinus of the heart, wherein the introducer sheath may provide a hemostatic valve to prevent blood loss. In some embodiments, a deployment catheter may function to form and prepare an opening in the wall of the left atrium, and a separate placement or delivery catheter will be used for delivery of the implant device 2200. In other embodiments, the deployment catheter may be used as the both the puncture preparation and implant delivery catheter with full functionality. In the present application, the terms "deployment catheter" or "delivery catheter" are used to represent a catheter, sheath, and/or introducer with one or both of these functions.

As shown in FIGS. 23A and 23B, the coronary sinus 16 is generally contiguous around the left atrium 2, and therefore there are a variety of possible acceptable placements for the implant device 2200. The target site selected for placement of the implant device 2200 may be made in an area where the tissue of the particular patient is less thick or less dense, as determined beforehand by non-invasive diagnostic means, such as a CT scan or radiographic technique, such as fluoroscopy or intravascular coronary echo (IVUS).

Additional aspects and features of processes for delivering implant devices that may be integrated with sensor devices/functionality in accordance with embodiments of the present disclosure for implantation in the wall between the coronary sinus and the left atrium are disclosed in U.S. Pat. No. 9,789,294, entitled "Expandable Cardiac Shunt," issued on Oct. 17, 2017, the disclosure of which is hereby expressly incorporated by reference in its entirety. Although the implant device 2200 is shown in the left atrium/coronary sinus wall 2218, the implant device 2200 may be positioned between other cardiac chambers, such as between the pulmonary artery and right atrium.

Figure 24:
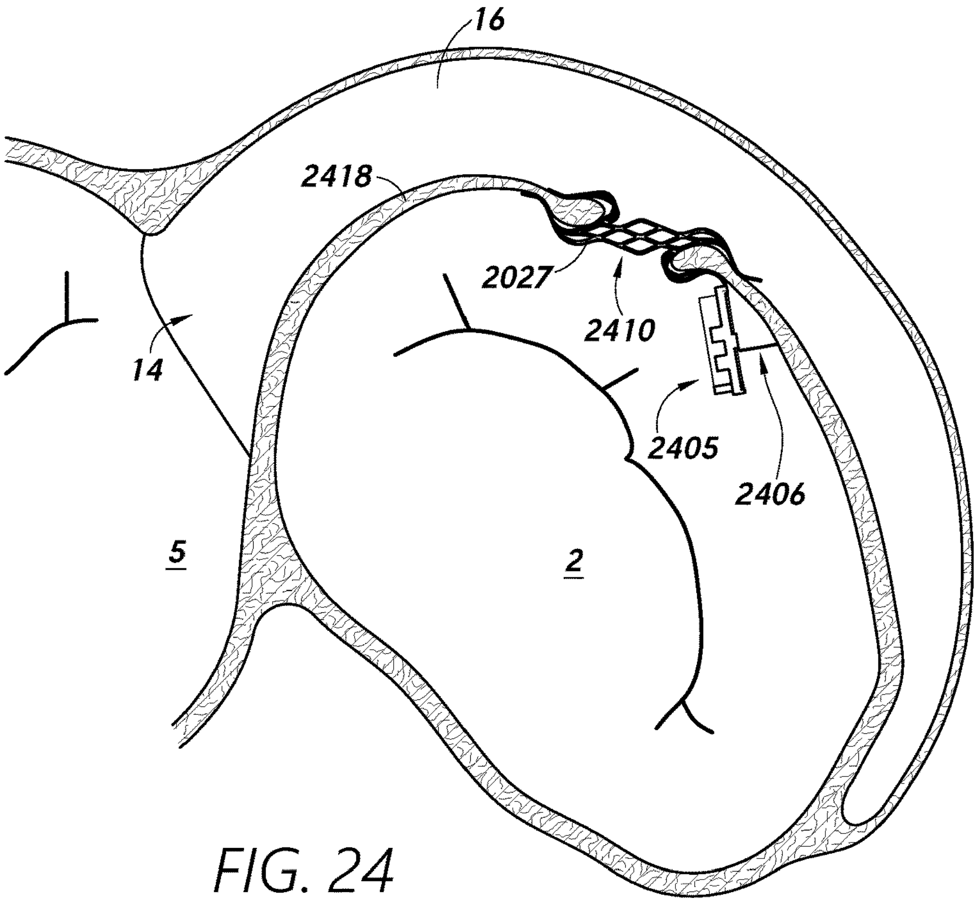
FIG. 24 shows a sensor implant device with a sensor stabilizer implanted in a wall separating a coronary sinus from a left atrium in accordance with one or more embodiments.

FIG. 24 shows a sensor implant device 2410 with a sensor stabilizer 2406 implanted in the wall 18 separating the coronary sinus 16 from the atrium 2 in accordance with one or more embodiments. Relative to the orientations of the respective sensor implant devices in FIGS. 22, 23A, and 23B, which show the sensor-retention structures associated with the respective implant devices oriented generally towards the coronary sinus ostium 14, the sensor implant device 2410 is shown in FIG. 24 as being oriented such that the sensor-retention structure 2405 associated therewith is oriented generally away from the coronary sinus ostium 14 and in the direction of the narrowing of the coronary sinus 16. However, it should be understood that sensor implant devices implanted in the wall 18 separating the left atrium 2 from the coronary sinus 16 may have any suitable or desirable orientation. For example, the arms and/or sensor-retention structures associated with sensor implant devices may be oriented generally vertically with respect to the axis of the heart, rather than horizontally as shown in FIGS. 22 and 24.

Figure 25:
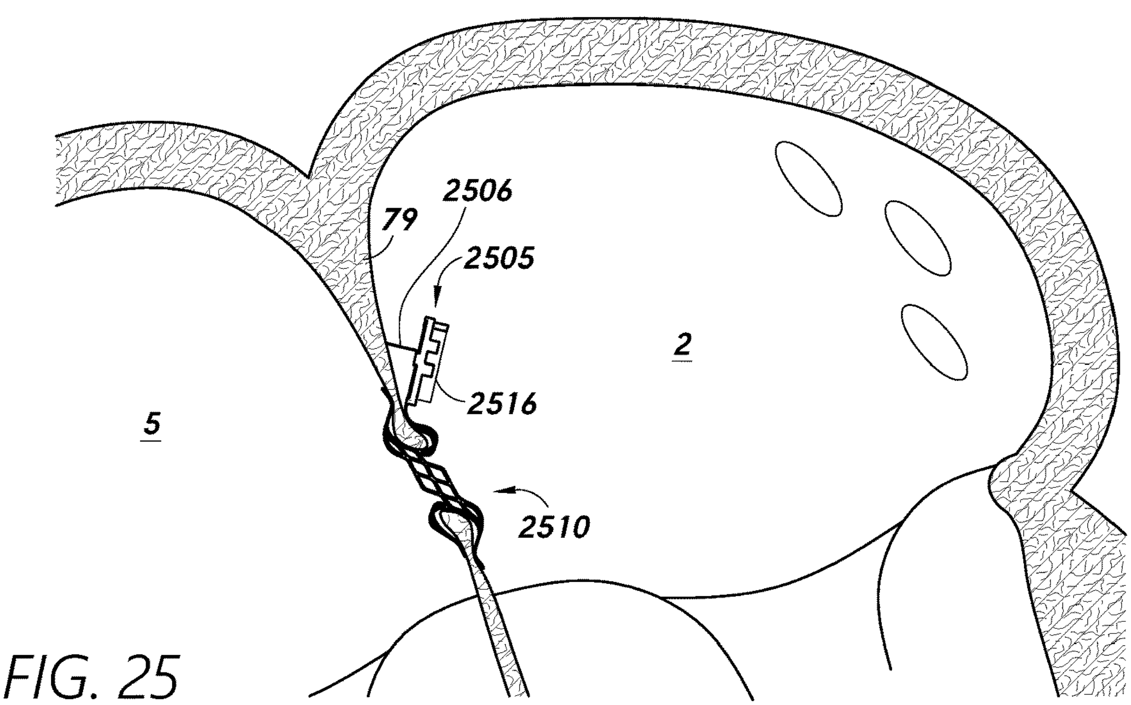
FIG. 25 shows a sensor implant device with a sensor stabilizer implanted in an interatrial septum wall in accordance with one or more embodiments.

FIG. 25 shows a sensor implant device 2510 with a sensor stabilizer 2505 implanted in an interatrial septum wall 79 in accordance with one or more embodiments. With the sensor implant device 2510 implanted in the interatrial septum 79, the sensor-retention structure 2505 and associated sensor 2516 may advantageously be disposed within the left atrium 2, as shown, thereby allowing the sensor device 2516 to detect pressure levels within the left atrium 2. However, it should be understood that in some embodiments, the sensor-retention structure 2505 may be disposed in the right atrium 5. In either configuration, the stabilizer 2506 may generally be placed in contact with the interatrial septum 79, on either the left atrial side or the right atrial side thereof depending on the orientation/configuration of the implant device 2510.

The particular position in the interatrial septum wall may be selected or determined in order to provide a relatively secure anchor location for the implant device 2510, as well as to provide a relatively low risk of thrombus. Furthermore, the sensor implant device 2510 may be implanted at a position that is desirable in consideration of future re-crossing of the septal wall 79 for future interventions. Implantation of the sensor implant device 2510 in the interatrial septum wall may advantageously allow for fluid communication between the left 2 and right 5 atria. With the device 2510 in the atrial septum 79, the sensor 2516 of the sensor implant device 2510 may advantageously be configured to measure pressure in the right atrium 5, the left atrium 2, or both atria. For example, in some embodiments, the device 2510 comprises a plurality of sensors, wherein one sensor is disposed in each of the right atrium 5 and the left atrium 2. With pressure sensor functionality for measuring pressure in both atria, the sensor implant device 2510 may advantageously be configured to provide sensor signals that may be used to determine differential pressure between the atria. Differential pressure determination may be useful for monitoring fluid build-up in the lungs, which may be associated with congestive heart failure.

Figure 26:
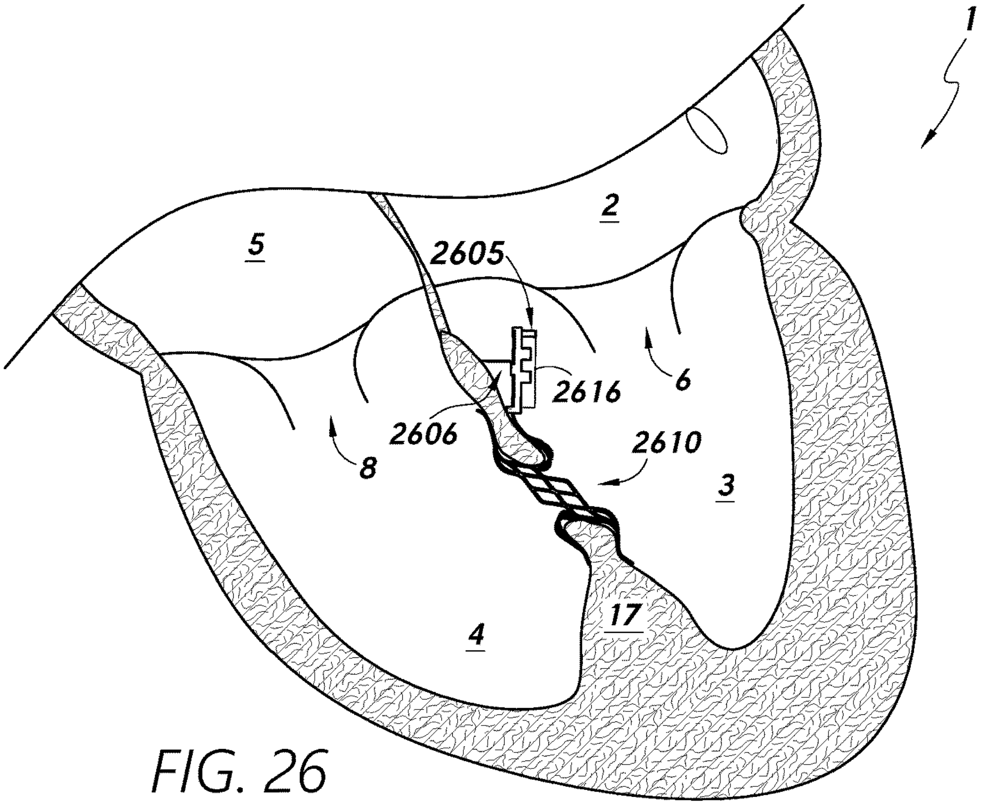
FIG. 26 shows a sensor implant device with a sensor stabilizer implanted in an interventricular septum wall in accordance with one or more embodiments.

FIG. 26 shows a sensor implant device 2610 with a sensor stabilizer 2606 implanted in an interventricular septum 17 wall in accordance with one or more embodiments. With the sensor implant device 2610 implanted in the interventricular septum 17, the sensor-retention structure 2605 and associated sensor 2616 may advantageously be disposed within the left ventricle 3, as shown, thereby allowing the sensor device 2616 to detect pressure levels within the left ventricle 3. However, it should be understood that in some embodiments, the sensor-retention structure 2605 may be disposed in the right ventricle 4. In either configuration, the stabilizer 2606 may generally be placed in contact with the septum 17, on either the left ventricle side or the right ventricle side thereof depending on the orientation/configuration of the implant device 2510.

Figure 27:
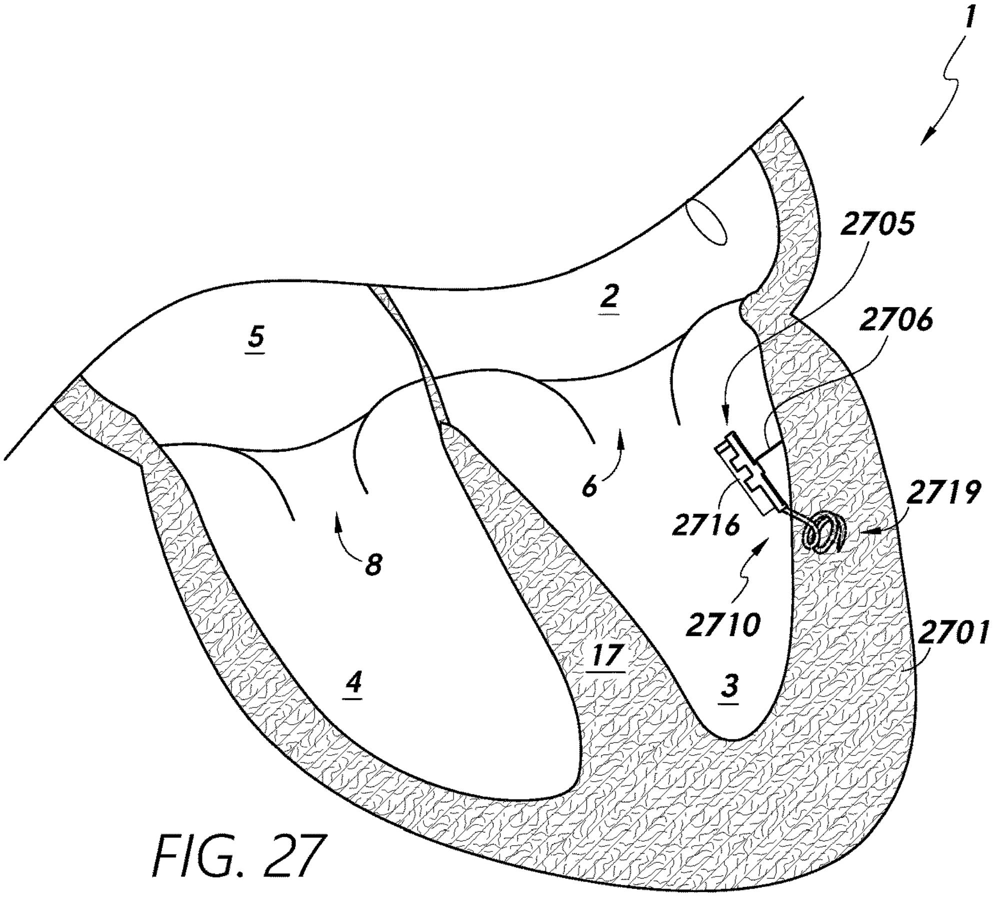
FIG. 27 shows a sensor implant device with a sensor stabilizer implanted in a wall of a ventricle of a heart in accordance with one or more embodiments.

FIG. 27 shows a sensor implant device 2710 with a sensor stabilizer 2706 implanted in a wall 2701 of a ventricle (e.g., left ventricle 3) of a heart in accordance with one or more embodiments. The wall 2701 may be generally in the area of an outer wall of the ventricle. Although the implant device 2710 is shown implanted in an outer left ventricular wall, it should be understood that implant devices in accordance with aspects of the present disclosure may be implanted in an outer wall of the right ventricle 4. The sensor implant device 2710 may have any suitable or desirable form and/or anchoring configuration. For example, corkscrew-type or other type of tissue anchor may be used to embed the proximal portion of the sensor implant device 2710 in the tissue wall 2701. Other types of tissue anchors may be implemented additionally or as an alternative to that shown in FIG. 27, such as barb-type, hook-type, and/or other anchor types. With the sensor implant device 2710 implanted in the outer ventricular wall 2701, the stabilizer 2706 may be deployed in a configuration to contact the tissue wall 2701 and provide stability for the sensor-retention structure 2705. Although illustrated as oriented generally vertically upward in the diagram of FIG. 27, it should be understood that the sensor-retention structure 2705 may be oriented in any suitable or desirable direction within the ventricle.

Figure 28:
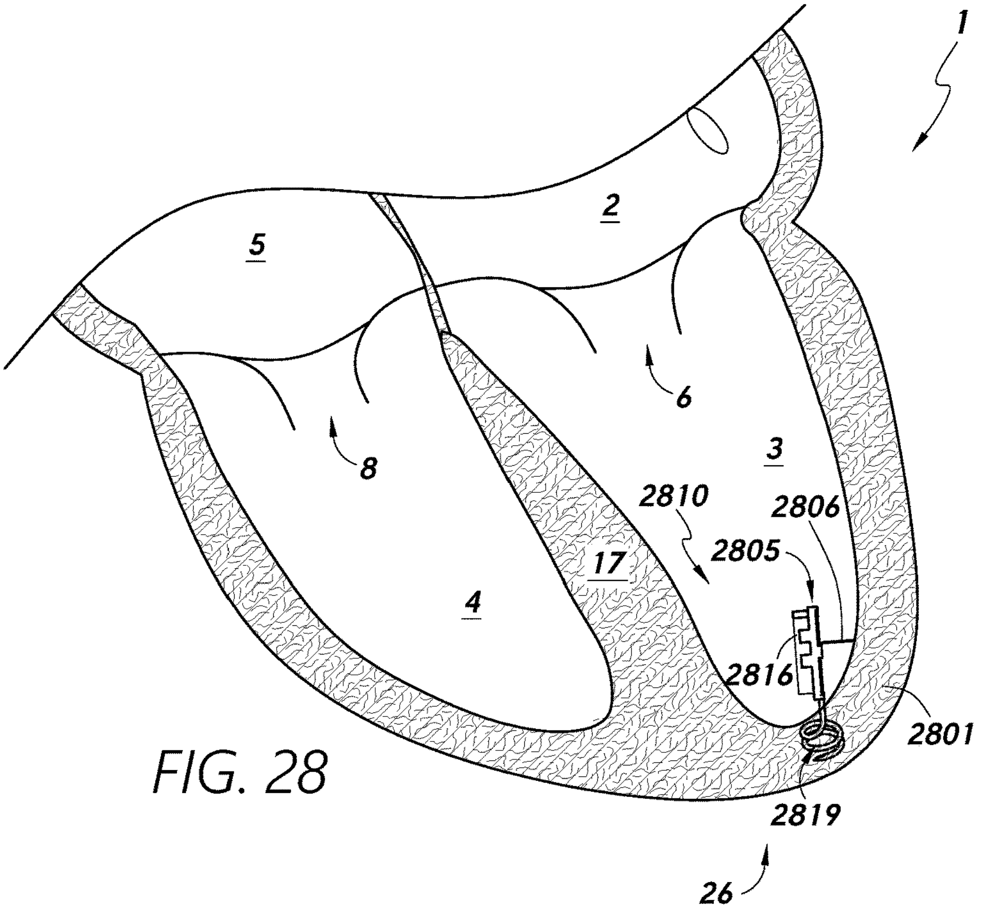
FIG. 28 shows a sensor implant device with a sensor stabilizer implanted in an apex region of a heart in accordance with one or more embodiments.

FIG. 28 shows a sensor implant device 2810 with a sensor stabilizer 2806 implanted in an apex region 26 of a heart 1 in accordance with one or more embodiments. The sensor implant device 2010 can be embedded in tissue 2801 at or near the apex 26 of the heart 1. Although illustrated in the apex area of the left ventricle 3, it should be understood that sensor implant devices in accordance with aspects of the present disclosure may be implanted in apex regions within the right atrium 4.

Figure 29:
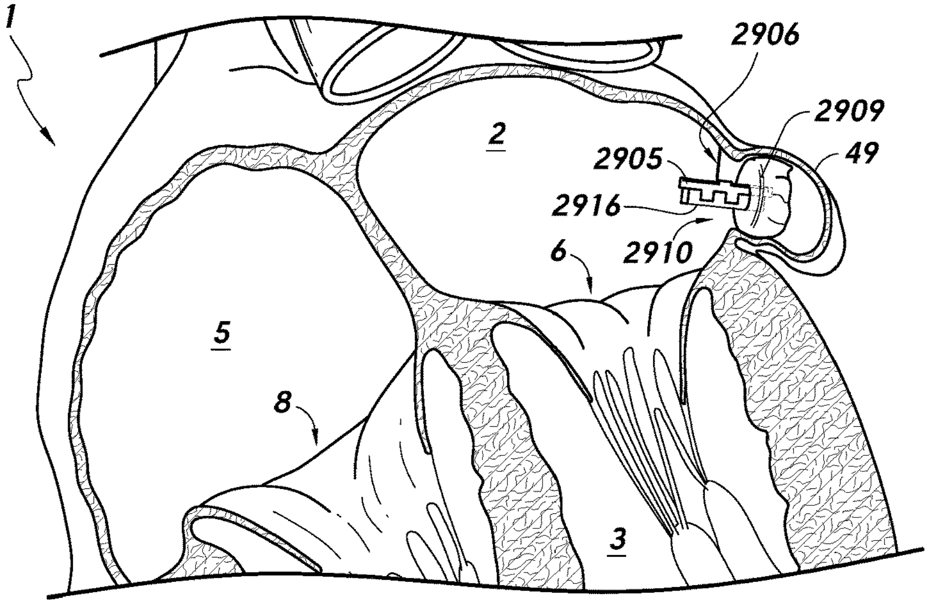
FIG. 29 shows a sensor implant device with a sensor stabilizer implanted in a left atrial appendage of a heart in accordance with one or more embodiments.

FIG. 29 shows a sensor implant device 2910 with a sensor stabilizer 2906 implanted in a left atrial appendage 249 of a heart 1 in accordance with one or more embodiments. For example, the sensor implant device 2910 may incorporate a left atrial appendage occluder component 2909. With the sensor implant device 2910 implanted as shown in FIG. 29, the stabilizer 2906 may be oriented to physically contact the sidewall of the left atrium 2.

The implant device 2910 can be positioned to measure pressure in the left atrial appendage 249 and/or left atrium 2. Generally, measurement of left atrial pressure may be useful in monitoring fluid build-up in the lungs associated with congestive heart failure, as described in detail above. The sensor implant device 2910 may be permanently affixed to the left atrial appendage closure implant device 2909 via or using any attachment or integration mechanism, including bonding, suture wrapping, or other attachment means for fixing the sensor 2916 and/or sensor-retention structure 22905 to the implant 2909. The sensor-integrated implant device 2910 may advantageously provide a secure location for anchoring the atrial pressure monitoring sensor 2916. The sensor 2916 may advantageously be positioned and/or configured to present a relatively low risk of thrombus in the left atrium.

Figure 30:
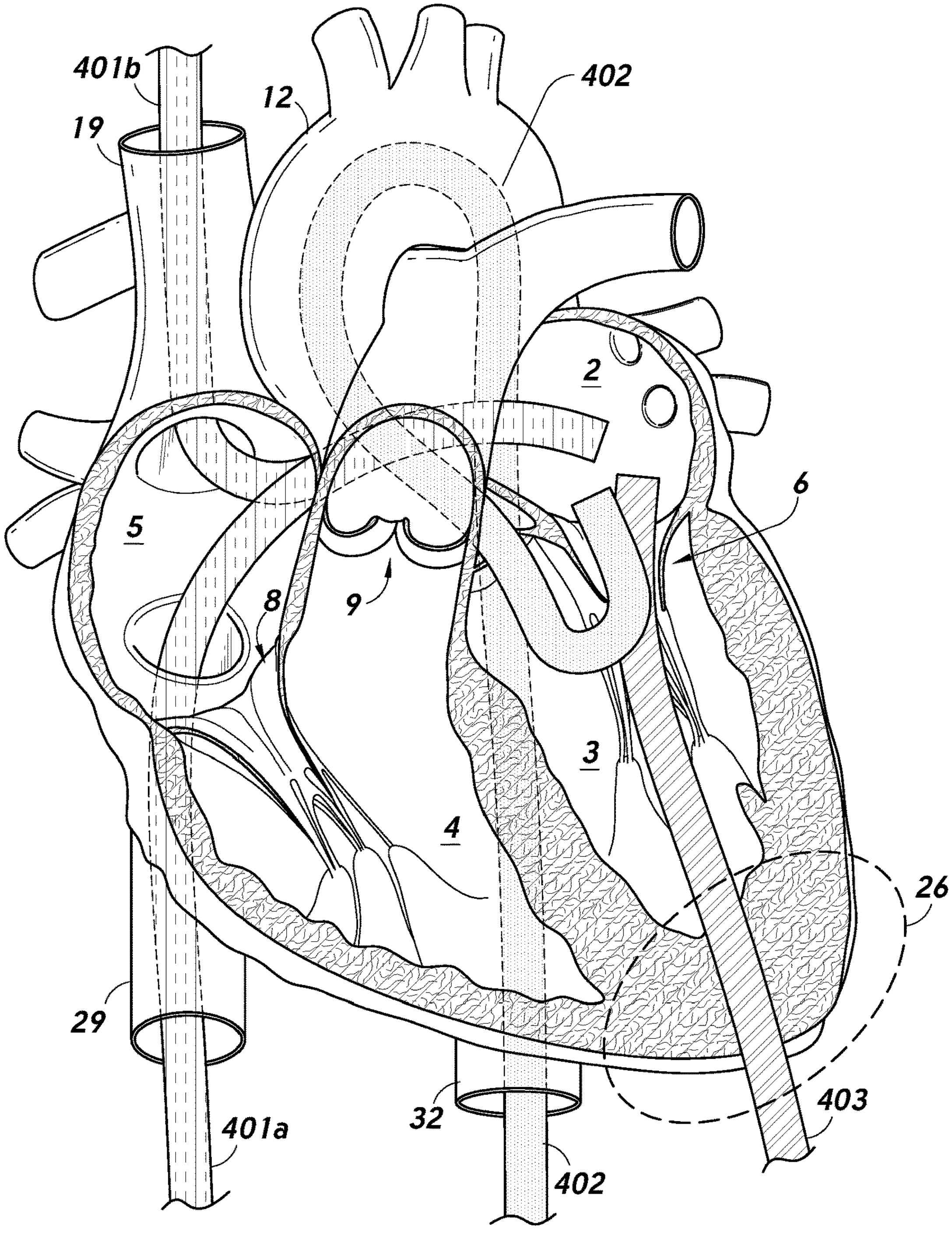
FIG. 30 illustrates various access paths through which access to a cardiac anatomy may be achieved in accordance with one or more embodiments.

Sensor implant devices in accordance with one or more embodiments of the present disclosure may be advanced to the left atrium using any suitable or desirable procedure. For example, although access to the left atrium is illustrated and described in connection with certain embodiments as being via the right atrium and/or inferior vena cavae, such as through a transfemoral or other transcatheter procedure, other access paths/methods may be implemented in accordance with embodiments of the present disclosure, as described/shown in connection with FIG. 30. For example, FIG. 30 illustrates various access paths through which access to the left ventricle may be achieved, including transseptal access 401*a*, 401*b*, which may be made through the inferior vena cava 29 or superior vena cava 19, as respectively shown, and from the right atrium 5, through the septal wall (not shown) and into the left atrium 2. For transaortic access 402, a delivery catheter may be passed through the descending aorta, aortic arch 12, ascending aorta, and aortic valve 7, and into the left atrium 2 through the mitral valve 6. For transapical access 403, access may be made directly through the apex of the heart into the left ventricle 3, and into the left atrium 2 through the mitral valve 6. Other access paths are also possible beyond those shown in FIG. 30.

CERTAIN EXAMPLES

Example 1. A sensor-retention structure comprising: a sensor-support arm configured to hold a sensor device; and a stabilizer structure associated with the sensor-support arm and configured to project away from the sensor-support arm and provide stabilizing support for the sensor-support arm.

Example 2. The sensor-retention structure of example 1, wherein the stabilizer structure comprises: an elongate leg portion; an end portion; and a base portion that is integrated with the sensor-support arm.

Example 3. The sensor-retention structure of example 2, wherein the stabilizer structure is configured to bend at the base portion to cause the end portion of the stabilizer structure to project away from a distal end of the sensor-support arm.

Example 4. The sensor-retention structure of example 2 or example 3, wherein the stabilizer structure is configured to bend at the base portion to cause the end portion of the stabilizer structure to project away from a proximal end of the sensor-support arm.

Example 5. The sensor-retention structure of any of examples 2-4, wherein the end portion of the stabilizer structure has an atraumatic coating disposed over at least a portion thereof.

Example 6. The sensor-retention structure of any of examples 2-5, wherein the end portion of the stabilizer structure comprises two feet configured to be bent in opposite directions.

Example 7. The sensor-retention structure of any of examples 2-6, wherein the end portion comprises a foot portion having a width at one or more portions thereof that is greater than a width of the elongate leg portion.

Example 8. The sensor-retention structure of any of examples 2-7, wherein the end portion comprises a foot portion that is configured to deflect at an angle relative to the elongate leg portion to provide a tissue-contact surface.

Example 9. The sensor-retention structure of any of examples 1-8, wherein the stabilizer structure comprises a first leg and a second leg.

Example 10. The sensor-retention structure of example 9, wherein the first leg and the second leg are relatively oriented in parallel.

Example 11. The sensor-retention structure of example 9 or example 10, wherein the first leg and the second leg are angled relative to one another.

Example 12. A method of deploying a sensor implant device, the method comprising:

- implanting an implant structure in a tissue wall, the implant structure including a sensor-support member configured to retain a sensor device; and
- projecting a distal portion of a stabilizer form associated with the sensor-support member away from the sensor-support member and towards the tissue wall.

Example 13. The method of example 12, further comprising stabilizing the sensor-support member with respect to an angle of the sensor-support member relative to a surface of the tissue wall.

Example 14. The method of example 12 or example 13, further comprising deflecting an end portion of the stabilizer form to provide a tissue-contact structure.

Example 15. The method of any of examples 12-14, wherein the stabilizer form comprises shape-memory material, and said projecting the distal portion of the stabilizer form involves deploying the implant structure from a delivery system and allowing the shape-memory material to cause the stabilizer form to bend at a base thereof to deflect the stabilizer form away from the sensor-support member.

Example 16. A method of retracting a sensor stabilizer, the method comprising: providing a sensor implant device including a sensor-support structure and a stabilizer member including a suture-engagement feature; engaging a suture with the suture-engagement feature; implanting the sensor implant device in a tissue wall; deploying the stabilizer member at least in part by projecting at least a portion of the stabilizer member away from the sensor-support structure; and pulling one or more portions of the suture to thereby pull the stabilizer member into alignment with the sensor-support structure.

Example 17. The method of example 16, wherein the suture-engagement feature comprises an aperture associated with an end portion of the stabilizer member.

Example 18. The method of example 16 or example 17, further comprising pulling a suture tail of the suture proximally through a delivery system associated with the sensor implant device to withdraw the suture from the sensor implant device.

Example 19. The method of any of examples 16-18, further comprising advancing a delivery catheter to the tissue wall, the delivery catheter having disposed therein a plurality of suture tail portions of the suture.

Example 20. The method of any of examples 16-19, wherein the tissue wall is a wall separating a coronary sinus from a left ventricle of a heart.

Additional Embodiments

Depending on the embodiment, certain acts, events, or functions of any of the processes described herein can be performed in a different sequence, may be added, merged, or left out altogether. Thus, in certain embodiments, not all described acts or events are necessary for the practice of the processes.

Certain standard anatomical terms of location are used herein with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. Spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present. As used herein, the term "and/or" used between the last two of a list of elements means any one or more of the listed elements. For example, the phrase "A, B, and/or C" means "A," "B," "C," "A and B," "A and C," "B and C," or "A, B, and C."

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

With respect to the various methods and processes disclosed herein, although certain orders of operations or steps are illustrated and/or described, it should be understood that the various steps and operations shown and described may be performed in any suitable or desirable temporal order. Furthermore, any of the illustrated and/or described operations or steps may be omitted from any given method or process, and the illustrated/described methods and processes may include additional operations or steps not explicitly illustrated or described.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above but should be determined only by a fair reading of the claims that follow.

What is claimed is:

1. A sensor-retention structure comprising:

a sensor-support arm configured to hold an elongate cylindrical sensor device, the sensor-support arm comprising a curved cradle form shaped as a cylindrical arc structure, the curved cradle form including opposing sidewall segments and sensor-retention fingers projecting circumferentially from each of the opposing sidewall segments, the opposing sidewall segments and sensor-retention fingers being configured to partially rise along an outer surface of the sensor device so as to receive and retain the sensor device therein; and a stabilizer structure associated with the sensor-support arm and configured to deflect away from the sensor-support arm and provide stabilizing tissue-contact support for the sensor-support arm to hold the sensor-support arm at an angled orientation relative to a tissue wall.

2. The sensor-retention structure of claim 1, wherein the stabilizer structure comprises:

an elongate leg portion;

an end portion; and a base portion that is integrated with the sensor-support arm.

3. The sensor-retention structure of claim 2, wherein the stabilizer structure is configured to bend at the base portion to cause the end portion of the stabilizer structure to deflect away from a distal end of the sensor-support arm.

4. The sensor-retention structure of claim 2, wherein the stabilizer structure is configured to bend at the base portion to cause the end portion of the stabilizer structure to deflect away from a proximal end of the sensor-support arm.

5. The sensor-retention structure of claim 2, wherein the end portion of the stabilizer structure has an atraumatic coating disposed over at least a portion thereof.

6. The sensor-retention structure of claim 2, wherein the end portion of the stabilizer structure comprises two feet configured to be bent in opposite directions.

7. The sensor-retention structure of claim 2, wherein the end portion comprises a foot portion having a width at one or more portions thereof that is greater than a width of the elongate leg portion.

8. The sensor-retention structure of claim 2, wherein the end portion comprises a foot portion that is configured to deflect at an angle relative to the elongate leg portion to provide a tissue-contact surface.

9. The sensor-retention structure of claim 1, wherein the stabilizer structure comprises a first leg and a second leg.

10. The sensor-retention structure of claim 9, wherein the first leg and the second leg are relatively oriented in parallel.

11. The sensor-retention structure of claim 9, wherein the first leg and the second leg are angled relative to one another.

12. A sensor-retention structure comprising:

a shunt body shaped for implantation in a tissue wall separating first and second anatomical spaces, the shunt body defining a flow channel that passes through the tissue wall when implanted;

a plurality of tissue-engaging anchor arms extending from the shunt body and configured to deploy radially outward to engage tissue on opposite sides of the tissue wall to thereby secure the shunt body in the tissue wall;

a sensor-holding extension extending from one of the plurality of tissue-engaging anchor arms and shaped to receive and retain a sensor device; and a sensor-stabilizing structure coupled to the sensor-holding extension, the sensor-stabilizing structure including a base portion integrated with the sensor-holding extension and configured to bend, an elongate leg extending from the base portion, and a tissue-contact end portion configured to contact the tissue wall to space the sensor-holding extension from the tissue wall at an angled orientation relative to the tissue wall;

wherein the sensor-holding extension comprises a cradle form shaped to conform to a shape of the sensor device, the cradle form including opposing sidewall segments and configured to partially rise along an outer surface of the sensor device so as to receive the sensor device.

13. The sensor-retention structure of claim 12, wherein the cradle form is curved and shaped as a cylindrical arc segment, the curved cradle form including a plurality of retention fingers that rise along the outer surface of the sensor device so as to retain the sensor device.

14. The sensor-retention structure of claim 13, wherein:

the cylindrical arc segment is defined by longitudinal side support walls that form the opposing sidewall segments and are connected by one or more circumferentially-extending back support bands;

a cradle structure consisting of the longitudinal side support walls and the one or more circumferentially-extending back support bands cover less than 180 degrees of a full cylinder.

15. The sensor-retention structure of claim 13, wherein the sensor-holding extension further comprises a back-support band extending across a lengthwise central region of the curved cradle form and configured to provide a resting support surface for the sensor device, the back-support band defining a first window opening on one of a proximal or distal side thereof between the opposing sidewall segments.

16. The sensor-retention structure of claim 15, wherein the sensor-stabilizing structure is formed from a cut-out region of the sensor-holding extension such that deflection of the sensor-stabilizing structure away from the cradle form exposes a second window opening in the cradle form on an opposite side of the back-support band from the first window opening.

17. The sensor-retention structure of claim 13, wherein a distal cross-bar of the sensor-holding extension extends transversely across a lower peripheral portion of the cylindrical arc segment to provide an interference stop configured to contact a distal end of the sensor device and inhibit distal axial movement of the sensor device relative to the curved cradle form.

18. The sensor-retention structure of claim 12, further comprising a plurality of pairs of retention fingers that project from each of the opposing sidewall segments to retain the sensor device against the cradle form.

19. A sensor-retention structure comprising:

a tubular frame defining a flow passage;

a plurality of anchor arms configured to deflect radially from an axial end of the tubular frame to secure the tubular frame relative to a tissue wall, each of the plurality of anchor arms including, when deployed:

a base segment that projects axially and radially outward from the tubular frame; and a distal segment distal of the base segment that deflects back toward tissue wall and terminates with a tissue-contact end;

a sensor holder extending distally from the tissue-contact end of one of the plurality of anchor arms and configured to support an elongate cylindrical sensor device in an orientation that is angled relative to an axis of the tubular frame and a plane of the tissue wall, the sensor holder having a curved cradle form including opposing sidewall segments and retention fingers configured to rise along an outer surface of the cylindrical sensor device so as to receive and retain the cylindrical sensor device; and a stabilizer member coupled to the sensor holder, the stabilizer member comprising a bendable base portion, an elongate leg extending from the base portion, and a tissue-contacting end portion, the stabilizer member being configured to bend away from the sensor holder such that the tissue-contacting end portion engages the tissue wall and cooperates with the sensor holder to establish a controlled angular orientation of the sensor holder relative to the tissue wall.

20. The sensor-retention structure of claim 19, wherein the stabilizer member is configured to bend to an angle substantially perpendicular to a length dimension of the sensor holder.

* * * * *